US009198910B2

(12) United States Patent
Bussey et al.

(10) Patent No.: US 9,198,910 B2
(45) Date of Patent: Dec. 1, 2015

(54) METHODS FOR THE TREATMENT OF CANCER

(71) Applicant: The Translational Genomics Research Institute, Phoenix, AZ (US)

(72) Inventors: Kimberly J. Bussey, Phoenix, AZ (US); Michael J. Demeure, Phoenix, AZ (US); Aditi Bapat, Phoenix, AZ (US)

(73) Assignee: THE TRANSLATIONAL GENOMICS RESEARCH INSTITUTE, Phoenix, AZ (US)

( * ) Notice: Subject to any disclaimer, the term of this patent is extended or adjusted under 35 U.S.C. 154(b) by 0 days.

(21) Appl. No.: 14/245,188

(22) Filed: Apr. 4, 2014

(65) Prior Publication Data

US 2014/0303120 A1 Oct. 9, 2014

Related U.S. Application Data

(60) Provisional application No. 61/808,462, filed on Apr. 4, 2013.

(51) Int. Cl.

| | |
|---|---|
| ***C12Q 1/68*** | (2006.01) |
| ***A61K 31/519*** | (2006.01) |
| ***A61K 31/496*** | (2006.01) |
| ***A61K 45/06*** | (2006.01) |
| ***A61K 31/366*** | (2006.01) |
| ***A61K 31/4184*** | (2006.01) |
| ***A61K 31/428*** | (2006.01) |
| ***A61K 31/437*** | (2006.01) |
| ***A61K 31/47*** | (2006.01) |
| ***A61K 31/69*** | (2006.01) |

(52) U.S. Cl.

CPC ............ *A61K 31/519* (2013.01); *A61K 31/366* (2013.01); *A61K 31/4184* (2013.01); *A61K 31/428* (2013.01); *A61K 31/437* (2013.01); *A61K 31/47* (2013.01); *A61K 31/496* (2013.01); *A61K 31/69* (2013.01); *A61K 45/06* (2013.01)

(58) Field of Classification Search

None

See application file for complete search history.

(56) References Cited

PUBLICATIONS

Braunschweig et al (Proteomics Clin. Appl., 2007, 1: 264-271).*
Steegmaier et al (Current Biology, 2007, 17: 316-322).*
Mross et al (Journal of Clinical Oncology, 2008, 26(34): 5511-5517).*
Vassilev et al (Science, 2004, 303: 844-848).*
Endo et al (Cancer Science, 2011, 102(3): 605-613).*

* cited by examiner

*Primary Examiner* — Sean Aeder

(74) *Attorney, Agent, or Firm* — Kenneth Ralston; Michael J. Donovan

(57) ABSTRACT

The present invention is directed to methods for treating cancer in a subject, such as a cancer of the endocrine system. In some aspects, the method includes administering to the subject one or more of a polo-like kinase 1 inhibitor, a mouse double minute 2 inhibitor, and/or a mitotic catastrophe inducing compound. In other aspects, the method includes measuring an expression level of one or more markers, including caspase 8 and caspase 9, to assess the functionality of the caspase cascade in the subject.

14 Claims, 22 Drawing Sheets

A

B

A

B

C

D

E

C

C

E

METHODS FOR THE TREATMENT OF CANCER

CROSS-REFERENCE TO RELATED APPLICATIONS

The present application claims priority to U.S. Application No. 61/808,462, filed Apr. 4, 2013, the entire contents and disclosure of which are herein incorporated by reference.

INCORPORATION-BY-REFERENCE OF MATERIAL ELECTRONICALLY FILED

Incorporated by reference in its entirety herein is a computer-readable nucleotide/amino acid sequence listing submitted concurrently herewith and identified as follows: One 61 kilobyte ASCII (text) file named "ACCSeq_List_ST25" created on Apr. 3, 2014.

FIELD OF THE INVENTION

This application relates to methods for the treatment of one or more forms of cancer and more particularly, relates to the assessment of the functionality of the caspase cascade in a subject and methods of circumventing defects in the functionality.

BACKGROUND OF THE INVENTION

Cancers with less than 40,000 cases diagnosed per year in the U.S. are both an unmet medical need and unparalleled opportunity. Rare cancers have been the basis of paradigm-defining concepts in cancer because their rarity comes from the limited combinations of events that result in that particular type of cancer. For example, the first instance of a translocation driven oncogenic event, BRC-ABL, was discovered in seven cases of chronic myelogenous leukemia. Nowell P C & D A Hungerford, *A minute chromosome in human chronic granulocytic leukemia*, Science (142) 1497 (1960). The role of tumor suppressors, particularly p53 and RB1, was found through the investigation of tumors from patients with Li-Fraumeni syndrome and familial retinoblastoma, respectively. As researchers find necessary and sufficient genetic changes that drive rare cancers, these can be further studied to understand and treat more common cancers. If researchers can identify what core cancer pathways are operational in a rare tumor, the knowledge about those pathways from more common cancers can be leveraged to improve diagnosis and treatment.

Adrenocortical carcinoma (ACC) is an aggressive cancer of the adrenal cortex. Recent studies show that the outcome for ACC patients has remained unchanged in the past 25 years, with a 40% overall 5-year survival rate of patients undergoing surgical resection. K Y Bilimoria et al., *Adrenocortical carcinoma in the United States: treatment utilization and prognostic factors*, Cancer (113) 3130-3136 (2008). ACC is rare with an incidence of approximately 300 new cases per year in the United States. Id. The rarity of ACC suggests either a specific genomic alteration, or a small number of alterations, is necessary and sufficient for tumor development. Childhood ACC is a feature of the Li-Fraumeni syndrome and mutation of p53, but inactivating mutations in p53 are an uncommon feature of adult ACC. R. Libe et al., *Somatic TP53 mutations are relatively rare among adrenocortical cancers with the frequent 17p13 loss of heterozygosity*, Clinical Cancer Res. (13) 844-850 (2007). Comparative genomic hybridization studies demonstrate that no abnormality has been seen in more than 60% of ACCs examined. Bussey K J & M J Demeure, *Genomic and expression profiling of adrenocortical carcinoma: application to diagnosis, prognosis and treatment*, Future Oncol. (5) 641-655 (2009). This implies that the necessary and sufficient alteration(s) responsible for the pathogenesis of ACC exist either below the limit of detection or resolution of previously used technologies and/or result from structural events that do not consistently alter copy number. It could also imply that there is genomic heterogeneity that converges on a small number of critical pathways resulting in this rare disease.

ACC patients who present clinically with large, locally invasive tumors, have involved margins or present with metastatic disease, fare considerably worse with 5 year survival rates of 10-20%, largely due to the limited effectiveness of chemotherapy. The only realistic opportunity for cure is a complete surgical resection. Unfortunately, metastatic spread is already present in 40-70% of patients at the time of diagnosis precluding cure. Standard chemotherapy in ACC cases remains based on mitotane which was first approved in 1960. Mitotane, also known as o,p'-DDD, is a derivative of the pesticide DDT and an adrenolytic. Tacon, L. J. et al., *Current and emerging therapies for advanced adrenocortical carcinoma*. Oncologist (16) 36-48 (2011); Daffara, F. et al., *Prospective evaluation of mitotane toxicity in adrenocortical cancer patients treated adjuvantly* Endocr. Relat. Cancer (15) 1043-53 (2008); Netto, A. D. et al., *Treatment of Adrenocortical Cancer with O,P'-Ddd*. Ann. Intern. Med. (59) 74-78 (1963); and Bapat, A. A. et al., *A fly in the ointment: reassessing mitotane's role in the treatment of adrenocortical carcinoma*. Pharmacogenomics (13) 1207-1209 (2012). The response rates to mitotane as a single agent is a relatively poor 23%, but survival for those patients whose tumors do respond is improved from 14 to 50 months. Tacon, L. J. et al., *Current and emerging therapies for advanced adrenocortical carcinoma*. Oncologist (16) 36-48 (2011); Daffara, F. et al., *Prospective evaluation of mitotane toxicity in adrenocortical cancer patients treated adjuvantly*. Endocr. Relat. Cancer, (15) 1043-53 (2008); and Netto, A. D. et al., *Treatment of Adrenocortical Cancer with O,P'-Ddd*. Ann. Intern. Med. (59) 74-78 (1963). Mitotane is most often used in combination with etoposide, doxorubicin, and cisplatin (EDP-M) based on the reported 49% response rate in a phase II trial. Berruti, A. et al., *Etoposide, doxorubicin and cisplatin plus mitotane in the treatment of advanced adrenocortical carcinoma: a large prospective phase II trial* Endocr. Relat. Cancer. (12) 657-666 (2005). However, further study in the phase III FIRM-ACT trial demonstrated the response rate to EDP-M was 23.2% and the median progression-free survival interval was 5 months. Fassnacht, M. et al., *Combination Chemotherapy in Advanced Adrenocortical Carcinoma*. N. Engl. J. Med. (366) 2189-2197 (2012). For most patients, mitotane is poorly tolerated due to its severe toxic side effects, including obliteration of the healthy contralateral adrenal gland. There is no approved second-line regimen for those whose disease progresses on these agents.

The increased incidence of ACC in patients with Li-Fraumeni syndrome suggests the p53 pathway is involved in ACC progression. Fassnacht, M. et al., *Adrenocortical carcinoma: a clinician's update* Nat. Rev. Endocrinol. (7) 323-335 (2011). In adults, however, mutation in p53 is seen in less than 25% of cases suggesting that other elements of the p53 pathway may be perturbed. Waldmann, J. et al., *Clinical impact of TP53 alterations in adrenocortical carcinomas* Langenbecks Arch. Surg. (397) 209-216 (2012); Libe, R. et al., *Somatic TP53 mutations are relatively rare among adrenocortical cancers with the frequent 17p13 loss of heterozygosity* Clin.

Cancer Res. (13) 844-850 (2007); and Hamid, T. and S. S. Kakar, *PTTG/securin activates expression of p53 and modulates its function* Mol. Cancer (3) 18 (2004). It has been found that p53 is a major driver of differential gene expression when comparing ACC to normal adrenal glands or when comparing low and high-grade tumors. Demeure, M. J. et al., *PTTG1 overexpression in adrenocortical cancer is associated with poor survival and represents a potential therapeutic target* Surgery (154) 1405-1416 (2013). This dysregulation is accompanied by perturbations in the G2/M transition of the cell cycle. Demeure, M. J. et al., *PTTG1 overexpression in adrenocortical cancer is associated with poor survival and represents a potential therapeutic target* Surgery (154) 1405-1416 (2013). Moreover, Polo-like kinase 1 (PLK-1) negatively modulates p53 functioning, promotes Mouse double minute 2 (MDM2) activity through its phosphorylation, and is involved in the G2/M transition. X. Liu et al., *Polo-like Kinase (Plk)1 depletion induces apoptosis in cancer cells*, Proc. Nat. Acad. Sci. (100) 5789-5794 (2003).

p53 is a tumor suppressor and transcription factor that responds to cellular stress by activating the transcription of numerous genes involved in cell cycle arrest, apoptosis, senescence, and DNA repair. Unlike normal cells, which have infrequent cause for p53 activation, tumor cells are under constant cellular stress from various insults including hypoxia and pro-apoptotic oncogene activation. Thus, there is a strong selective advantage for inactivation of the p53 pathway in tumors, eliminating p53 function may be a prerequisite for tumor survival. Mouse models have been used to demonstrate that absence of p53 function is a continuous requirement for the maintenance of established tumors; when p53 function is restored to tumors with inactivated p53, the tumors regressed.

p53 is inactivated by mutation and/or loss in 50% of solid tumors and 10% of liquid tumors. Other key members of the p53 pathway are also genetically or epigenetically altered in cancer. MDM2, an oncoprotein, inhibits p53 function, and it is activated by gene amplification at incidence rates that are reported to be as high as 10%. MDM2, in turn, is inhibited by another tumor suppressor, p14ARF. Alterations downstream of p53 may be responsible for at least partially inactivating the p53 pathway in p53 wild type tumors (p53WT). In support of this concept, some p53WT tumors appear to exhibit reduced apoptotic capacity, although their capacity to undergo cell cycle arrest remains intact. MDM2 inhibits p53 activity by three mechanisms: 1) acting as an E3 ubiquitin ligase to promote p53 degradation; 2) binding to and blocking the p53 transcriptional activation domain; and 3) exporting p53 from the nucleus to the cytoplasm.

Apoptosis is an active form of cell death that is involved in multiple processes of normal cell development as well as in malignant cell transformations. Mechanism of apoptosis is engaged in biological events induced by various types of drugs, cytokines, and growth factors, oxidative stress, radiation, aging, autoimmune diseases, and immune rejection within organ transplantation. Recent studies on apoptosis demonstrate that common molecular mechanisms are employed in various types of apoptosis, induced by hormones, cytokines, growth factor deprivation, chemotherapeutic agents, ionizing radiation, immunological disorders, AIDS, cancer and aging.

Cascade-like activation of caspase proteases represents a point in the induction of apoptosis. Two types of apoptosis signaling mediated by the caspase cascade have been described: receptor-dependent and receptor-independent. The initial phase of receptor-depending triggering of apoptosis includes activation of appropriate death receptors by specific ligands, such as TNF or FasL, which are presently the most studied inductors of apoptosis. Upon activation, cell surface death receptors, Fas (CD95) or TNFR1, are attached to cytosolic adapter proteins (FADD, MORT, RIP, TRADD), which in turn recruit caspase-8 to activate the interleukin-1-β-converting enzyme ICE/CED-3 family caspase cascade, followed by activation of CPP32/caspase-3-subfamily of cysteine proteases, whose members are localized in the cytoplasm in the form of latent precursors known as procaspases. Receptor-independent types of caspase cascade-mediated apoptosis usually include important cytochrome c-inducible mechanism that requires the formation of tertiary complex of cytochrome c, dATP, Apaf-1 and procaspase-9, which lead to the activation of the latter via autoproteolysis and homodimerization, and subsequent caspase cascade activation. See D. R. McIlwain et al. *Caspase Functions in Cell Death and Disease* Cold Spring Harbor Perspectives in Biology (5) a008656 (2013). In general, caspases involved in mediating apoptosis have been generally divided by function: (i) initiator caspases (i.e., caspases 8 and 9) and (ii) executioner caspases (i.e., caspases 3, 6, and 7).

Restoring cell death functionality as a therapy for cancers of the endocrine system, including ACC, is a desirable strategy, as many current therapies rely on use of the apoptosis-inducing caspase cascade. Apoptosis-inducing mechanisms in patients with different cancers, however, may not properly function, which may lead to poor patient responses to one or more therapeutics. Embodiments of the present invention provide methods that can overcome at least some of these shortcomings in the therapeutic-strategy field. The present invention provides methods of treatment that can be tailored by determining which, if any caspases, are expressed and/or methods of the present invention can be applied as a clinical assay to guide treatment decisions. Some aspects of the invention may also function as a screening model to identify new therapies with alternative modes of cellular death.

The articles, treatises, patents, references, and published patent applications described above and herein are hereby incorporated by reference in their entirety for all purposes.

SUMMARY

Embodiments of the invention provide a method of treating endocrine cancer in a subject. The method can include administering to the subject a therapeutically effective amount of a polo-like kinase 1 (PLK1) inhibitor. The method may also include administering to the subject a therapeutically effective amount of mouse double minute 2 (MDM2) inhibitor. For example, the PLK1 inhibitor can be selected from the group consisting of BI-2536, cyclapolin 9, GW 843682X, TC-S 7005, Wortmannin, NMS-P937, and GSK461364A. In particular aspects, the PLK1 inhibitor is BI-2536. In addition, the MDM2 inhibitor can be selected from the group consisting of a nutlin, caylin-1, HU 373, caylin-2, JNJ 26854165, NSC 66811, and trans-4-Indo, 4'-boranyl-chalcone. In some particular embodiments, the MDM2 is a nutlin, such as nutlin-3.

In some aspects, the endocrine cancer being treated can comprise a cancer of the adrenal gland of the subject. In one embodiment, the cancer of the adrenal gland can comprise a malignant cancer. In a preferred embodiment, the malignant adrenal gland cancer can be adrenocortical carcinoma.

In some embodiments, the PLK1 and MDM2 inhibitors can be administered as a single pharmaceutical composition that is administered to the subject as one or more single doses. In other aspects, the PLK1 and MDM2 inhibitors are administered as individual doses that can be administered at the same time, sequentially, or at any other time interval. In some embodiments, the method may also include determining if a marker having a sequence selected from the group consisting of SEQ ID NO. 3 and SEQ ID NO. 6 comprises a p53 wild type sequence in the subject being treated.

Some embodiments of the invention provide a method of treating endocrine cancer in a subject. The method may include receiving a sample of a tumor from a subject and forming a mixture. The mixture may include at least a portion of the sample and a reagent (e.g., an oligonucleotide or an antibody) that specifically binds to a first marker having a sequence selected from the group consisting of SEQ ID NO. 1, SEQ ID NO. 2, SEQ ID NO. 4, and SEQ ID No, 5. The method also includes subjecting the mixture to conditions that allow detection of binding of the reagent to the marker and then assessing an expression level of the marker in the sample based on a level of binding of the reagent to the marker. The method may also include administering a therapeutically effective amount of a pharmaceutical composition comprising a mitotic catastrophe inducing composition to the subject when the expression level of the first marker in the sample is reduced compared to a control sample. In some embodiments, the mitotic catastrophe inducing composition is a mouse double minute 2 (MDM2) inhibitor. The method may also include determining if a second marker having a sequence substantially similar a sequence selected from the group consisting of SEQ ID NO. 3 and SEQ ID NO. 6 comprises a p53 wild type sequence in the subject being treated.

In some aspects, the endocrine cancer being treated can comprise a cancer of the adrenal gland of the subject. In one embodiment, the cancer of the adrenal gland can comprise a malignant cancer. In a preferred embodiment, the malignant adrenal gland cancer can be adrenocortical carcinoma.

Embodiments of the invention provide a method of treating a subject with a caspase cascade defect. The method can include administering to the subject a therapeutically effective amount of mitotic catastrophe inducing composition to the subject. For example, the mitotic catastrophe inducing composition can comprise a PLK1 and/or an MDM2 inhibitor. For example, the PLK1 inhibitor can be selected from the group consisting of BI-2536, cyclapolin 9, GW 843682X, TC-S 7005, Wortmannin, NMS-P937, and GSK461364A. In particular aspects, the PLK1 inhibitor is BI-2536. In addition, the MDM2 inhibitor can be selected from the group consisting of a nutlin, caylin-1, HU 373, caylin-2, JNJ 26854165, NSC 66811, and trans-4-Iodo, 4'-boranyl-chalcone. In some particular embodiments, the MDM2 is a nutlin, such as nutlin-3, in some aspects, the caspase cascade defect comprises reduced expression of a first marker having a sequence selected from the group consisting of SEQ ID NO. 1, SEQ ID NO. 2, SEQ ID NO. 4, and SEQ ID NO. 5 in a sample from the subject compared to a control sample.

Additional objectives, advantages and novel features will be set forth in the description which follows or will become apparent to those skilled in the art upon examination of the drawings and detailed description which follows.

Figure 1:
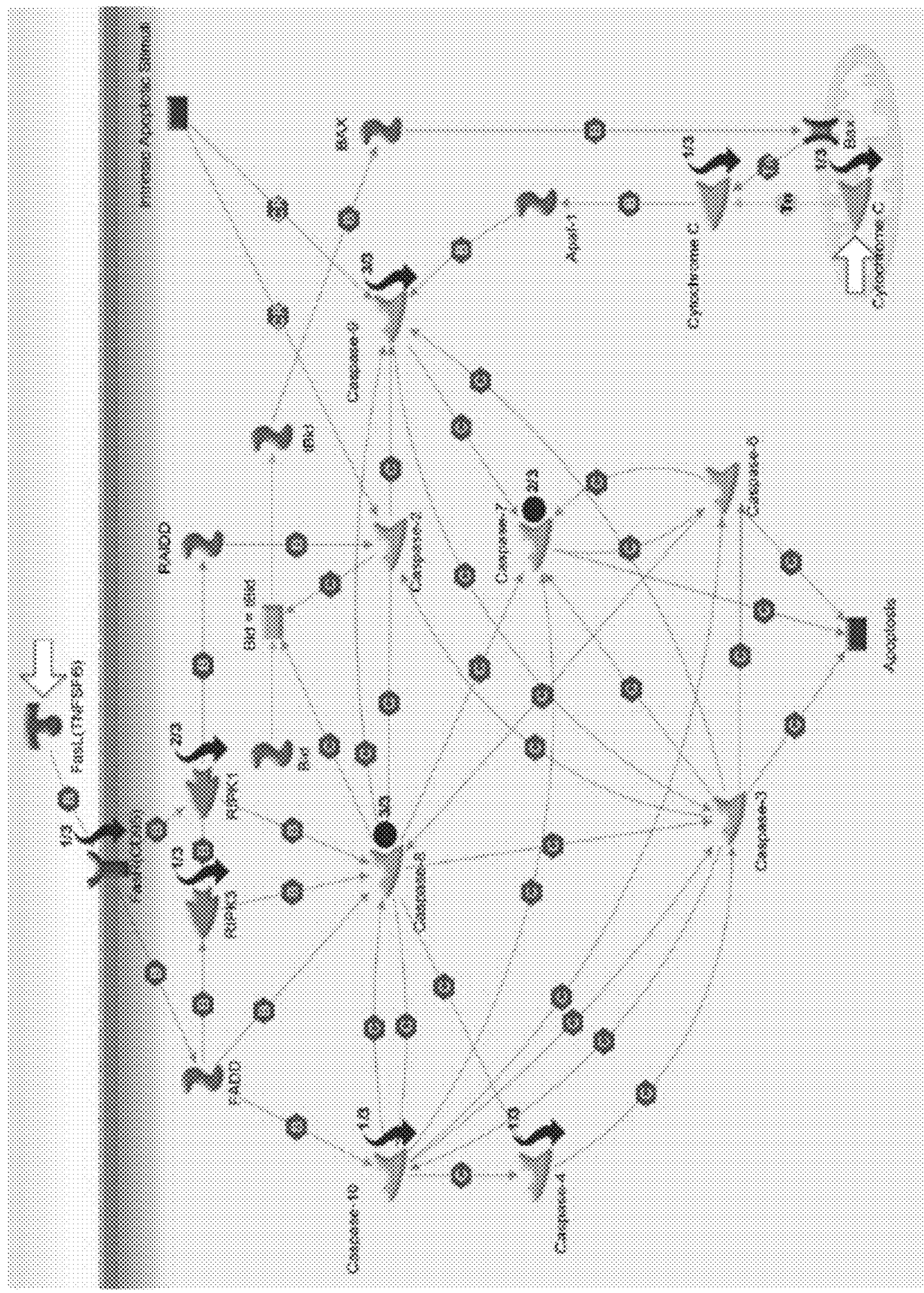
FIG. 1 is an illustration of caspase cascade defects in ACC. Integrated analysis revealed a universal under-expression of caspase 9, mutation or deletion of caspase 8, and perturbations of other parts of the pathway. Green arrows are activating changes. C=Cleavage; B=Binding; CR=complex formation; Tn=translocation between cellular compartments. Large red arrows indicate under-expression. Large red circles signify mutation or deletion events. The number of tumors affected out the total is indicated in black. This illustration was prepared using the Pathway Map Creator in MetaCore.

The headings used in the figures should not be interpreted to limit the scope of the claims.

DETAILED DESCRIPTION

Some aspects of the present invention can be used in providing treatments to subjects with cancer that exhibit one or more cellular defects. Some conventional therapeutic strategies for use by endocrine cancer patients include one or more pharmaceutical compositions that rely on cellular processes (e.g., the caspase cascade) to provide a desired outcome. For example, some therapeutic strategies rely on the intrinsic and/or extrinsic caspase cascades to trigger cell death mechanisms, including apoptosis, necroptosis, necrosis, etc. The therapeutic strategies that rely on these cellular processes, however, will be ineffective in subjects with one or more defects in the caspase cascade.

Subjects with some non-functional or malfunctioning cellular processes, including those with caspase cascade defects, can be treated using some aspects of the invention. The treatment methods may include the administration of one or more pharmaceutical compositions, alone or in combination, which can circumvent the caspase cascade defects. For example, the treatment methods provide a manner in which subjects with diseases associated with caspase cascade defects receive an efficacious treatment in spite of the defects of the caspase cascade.

Prior to treatment, some subjects or physicians treating the subjects may find it helpful to determine whether any caspase cascade defects are present within the subject. By determining the state of caspase cascade defects within the subject, appropriate therapeutic-strategy decisions can be made by the subject and/or the physician. Some aspects of the invention provide methods of assessing the expression of one or more caspases (e.g., caspases 8 and/or 9) and making therapy-related decisions based, at least in part, on the expression of these caspases. For example, a reduction in expression of some caspases indicates that a caspase cascade defect is present within the subject such that a therapy should be administered that can circumvent the caspase cascade defect.

Some embodiments of the invention may include providing one or more therapeutic strategies that can rely on mitotic catastrophe as a manner of inducing cell death in endocrine cancer. For example, mitotic catastrophe can be initiated using one or more compounds or techniques and can rely on one or more caspases that are properly functioning (e.g., caspase 2). As such, even though other initiator caspases (e.g., caspase 8 and 9) may be non-functional, treatment strategies that rely on mitotic catastrophe can circumvent the non-functional caspases by relying on caspase 2.

The present invention is directed to methods for treating one or more pathologies in a subject, including cancer. For example, methods according to some embodiments may comprise providing therapeutically effective amounts of one or more pharmaceutical compositions, alone or in combination, to the subject with cancer of the endocrine system. In some aspects, the method may include administering one or more pharmaceutical compositions, alone or in combination, that can circumvent one or more defects in normal cellular processes that may be associated with the endocrine cancer (e.g., correlated with cancer or causatively associated cancer). In particular, the administration of one or more pharmaceutical compositions may initiate one or more cellular processes that can trigger the death of one or more cells associated with the cancer. For example, the pharmaceutical compositions can trigger apoptosis, necroptosis, or any other extrinsically or intrinsically triggered cellular processes that result in the cell death or cell senescence.

Some embodiments of the invention provide methods of treating endocrine cancer in a subject, which include an assessment of one or more markers to select a treatment. The method may include assessing an expression level of the markers to make determinations regarding the operability/functionality of one or more cell processes. For example, prior to the administration of one or more pharmaceutical compositions, an assessment of the expression level of one or more initiator caspases (i.e., caspases 8 and 9) can be performed to determine whether circumvention of the initiator caspase(s) is a preferred manner of treating the subject. For example, in the event that the expression of one or more of the initiator caspases is reduced, other therapeutic strategies (i.e., induction of mitotic catastrophe) can be employed using other initiator caspases. The method may also include assessing an allelic state of the subject's p53 gene and/or protein to determine whether the subject possess a wild type or mutated form of p53.

Some embodiments of the invention provide methods of treating caspase cascade defects. The method may include initially determining whether the subject is experiencing a caspase cascade defect, which may include non-functioning or malfunctioning aspects of the apoptosis-inducing caspase cascade. For example, caspase cascade defects may include an inability of one or more initiator caspases to activate one or more executioner caspases. The method may also include administering therapeutically effective amounts of one or more pharmaceutical compositions, alone or in combination, to the subject with the caspase cascade defect. In some aspects, the method may include administering one or more pharmaceutical compositions, alone or in combination, that can circumvent the one or more caspase cascade defects. In particular, the administration of one or more pharmaceutical compositions may generally correct and/or circumvent one or more of the caspase cascade defects. For example, the pharmaceutical compositions can trigger apoptosis, necroptosis, mitotic catastrophe, or any other extrinsically or intrinsically triggered cellular processes that result in the cell death or cell senescence.

Generally, some embodiments of the present invention can be used to identify a marker and/or used to assess a level of expression of the marker. Some embodiments of the invention may also be directed to assessing a status of the marker. For example, embodiments of the invention may include determining whether a marker has a sequence (i.e., a DNA sequence, an RNA sequence, and/or a protein sequence) that is generally recognized as a wild type sequence or whether the sequence has one or more mutations therein.

A marker may be any molecular structure produced by a cell, expressed inside the cell, accessible on the cell surface, or secreted by the cell. A marker may be any protein, carbohydrate, fatty acid, nucleic acid, catalytic site, or any combination of these such as an enzyme, glycoprotein, cell membrane, virus, a particular cell, or other uni- or multimolecular structure. A marker may be represented by a sequence of a nucleic acid or any other molecules derived from the nucleic acid. Examples of such nucleic acids include miRNA, tRNA, siRNA, mRNA, cDNA, genomic DNA sequences, or complementary sequences thereof. Alternatively, a marker may be represented by a protein sequence. The concept of a marker is not limited to the exact nucleic acid sequence or protein sequence or products thereof, rather it encompasses all molecules that may be detected by a method of assessing the marker. Without being limited by the theory, the detection of the marker may encompass the detection and/or determination of a change in copy number (e.g., copy number of a gene or other forms of nucleic acid) or in the detection of one or more translocations.

Therefore, examples of molecules encompassed by a marker represented by a particular sequence further include alleles of the gene used as a marker. An allele or an allelic status includes any form of a particular nucleic acid that may be recognized as a form of the particular nucleic acid on account of its location, sequence, or any other characteristic that may identify it as being a form of the particular gene. Alleles include but need not be limited to forms of a gene that include point mutations, silent mutations, deletions, frameshift mutations, single nucleotide polymorphisms (SNPs), inversions, translocations, heterochromatic insertions, and differentially methylated sequences relative to a reference gene, whether alone or in combination. An allele of a gene may or may not produce a functional protein; may produce a protein with altered function, localization, stability, dimerization, or protein-protein interaction; may have overexpression, underexpression or no expression; may have altered temporal or spatial expression specificity; or may have altered copy number (e.g., greater or less numbers of copies of the allele). An allele may also be called a mutation or a mutant. An allele may be compared to another allele that may be termed a wild type form of an allele. In some cases, the wild type allele is more common than the mutant.

"Apoptosis" is defined as a conserved, genetically programmed form of cellular suicide characterized by distinct morphological changes such as cytoskeletal disruption, cell shrinkage, membrane blebbing, nuclear condensation, fragmentation of DNA, and loss of mitochondrial function.

"Caspase" refers to a cysteine protease of the interleukin-1β/CED-3 family. "The caspase cascade" is a sequential activation of at least two caspases, or the activation of caspase activity that behaves as if it involves the sequential activation of at least two caspases.

"Initiator caspase(s)" refers to caspase 2, caspase 8, and caspase 9, which function as the first caspases activated in the extrinsic apoptotic pathway and the intrinsic apoptotic pathways. Initiator caspases generally exist as inactive pro-caspases that are activated by dimerization rather than cleavage, unlike other caspases. Initiator caspase dimerization results from upstream signaling events and facilitates autocatalytic cleavage of initiator caspases, which results in stabilization of the dimer.

"Executioner caspase(s)" refers to caspase 3, caspase 6, and caspase 7, which function as effector caspases after activation (i.e., cleavage) by the initiator caspases. Once activated, one executioner caspase can cleave the remaining executioner caspases to irreversibly trigger the caspase cascade and apoptosis.

"Defects in the caspase cascade" or "caspase cascade defects" refer to an inability of one or more of the initiator caspases to activate the executioner caspases. The caspase cascade defects may occur due to reduced or non-detectable expression of the initiator caspases. The defects may arise because of one or more mutations in the nucleotide (e.g., DNA or RNA) sequence or the amino acid sequence of the initiator caspase(s) protein. Moreover, the defects may also arise due to post-translational changes in the initiator caspase(s) protein. Caspase cascade defects can result in one or more pathological states, including cancer and other proliferative disorders. Caspase cascade defects may be assessed using any of the techniques described below. In some embodiments, two of the initiator caspases may be non-functional (i.e., through mutation and/or reduced expression) such that only one other initiator caspase can function to activate the caspase cascade. For example, in the event that one or more of the initiator caspases are non-functional, activation of one of the functional initiator caspases can be achieved to provide activation of the caspase cascade.

By way of example only, some embodiments may provide assessing an expression level of a marker, such as caspase 8 or caspase 9. The invention includes determining the expression of these markers using one or more molecular techniques described herein or known to those having skill in the art. Moreover, the invention may provide methods for determining whether the cells of a subject contain at least one mutation in the p53 gene or protein. The invention may further include testing for at least one mutation in the p53 gene or protein using tests that are well known to those of ordinary skill in the art. For example, see Flaman, J.-M. et al., *Proc. Natl. Acad. Sci. USA* 92: 3963-3967 (1995). In one embodiment, the mutation(s) are detected by direct sequencing of the gene or the protein. In another embodiment, the mutation(s) are detected by PCR.

In a particular embodiment of the invention that relates to the treatment of endocrine cancers, the cancer can be identified as p53 wild type (p53WT). In another aspect, the present invention provides a diagnostic for determining which patients should be administered a treatment according to some embodiments of the invention. For example, a sample from a patient/subject may be taken and analyzed to determine the allelic status of the sample (e.g., cancer cells) with respect to p53. In one aspect, a patient having a cancer that is p53WT will be selected for treatment. In another aspect, a patient having a cancer that has p53WT protein is selected over a patient that does not have these characteristics. The taking of cancer cells for analyses is well known to those skilled in the art. The term "p53WT" or "p53 wild type" means a protein encoded by a nucleic acid sequence that is substantially similar to the sequence of SEQ ID NO. 3 or a protein comprising an amino acid sequence that is substantially similar to the amino acid sequence of SEQ ID NO. 6.

The term "mitosis" refers to the generally accepted theory of eukaryotic cellular growth. Mitosis is the process of the cell cycle by which a cell duplicates into two generally genetically identical daughter cells. In general, during mitosis, chromosomes in the nucleus are replicated and separated into two sets of chromosomes, each having its own nucleus. Successful mitosis is generally followed by cytokinesis, which divides cellular constituents into two daughter cells.

The term "mitotic catastrophe" is method of cell death that refers to a mechanism to prevent genomic instability in response to DNA damage or perturbations to cellular components during mitosis. The perturbations could include damage to the chromosomes or the cellular components that function to replicate and/or segregate the chromosomes during mitosis. In addition, the accumulation of unrepaired DNA damage (e.g., mutations, amplifications, deletions, SNPs, etc.) may also trigger mitotic catastrophe. See R. Mu et al., *Depletion of pre-mRNA splicing factor Cdc5L inhibits mitotic progression and triggers mitotic catastrophe*, Cell Death and Disease (5) e1151 (2014). In particular, mitotic catastrophe can be characterized by the occurrence of aberrant mitosis or the missegregation of the chromosomes followed by cell division. Mitotic catastrophe can function as an innate oncosuprresive mechanism or a mechanism that is triggered by one or more mitotic catastrophe-inducing agents. For example, mitotic catastrophe is one of the modes of cell death following treatment with ionizing radiation and can occur in response to other pharmaceutical compositions. See D. Morse et al., *Docetaxel induces cell death through mitotic catastrophe in human breast cancer cells*, Molecular Cancer Therapies (10) 1495 (2005).

Mitotic catastrophe can occur via the caspase cascade. In particular, one or more of the initiator caspases can be activated in mitotic catastrophe to trigger cell death (e.g., apoptosis). In a particular embodiment, caspase 2 can be activated to trigger the caspase cascade to lead to cell death, which may include apoptosis.

The term "derived from" refers to the origin or source, and may include naturally occurring, recombinant, unpurified, or purified molecules. The proteins and molecules of the present invention may be derived from human or non-human molecules.

The term "nucleic acid" refers to a polymeric form of nucleotides of any length, either ribonucleotides or deoxyribonucleotides, or analogs thereof. This term refers to the primary structure of the molecule, and thus includes double and single-stranded DNA, as well as double- and single-stranded RNA. It also includes modified nucleic acids such as methylated and/or capped nucleic acids, nucleic acids containing modified bases, backbone modifications, and the like. The terms "nucleic acid" and "nucleotide sequence" are used interchangeably. In some particular aspects of the invention, caspase 8 comprises the nucleotide sequence of SEQ ID NO. 1, caspase 9 comprises the nucleotide sequence of SEQ ID NO. 2, and p53 comprises the nucleotide sequence of SEQ ID NO. 3.

The term "gene" refers to a nucleic acid or portion of a nucleic acid comprising a sequence that encodes a protein. It is understood in the art that a gene also comprises non-coding sequences, such as 5' and 3' flanking sequences (such as promoters, enhancers, repressors, and other regulatory sequences) as well as introns.

The terms "polynucleotide", "polynucleotide sequence", "nucleic acid sequence", "nucleic acid fragment", and "isolated nucleic acid fragment" are used interchangeably herein. These terms encompass nucleotide sequences and the like. A polynucleotide may be a polymer of RNA or DNA that is single- or double-stranded, that optionally contains synthetic, non-natural or altered nucleotide bases. A polynucleotide in the form of a polymer of DNA may be comprised of one or more segments of cDNA, genomic DNA, synthetic DNA, or mixtures thereof. Nucleotides (usually found in their 5'-monophosphate form) are referred to by a single letter designation as follows: "A" for adenylate or deoxyadenylate (for RNA or DNA, respectively), "C" for cytidylate or deoxycytidylate, "G" for guanylate or deoxyguanylate, "U" for uridylate, "T" for deoxythymidylate, "R" for purines (A or G), "Y" for pyrimidines (C or T), "K" for G or T, "H" for A or C or T, "I" for inosine, and "N" for any nucleotide.

The terms "polypeptide," "peptide," and "protein" are used interchangeably herein to refer to polymers of amino acids of any length. These terms also include proteins that are post-translationally modified through reactions that include glycosylation, acetylation and phosphorylation. In some particular aspects of the invention, caspase 8 comprises the amino acid sequence of SEQ ID NO. 4, caspase 9 comprises the amino acid sequence of SEQ ID NO. 5, and p53 comprises the nucleotide sequence of SEQ ID NO. 6.

The term "nucleotide" is defined as a modified or naturally occurring deoxyribonucleotide or ribonucleotide. Nucleotides typically include purines and pyrimidines, which include thymidine, cytidine, guanosine, adenine and uridine.

The term "at least a portion" of a nucleic acid or polypeptide means a portion having the minimal size characteristics of such sequences, or any larger fragment of the full length molecule, up to and including the full length molecule. For example, a portion of a nucleic acid may be 12 nucleotides, 13 nucleotides, 14 nucleotides, 15 nucleotides, 16 nucleotides, 17 nucleotides, 18 nucleotides, 19 nucleotides, 20 nucleotides, 22 nucleotides, 24 nucleotides, 26 nucleotides, 28 nucleotides, 30 nucleotides, 32 nucleotides, 34 nucleotides, 36 nucleotides, 38 nucleotides, 40 nucleotides, 45 nucleotides, 50 nucleotides, 55 nucleotides, and so on, going up to the full length nucleic acid. Similarly, a portion of a polypeptide may be 4 amino acids, 5 amino acids, 6 amino acids, 7 amino acids, and so on, going up to the full length polypeptide. The length of the portion to be used will depend on the particular application. A portion of a nucleic acid useful as hybridization probe may be as short as 12 nucleotides; in one embodiment, it is 20 nucleotides. A portion of a polypeptide useful as an epitope may be as short as 4 amino acids. A portion of a polypeptide that performs the function of the full-length polypeptide would generally be longer than 4 amino acids.

Determination of marker expression may be performed by one or more of the methods known to one of ordinary skill in the art. For example, gene expression levels may be determined by detection of (a) a polypeptide encoded by a marker gene, (b) mRNA encoding a marker protein or marker polypeptide, (c) a portion of DNA which constitutes a marker gene, or (d) any combination thereof.

Levels of marker expression can be detected, for example, by measuring levels of protein using specific binding compositions. The detection of protein levels may be carried out using any of the methods known to one of ordinary skill in the art including, but not limited to, chemiluminescence methods, histochemical staining or biochemical detection (i.e., immuno-histochemistry assays), Western Blot analysis, flow cytometry, immuno-precipitation (or the equivalent thereof for non-antibody agents), Plasmon resonance absorbance measurement, and the like. In one embodiment of the invention, the method of detecting protein levels is an immunoassay (such as an ELISA), which includes the use of at least one antibody. In yet another embodiment of the invention, protein staining, in tissue sample for example, formalin-fixed, paraffin-embedded tissue sections can be carried out by immunohistochemistry using an antibody, and determining the expression of the gene.

One embodiment of the invention is performed using an IHC kit which uses a primary mouse monoclonal antibody, a secondary anti-mouse IgG antibody, a peroxidase blocker to quench the endogenous peroxidase activity and a chromogenic substrate. Measurement of the polypeptide encoded by a marker may include measurements of fragments of the polypeptide, wherein the fragments arise from transcriptional or translational variants of the marker; or alternatively, differently sized polypeptides arise as a result of post translational modifications including proteolysis of a larger portion of a polypeptide.

Detection of levels of mRNA may also serve as an indicator of marker expression. The methods used to detect mRNA levels are well known in the art, and include, for example, the detection of hybridization or amplification with the mRNA encoding a gene product. This detection may be carried out by analysis of mRNA either in vitro or in situ (e.g., in a tissue sample) using one of the methods known to one of ordinary skill in the art as exemplified in the Current Protocols in Molecular Biology (John Wiley & Sons, 1999); in U.S. Pat. No. 5,882,864; and the like. An mRNA detected will be any RNA transcript of a specific gene, or fragment thereof.

Some embodiments of the invention may include assessing, determining, quantifying, or altering the expression of a marker. As used herein, expression encompasses any and all processes through which material derived from a nucleic acid template may be produced. Expression thus includes RNA transcription, mRNA splicing, protein translation, protein folding, post-translational modification, membrane transport, associations with other molecules, addition of carbohydrate moieties to proteins, phosphorylation, protein complex formation and any other process along a continuum that results in biological material derived from genetic material. Expression also encompasses all processes through which the production of material derived from a nucleic acid template may be actively or passively suppressed. Such processes include all aspects of transcriptional and translational regulation. Examples include heterochromatic silencing, transcription factor inhibition, any form of RNAi silencing, microRNA silencing, small interfering RNA silencing, alternative splicing, protease digestion, posttranslational modification, and alternative protein folding.

Expression may be assessed by any number of methods used to detect material derived from a nucleic acid template used currently in the art and yet to be developed. Examples of such methods include any nucleic acid detection method including the following nonlimiting examples, microarray analysis, RNA in situ hybridization, RNAse protection assay, Northern blot, reverse transcriptase PCR, quantitative PCR, quantitative reverse transcriptase PCR, quantitative real-time reverse transcriptase PCR, reverse transcriptase treatment followed by direct sequencing, or any other method of detecting a specific nucleic acid now known or yet to be disclosed. Other examples include any process of assessing expression that uses an antibody including the following nonlimiting examples, flow cytometry, immunohistochemistry, ELISA, Western blot, and immunoaffinity chromatography. Antibodies may be monoclonal, polyclonal, or any antibody fragment including an Fab, F(ab)2, Fv, scFv, phage display antibody, peptibody, multispecific ligand, or any other reagent with specific binding to a marker. Such methods also include direct methods used to assess protein expression including the following non-limiting examples: HPLC, mass spectrometry, protein microarray analysis, PAGE analysis, isoelectric focusing, 2-D gel electrophoresis, and enzymatic assays. Samples from which expression may be detected include single cells, whole organs or any fraction of a whole organ, whether in vitro, ex vivo, in vivo, or post-mortem.

Other methods used to assess expression include the use of natural or artificial ligands capable of specifically binding one or more markers, including a protein, carbohydrate, fat, nucleic acid, catalytic site, or any combination of these such as an enzyme, glycoprotein, cell membrane, virus, cell, organ, organelle, or any uni- or multimolecular structure that constitutes a marker that may be specifically bound by a ligand. Such ligands include antibodies, antibody complexes, conjugates, natural ligands, small molecules, nanoparticles, or any other molecular entity capable of specific binding to a marker. Ligands may be associated with a label such as a radioactive isotope or chelate thereof, dye (fluorescent or non-fluorescent) stain, enzyme, metal, or any other substance capable of aiding a machine or a human eye from differentiating a cell expressing a marker from a cell not expressing a marker. Additionally, expression may be assessed by monomeric or multimeric ligands associated with substances capable of killing the cell. Such substances include protein or small molecule toxins, cytokines, pro-apoptotic substances, pore forming substances, radioactive isotopes, or any other substance capable of killing a cell.

Positive expression encompasses any difference between a cell expressing markers and a cell that does not express one or more of the markers. The exact nature of positive expression varies by the method, but is well known to those skilled in the art of practicing a particular method. Positive expression may be assessed by a detector, an instrument containing a detector, or by aided or unaided human eye. Examples include but are not limited to specific staining of cells expressing a target in an IHC slide, binding of RNA from a sample to a microarray and detection of binding through the use of said microarray, a particular rate of dye incorporation in real-time RT-PCR measured in ΔCt or alternatively in the number of PCR cycles necessary to reach a particular optical density at a wavelength at which a double stranded DNA binding dye (e.g., SYBR Green) incorporates, through release of label from a previously labeled reporter probe used in a real-time RT-PCR reaction, detection of fluorescence on a cell expressing a target by a flow cytometer, the presence of radiolabeled bands on film in a Northern blot, detection of labeled blocked RNA by RNAse protection assay, cell death measured by apoptotic markers, cell death measured by shrinkage of a tumor, or any other signal for the expression of a marker in existence now or yet to be developed.

Reduced expression encompasses any reduction (i.e., partial or complete reduction) in the expression of one or more markers on or in a cell from a subject relative to the expression of the same markers in or on any other cell (e.g., a control cell). In some aspects of the invention, reduced expression includes no detectable expression. However, the concept of reduced expression further encompasses insufficient expression to reach or exceed a threshold, cutoff, or level that has been previously shown to result in a particular cellular or physiological response. Reduced expression may include similar expression relative to a control that has been previously determined not to express the marker(s) or similar expression to a control that has been previously determined not to exhibit the response. In this case, even though expression may be detectable, it still constitutes reduced expression. In some aspects of the invention, an expression level of a marker in a control known to have a reduced or increase risk of recurrence is predetermined and expression similar to that level is correlated with reduced or increase risk of recurrence. Increased or reduced expression includes expression that is 75% 50%, 25%, 10%, 5%, 1%, 0.1%, greater or less of that of a control cell or a median level of expression in a population. Reduced expression may also include greater than or less than $1\times10^{-5}$ greater or less expression normalized to the expression of a housekeeping gene.

Assessing the risk of a particular disease outcome includes the performing of any type of test, assay, examination, result, readout, or interpretation that correlates with an increased or decreased probability that an individual has had, currently has, or will develop a particular disease, disorder, symptom, syndrome, or any condition related to health or bodily state. Examples of disease outcomes include, but need not be limited to survival, death, progression of existing disease, remission of existing disease, initiation of onset of a disease in an otherwise disease-free subject, or the continued lack of disease in a subject in which there has been a remission of disease. Assessing the risk of a particular disease encompasses diagnosis in which the type of disease afflicting a subject is determined. Assessing the risk of a disease outcome also encompasses the concept of prognosis. A prognosis may be any assessment of the risk of disease outcome in an individual in which a particular disease has been diagnosed. Assessing the risk further encompasses prediction of therapeutic response in which a treatment regimen is chosen based on the assessment. Assessing the risk also encompasses a prediction of overall survival after diagnosis.

Some embodiments of the invention may comprise the use of one or more methods of amplifying a nucleic acid-based starting material (i.e., a template). Nucleic acids may be selectively and specifically amplified from a template nucleic acid contained in a sample. In some nucleic acid amplification methods, the copies are generated exponentially. Examples of nucleic acid amplification methods known in the art include: polymerase chain reaction (PCR), ligase chain reaction (LCR), self-sustained sequence replication (3SR), nucleic acid sequence based amplification (NASBA), strand displacement amplification (SDA), amplification with Qβ replicase, whole genome amplification with enzymes such as ϕ29, whole genome PCR, in vitro transcription with T7 RNA polymerase or any other RNA polymerase, or any other method by which copies of a desired sequence are generated.

An oligonucleotide may be any polynucleotide of at least 2 nucleotides. Oligonucleotides may be less than 10, 15, 20, 30, 40, 50, 75, 100, 200, or 500 nucleotides in length. While oligonucleotides are often linear, they may assume a circular or other two dimensional structure. Oligonucleotides may be chemically synthesized by any of a number of methods including sequential synthesis, solid phase synthesis, or any other synthesis method now known or yet to be disclosed. Alternatively, oligonucleotides may be produced by recombinant DNA based methods. In some aspects of the invention, an oligonucleotide may be 2 to 1000 bases in length. In other aspects, it may be 5 to 500 bases in length, 5 to 100 bases in length, 5 to 50 bases in length, or 10 to 30 bases in length. One skilled in the art would understand the length of oligonucleotide necessary to perform a particular task. Oligonucleotides may be directly labeled, used as primers in PCR or sequencing reactions, or bound directly to a solid substrate as in oligonucleotide arrays.

In addition to genomic DNA, any oligonucleotide or polynucleotide sequence can be amplified with an appropriate set of primer molecules. In particular, the amplified segments created by the PCR process itself are, themselves, efficient templates for subsequent PCR amplifications.

PCR generally involves the mixing of a nucleic acid sample, two or more primers that are designed to recognize the template DNA, a DNA polymerase, which may be a thermostable DNA polymerase such as Taq or Pfu, and deoxyribose nucleoside triphosphates (dNTP's). Reverse transcription PCR, quantitative reverse transcription PCR, and quantitative real time reverse transcription PCR are other specific examples of PCR. In general, the reaction mixture is subjected to temperature cycles comprising a denaturation stage (typically 80-100° C.), an annealing stage with a temperature that is selected based on the melting temperature (Tm) of the primers and the degeneracy of the primers, and an extension stage (for example 40-75° C.). In real-time PCR analysis, additional reagents, methods, optical detection systems, and devices known in the art are used that allow a measurement of the magnitude of fluorescence in proportion to concentration of amplified DNA. In such analyses, incorporation of fluorescent dye into the amplified strands may be detected or measured.

Alternatively, labeled probes that bind to a specific sequence during the annealing phase of the PCR may be used with primers. Labeled probes release their fluorescent tags during the extension phase so that the fluorescence level may be detected or measured. Generally, probes are complementary to a sequence within the target sequence downstream from either the upstream or downstream primer. Probes may include one or more label. A label may be any substance capable of aiding a machine, detector, sensor, device, or enhanced or unenhanced human eye from differentiating a labeled composition from an unlabeled composition. Examples of labels include but are not limited to: a radioactive isotope or chelate thereof, dye (fluorescent or nonfluorescent,) stain, enzyme, or nonradioactive metal. Specific examples include, but are not limited to: fluorescein, biotin, digoxigenin, alkaline phosphatese, biotin, streptavidin, $^{3}H$, $^{14}C$, $^{32}F$, $^{35}S$, or any other compound capable of emitting radiation, rhodamine, 4-(4'-dimethylamino-phenylazo)benzoic acid ("Dabcyl"); 4-(4'-dimethylamino-phenylazo)sulfonic acid (sulfonyl chloride) ("Dabsyl"); 5-((2-aminoethyl)-amino)-naphtalene-1-sulfonic acid ("EDANS"); Psoralene derivatives, haptens, cyanines, acridines, fluorescent rhodol derivatives, cholesterol derivatives; ethylenediaminetetraaceticacid ("EDTA") and derivatives thereof or any other compound that may be differentially detected. The label may also include one or more fluorescent dyes optimized for use in genotyping. Examples of dyes facilitating the reading of the target amplification include, but are not limited to: CAL-Fluor Red 610, CAL-Fluor Orange 560, dR110, 5-FAM, 6FAM, dR6G, JOE, HEX, VIC, TET, dTAMRA, TAMRA, NED, dROX, PET, BHQ+, Gold540, and LIZ.PCR facilitating the reading of the target amplification.

Either primers or primers along with probes allow a quantification of the amount of specific template DNA present in the initial sample. In addition, RNA may be detected by PCR analysis by first creating a DNA template from RNA through a reverse transcriptase enzyme. The marker expression may be detected by quantitative PCR analysis facilitating genotyping analysis of the samples.

An illustrative example, using dual-labeled oligonucleotide probes in PCR reactions is disclosed in U.S. Pat. No. 5,716,784 to DiCesare. In one example of the PCR step of the multiplex Real Time-PCR/PCR reaction of the present invention, the dual-labeled fluorescent oligonucleotide probe binds to the target nucleic acid between the flanking oligonucleotide primers during the annealing step of the PCR reaction. The 5' end of the oligonucleotide probe contains the energy transfer donor fluorophore (reporter fluor) and the 3' end contains the energy transfer acceptor fluorophore (quenching fluor). In the intact oligonucleotide probe, the 3' quenching fluor quenches the fluorescence of the 5' reporter fluor. However, when the oligonucleotide probe is bound to the target nucleic acid, the 5' to 3' exonuclease activity of the DNA polymerase, e.g., Taq DNA polymerase, will effectively digest the bound labeled oligonucleotide probe during the amplification step. Digestion of the oligonucleotide probe separates the 5' reporter fluor from the blocking effect of the 3' quenching fluor. The appearance of fluorescence by the reporter fluor is detected and monitored during the reaction, and the amount of detected fluorescence is proportional to the amount of fluorescent product released. Examples of apparatus suitable for detection include, e.g. Applied Biosystems™ 7900HT real-time PCR platform and Roche's 480 LightCycler, the ABI Prism 7700 sequence detector using 96-well reaction plates or GENEAMP PC System 9600 or 9700 in 9600 emulation mode followed by analysis in the ABA Prism Sequence Detector or TAQMAN LS-50B PCR Detection System. The labeled probe facilitated multiplex Real Time-PCR/PCR can also be performed in other real-time PCR systems with multiplexing capabilities.

"Amplification" is a special case of nucleic acid replication involving template specificity. Amplification may be a template-specific replication or a non-template-specific replication (i.e., replication may be specific template-dependent or not). Template specificity is here distinguished from fidelity of replication (synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques have been designed primarily for this sorting out.

The term "template" refers to nucleic acid originating from a sample that is analyzed for the presence of a molecule of interest. In contrast, "background template" or "control" is used in reference to nucleic acid other than sample template that may or may not be present in a sample. Background template is most often inadvertent. It may be the result of carryover, or it may be due to the presence of nucleic acid contaminants sought to be purified out of the sample. For example, nucleic acids from organisms other than those to be detected may be present as background in a test sample.

In addition to primers and probes, template specificity is also achieved in some amplification techniques by the choice of enzyme. Amplification enzymes are enzymes that, under the conditions in which they are used, will process only specific sequences of nucleic acid in a heterogeneous mixture of nucleic acid. Other nucleic acid sequences will not be replicated by this amplification enzyme. Similarly, in the case of T7 RNA polymerase, this amplification enzyme has a stringent specificity for its own promoters (Chamberlin et al. (1970) Nature (228):227). In the case of T4 DNA ligase, the enzyme will not ligate the two oligonucleotides or polynucleotides, where there is a mismatch between the oligonucleotide or polynucleotide substrate and the template at the ligation junction (Wu and Wallace (1989) Genomics (4):560). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.) (1989) PCR Technology, Stockton Press).

The term "amplifiable nucleic acid" refers to nucleic acids that may be amplified by any amplification method. It is contemplated that "amplifiable nucleic acid" will usually comprise "sample template." The terms "PCR product," "FOR fragment," and "amplification product" refer to the resultant mixture of compounds after two or more cycles of the PCR steps of denaturation, annealing and extension. These terms encompass the case where there has been amplification of one or more segments of one or more target sequences.

In some forms of PCR assays, quantification of a target in an unknown sample is often required. Such quantification is often in reference to the quantity of a control sample. The control sample DNA may be co-amplified in the same tube in a multiplex assay or may be amplified in a separate tube. Generally, the control sample contains DNA at a known concentration. The control sample DNA may be a plasmid construct comprising only one copy of the amplification region to be used as quantification reference. To calculate the quantity of a target in an unknown sample, various mathematical models are established. Calculations are based on the comparison of the distinct cycle determined by various methods, e.g., crossing points (CP) and cycle threshold values (Ct) at a constant level of fluorescence; or CP acquisition according to established mathematic algorithm.

The algorithm for Ct values in real time-PCR calculates the cycle at which each PCR amplification reaches a significant threshold. The calculated Ct value is proportional to the number of target copies present in the sample, and the Ct value is a precise quantitative measurement of the copies of the target found in any sample. In other words, Ct values represent the presence of respective target that the primer sets are designed to recognize. If the target is missing in a sample, there should be no amplification in the Real Time-PCR reaction.

Alternatively, the Cp value may be utilized. A Cp value represents the cycle at which the increase of fluorescence is highest and where the logarithmic phase of a PCR begins. The LightCycler® 480 Software calculates the second derivatives of entire amplification curves and determines where this value is at its maximum. By using the second-derivative algorithm, data obtained are more reliable and reproducible, even if fluorescence is relatively low.

The various and non-limiting embodiments of the PCR-based method detecting marker expression level as described herein may comprise one or more probes and/or primers. Generally, the probe or primer contains a sequence complementary to a sequence specific to a region of the nucleic acid of the marker gene. A sequence having less than 60% 70%, 80%, 90%, 95%, 99% or 100% identity to the identified gene sequence may also be used for probe or primer design if it is capable of binding to its complementary sequence of the desired target sequence in marker nucleic acid.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The sample in this method is preferably a biological sample from a subject. The term "sample" or "biological sample" is used in its broadest sense. Depending upon the embodiment of the invention, for example, a sample may comprise a bodily fluid including whole blood, serum, plasma, urine, saliva, cerebral spinal fluid, semen, vaginal fluid, pulmonary fluid, tears, perspiration, mucus and the like; an extract from a cell, chromosome, organelle, or membrane isolated from a cell; a cell; genomic DNA, RNA, or cDNA, in solution or bound to a substrate; a tissue; a tissue print, or any other material isolated in whole or in part from a living subject. Biological samples may also include sections of tissues such as biopsy and autopsy samples, and frozen sections taken for histologic purposes such as blood, plasma, serum, muscle, sputum, stool, tears, mucus, hair, skin, and the like. Biological samples also include explants and primary and/or transformed cell cultures derived from patient tissues. In some embodiments, the sample can comprise tissue obtained from an adrenal cortex of a subject, including a living or a deceased subject.

Some embodiments of the invention may include a method of comparing a marker in a sample relative to one or more control samples. A control may be any sample with a previously determined level of expression. A control may comprise material within the sample or material from sources other than the sample. Alternatively, the expression of a marker in a sample may be compared to a control that has a level of expression predetermined to signal or not signal a cellular or physiological characteristic. This level of expression may be derived from a single source of material including the sample itself or from a set of sources.

The invention may further comprise sequencing nucleic adds from a sample, including sequencing a subject's entire genome, exome, or transcriptome. Methods of sequencing include but need not be limited to any form of DNA sequencing including Sanger, next-generation sequencing, pyrosequencing, SOLiD sequencing, massively parallel sequencing, pooled, and barcoded DNA sequencing or any other sequencing method now known or yet to be disclosed.

In Sanger Sequencing, a single-stranded DNA template, a primer, a DNA polymerase, nucleotides and a label such as a radioactive label conjugated with the nucleotide base or a fluorescent label conjugated to the primer, and one chain terminator base comprising a dideoxynucleotide (ddATP, ddGTP, ddCTP, or ddTTP), are added to each of four reaction (one reaction for each of the chain terminator bases). The sequence may be determined by electrophoresis of the resulting strands. In dye terminator sequencing, each of the chain termination bases is labeled with a fluorescent label of a different wavelength that allows the sequencing to be performed in a single reaction.

In pyrosequencing, the addition of a base to a single-stranded template to be sequenced by a polymerase results in the release of a pyrophosphate upon nucleotide incorporation. An ATP sulfuryrlase enzyme converts pyrophosphate into ATP that in turn catalyzes the conversion of luciferin to oxyluciferin which results in the generation of visible light that is then detected by a camera or other sensor capable of capturing visible light.

In SOLiD sequencing, the molecule to be sequenced is fragmented and used to prepare a population of clonal magnetic beads (in which each bead is conjugated to a plurality of copies of a single fragment) with an adaptor sequence and alternatively a barcode sequence. The beads are bound to a glass surface. Sequencing is then performed through 2-base encoding.

In massively parallel sequencing, randomly fragmented targeted DNA is attached to a surface. The fragments are extended and bridge amplified to create clusters, each with a plurality of copies of a single fragment sequence, within flow cell lanes. The templates are sequenced by synthesizing the fragments in parallel. Bases are indicated by the release of a fluorescent dye correlating to the addition of the particular base to the fragment. Nucleic acid sequences may be identified by the IUAPC letter code which is as follows: A—Adenine base; C—Cytosine base; G—guanine base; T or U thymine or uracil base. M-A or R-A or G; W-A or T; S-C or G; C or T; K-G or T; V-A or C or G; H-A or C or T; D-A or G or T; B-C or G or T; N or X-A or C or G or T. Note that T or U may be used interchangeably depending on whether the nucleic acid is DNA or RNA. A sequence having less than 60%, 70%, 80%, 90%, 95%, 99% or 100% identity to the identifying sequence may still be encompassed by the invention if it is able of binding to its complimentary sequence and/or facilitating nucleic acid amplification of a desired target sequence. In some embodiments, the method may include the use of massively parallel sequencing, as detailed in U.S. Pat. Nos. 8,431,348 and 7,754,429, which are hereby incorporated by reference in their entirety.

Cancer cells include any cells derived from a tumor, neoplasm, cancer, precancer, cell line, malignancy, or any other source of cells that have the potential to expand and grow to an unlimited degree. Cancer cells may be derived from naturally occurring sources or may be artificially created. Cancer cells may also be capable of invasion into other tissues and metastasis. Cancer cells further encompass any malignant cells that have invaded other tissues and/or metastasized. One or more cancer cells in the context of an organism may also be called a cancer, tumor, neoplasm, growth, malignancy, or any other term used in the art to describe cells in a cancerous state.

Examples of cancers that could serve as sources of cancer cells include solid tumors such as fibrosarcoma, myxosarcoma, liposarcoma, chondrosarcoma, osteogenic sarcoma, chordoma, angiosarcoma, endothelio sarcoma, lymphangiosarcoma, lymphangioendothelio sarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cyatadenocarcinoma, medullary carcinoma, bronchogenic carcinoma, renal cell carcinoma, hepatoma, bile duct carcinoma, choriocarcinoma, seminoma, embryonal carcinoma. Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma.

Additional cancers that may serve as sources of cancer cells include blood borne cancer, such as acute lymphoblastic leukemia ("ALL,"), acute lymphoblastic B-cell leukemia, acute lymphoblastic T-cell leukemia, acute myeloblastic leukemia ("AML"), acute promyelocytic leukemia ("APL"), acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia ("CML"), chronic lymphocytic leukemia ("CLL"), hairy cell leukemia, multiple myeloma, lymphoblastic leukemia, myelogenous leukemia, lymphocytic leukemia, myelocytic leukemia, Hodgkin's disease, non-Hodgkin's Lymphoma, Waldenstrom's macroglobulinemia, Heavy chain disease, and Polycythemia vera.

In some embodiments, cancer may comprise a cancer of the endocrine system of the subject. For example, the endocrine cancer can comprise a cancer of an adrenal gland of the subject. In some embodiments, the adrenal gland cancer can be a malignant cancer. In a preferred embodiment, the malignant adrenal gland cancer can be adrenocortical carcinoma.

The term "endocrine system" refers to a subject's collection of glands, tissues, cells, and other bodies and organs within the animal that produce and/or secrete hormones. The endocrine system includes adrenal glands, the hypothalamus, ovaries, testicles, pancreas, parathyroid glands, pineal body, pituitary gland, thymus gland, and thyroid gland. Moreover, "cancer of the endocrine system" or "endocrine cancer" refers to partially or completely unregulated growth of one or more cellular components of the endocrine system. For example, endocrine cancers can include a cancer of one or more of the adrenal glands, carcinoid tumors, parathyroid tumors, pituitary gland tumors, and thyroid tumors.

Some endocrine cancers, such as a cancer of the adrenal gland may comprise a malignant cancer or a benign cancer. The term "malignant" refers to a type of cancer that has the potential to invade and/or damage proximal or distal tissues and organs. Malignant also includes the ability to metastasize or separate/detach from an initial site of cancerous growth, enter a circulatory and/or a lymphatic system of an animal, and form additional cancerous growths in other locations within the animal. The term "benign" refers to a type of cancer that generally does not metastasize to other locations within the animal. For example, malignant cancer of the adrenal gland can be adrenocortical carcinoma.

The term "PLK1-mediated condition", "polo-like kinase 1 mediated disorder" or any other variation thereof, as used herein means any disease or other condition in which PLK1 is known to play a role, or a disease state that is associated with elevated activity or expression of PLK1. For example, a "PLK1-mediated condition" may be relieved by inhibiting PLK1 activity. Such conditions include various cancers, including bladder, thyroid, ovarian, pancreatic, breast, endometrial, prostate, colorectal, lung (e.g. non-small cell lung cancer), head and neck, gastric, oropharyngeal, and esophageal cancers, glioma, glioblastoma, papillary carcinoma, hepatoma, melanoma, lymphomas (e.g. non-Hodgkins lymphoma, Hodgkin's lymphoma), leukemias (e.g. chronic myeloid leukemia, acute myeloid leukemia), adrenocortical carcinoma, advanced metastatic cancers, and advanced solid tumors.

The term "subject" is used in its broadest sense. "Subject" may also be used interchangeably with the term "patient." In a preferred embodiment, the subject is a mammal. Non-limiting examples of mammals include humans, dogs, cats, horses, cows, sheep, goats, and pigs. Preferably, a subject includes any human or non-human mammal, including for example: a primate, cow, horse, pig, sheep, goat, dog, cat, or rodent, capable of developing cancer including human patients that are suspected of having cancer, that have been diagnosed with cancer, or that have a family history of cancer (e.g., adrenocortical carcinoma).

Some embodiments of the invention may include the administration of a pharmaceutical composition or more than one pharmacological composition to a subject that has been diagnosed with cancer. Such pharmaceutical compositions may take any physical form necessary depending on a number of factors including the desired method of administration and the physicochemical and stereochemical form taken by the compound or pharmaceutically acceptable salts of the compound. Such physical forms include a solid, liquid, gas, sol, gel, aerosol, or any other physical form now known or yet to be disclosed.

The concept of a pharmaceutical composition encompasses a compound or a pharmaceutically acceptable salt thereof with or without any other additive. The physical form of the invention may affect the route of administration and one skilled in the art would know to choose a route of administration that takes into consideration both the physical form of the compound and the disorder to be treated. Pharmaceutical compositions that include the compound may be prepared using methodology well known in the pharmaceutical art. A pharmaceutical composition that includes the disclosed compound may include a second effective compound of a distinct chemical formula from the disclosed compound. This second effective compound may have the same or a similar molecular target as the target or it may act upstream or downstream of the molecular target of the compound with regard to one or more biochemical pathways.

Pharmaceutical compositions include materials capable of modifying the physical form of a dosage unit. In one non-limiting example, the composition includes a material that forms a coating that contains the compound. Materials that may be used in a coating, include, for example, sugar, shellac, gelatin, or any other inert coating agent.

Pharmaceutical compositions including the disclosed compound may be prepared as a gas or aerosol. Aerosols encompass a variety of systems including colloids and pressurized packages. Delivery of a composition in this form may include propulsion of a pharmaceutical composition including the disclosed compound through use of liquefied gas or other compressed gas or by a suitable pump system. Aerosols may be delivered in single phase, bi-phasic, or multi-phasic systems.

In some aspects of the invention, the pharmaceutical composition including the disclosed compound is in the form of a solvate. Such solvates are produced by the dissolution of the disclosed compound in a pharmaceutically acceptable solvent. Pharmaceutically acceptable solvents include any mixtures of one or more solvents. Such solvents may include pyridine, chloroform, propan-1-ol, ethyl oleate, ethyl lactate, ethylene oxide, water, ethanol, and any other solvent that delivers a sufficient quantity of the disclosed compound to treat the indicated condition.

Pharmaceutical compositions may also include at least one pharmaceutically acceptable carrier. Carriers include any substance that may be administered with the disclosed compound with the intended purpose of facilitating, assisting, or helping the administration or other delivery of the compound. Carriers include any liquid, solid, semisolid, gel, aerosol or anything else that may be combined with the disclosed compound to aid in its administration. Examples include diluents, adjuvants, excipients, water, and oils (including petroleum, animal, vegetable or synthetic oils.) Such carriers include particulates such as a tablet or powder, liquids such as oral syrup or injectable liquid, and inhalable aerosols. Further examples include saline, gum acacia, gelatin, starch paste, talc, keratin, colloidal silica, and urea. Such carriers may further include binders such as ethyl celluose, carboxymethylcellulose, microcrystalline cellulose, or gelatin; excipients such as starch, lactose or dextrins; disintegrating agents such as alginic acid, sodium alginate, Primogel, and corn starch; lubricants such as magnesium stearate or Sterotex; glidants such as colloidal silicon dioxide; sweetening agents such as sucrose or saccharin, a flavoring agent such as peppermint, methyl salicylate or orange flavoring, or coloring agents. Further examples of carriers include polyethylene glycol, cyclodextrin, oils, or any other similar liquid carrier that may be formulated into a capsule. Still further examples of carriers include sterile diluents such as water for injection, saline solution, physiological saline. Ringer's solution, isotonic sodium chloride, fixed oils such as synthetic mono or diglycerides, polyethylene glycols, glycerin, cyclodextrin, propylene glycol or other solvent antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose, thickening agents, lubricating agents, and coloring agents.

The pharmaceutical composition may take any of a number of formulations depending on the physicochemical form of the composition and the type of administration. Such forms include solutions, suspensions, emulsions, tablets, pills, pellets, capsules, capsules including liquids, powders, sustained-release formulations, directed release formulations, lyophylates, suppositories, emulsions, aerosols, sprays, granules, powders, syrups, elixirs, or any other formulation now known or yet to be disclosed. Additional examples of suitable pharmaceutical carriers and formulations are well known in the art.

Methods of administration include, but are not limited to, oral administration and parenteral administration. Parenteral administration includes, but is not limited to intradermal, intramuscular, intraperitoneal, intravenous, subcutaneous, intranasal, epidural, sublingual, intramsal, intracerebral, iratraventricular, intrathecal, intravaginal, transdermal, rectal, by inhalation, or topically to the ears, nose, eyes, or skin. Other methods of administration include but are not limited to infusion techniques including infusion or bolus injection, by absorption through epithelial or mucocutaneous linings such as oral mucosa, rectal and intestinal mucosa, Compositions for parenteral administration may be enclosed in ampoule, a disposable syringe or a multiple-dose vial made of glass, plastic or other material.

Administration may be systemic or local, Local administration is administration of the disclosed compound to the area in need of treatment. Examples include local infusion during surgery; topical application, by local injection; by a catheter; by a suppository; or by an implant. Administration may be by direct injection into the central nervous system by any suitable route, including intraventricular and intrathecal injection. Intraventricular injection can be facilitated by an intraventricular catheter, for example, attached to a reservoir, such as an Ommaya reservoir. Pulmonary administration may be achieved by any of a number of methods known in the art. Examples include the use of an inhaler or nebulizer, formulation with an aerosolizing agent, or via perfusion in a fluorocarbon or synthetic pulmonary surfactant. Compounds may be delivered in the context of a vesicle such as a liposome or any other natural or synthetic vesicle. Additional examples of suitable modes of administration are well known in the art.

A pharmaceutical composition formulated to be administered by injection may be prepared by dissolving the disclosed compound with water so as to form a solution. In addition, a surfactant may be added to facilitate the formation of a homogeneous solution or suspension.

Surfactants include any complex capable of non-covalent interaction with the disclosed compound so as to facilitate dissolution or homogeneous suspension of the compound.

Pharmaceutical compositions may be prepared in a form that facilitates topical or transdermal administration. Such preparations may be in the form of a solution, emulsion, ointment, gel base, transdermal patch or iontophoresis device. Examples of bases used in such compositions include petrolatum, lanolin, polyethylene glycols, beeswax, mineral oil, diluents such as water and alcohol, and emulsifiers and stabilizers, thickening agents, or any other suitable base now known or yet to be disclosed.

Determination of an effective amount of the disclosed compound is within the capability of those skilled in the art, especially in light of the detailed disclosure provided herein. The effective amount of a pharmaceutical composition used to affect a particular purpose as well as its toxicity, excretion, and overall tolerance may be determined in vitro, or in vivo, by pharmaceutical and toxicological procedures either known now by those skilled in the art or by any similar method yet to be disclosed. One example is the in vitro determination of the $IC_{50}$ (half maximal inhibitory concentration) of the pharmaceutical composition in cell lines or target molecules. Another example is the in vivo determination of the $LD_{50}$ (lethal dose causing death in 50% of the tested animals) of the pharmaceutical composition. The exact techniques used in determining an effective amount will depend on factors such as the type and physical/chemical properties of the pharmaceutical composition, the property being tested, and whether the test is to be performed in vitro or in vivo. The determination of an effective amount of a pharmaceutical composition will be well known to one of skill in the art who will use data obtained from any tests in making that determination. Determination of an effective amount of disclosed compound for administration also includes the determination of an effective therapeutic amount and a pharmaceutically acceptable dose, including the formulation of an effective dose range for use in vivo, including in humans.

Treatment of a condition or disease is the practice of any method, process, or procedure with the intent of halting, inhibiting, slowing or reversing the progression of a disease, disorder or condition, substantially ameliorating clinical symptoms of a disease disorder or condition, or substantially preventing the appearance of clinical symptoms of a disease, disorder or condition, up to and including returning the diseased entity to its condition prior to the development of the disease. Generally, the effectiveness of treatment is determined by comparing treated groups with non-treated groups.

The addition of a therapeutically effective amount of a compound encompasses any method of dosing of a compound. Dosing of the disclosed compounds may include single or multiple administrations of any of a number of pharmaceutical compositions that include the disclosed compound as an active ingredient. Examples include a single administration of a slow release composition, a course of treatment involving several treatments on a regular or irregular basis, multiple administrations for a period of time until a diminution of the disease state is achieved, preventative treatments applied prior to the instigation of symptoms, or any other dosing regimen known in the art or yet to be disclosed that one skilled in the art would recognize as a potentially effective regimen. A dosing regimen including the regularity of and mode of administration will be dependent on any of a number of factors including but not limited to the subject being treated; the severity of the condition; the manner of administration, the stage of disease development, the presence of one or more other conditions such as pregnancy, infancy, or the presence of one or more additional diseases; or any other factor now known or yet to be disclosed that affects the choice of the mode of administration, the dose to be administered and the time period over which the dose is administered.

"Therapeutically effective amount" means that amount of a compound, material, or composition of the present invention, which is effective for producing a desired therapeutic effect, at a reasonable benefit/risk ratio applicable to any medical treatment. For example, a "therapeutically effective amount" is an amount effective to reduce or lessen at least one symptom of the disease or condition being treated or to reduce or delay onset of one or more clinical markers or symptoms associated with the disease or condition, or to modify or reverse the disease process.

"Treatment" or "treating" when referring to a disease or condition, means producing a desired therapeutic effect. Exemplary therapeutic effects include delaying onset or reducing at least one symptom associated with the disease, positively affecting (e.g., reducing or delaying onset) of a clinical marker associated with the disease and slowing or reversing disease progression.

"Pharmaceutically acceptable" refers to those properties and/or substances that are acceptable to a patient (e.g., human patient) from a toxicological and/or safety point of view.

Pharmaceutical compositions may be administered prior to, concurrently with, or after administration of additional or second pharmaceutical compositions. Concurrent administration means compositions are administered within about one minute of each other. If not administered concurrently, the additional or second pharmaceutical compositions may be administered a period of one or more minutes, hours, days, weeks, or months before or after the pharmaceutical composition that includes the currently disclosed compound. Alternatively, a combination of pharmaceutical compositions may be cyclically administered. Cycling therapy involves the administration of one or more pharmaceutical compositions for a period of time, followed by the administration of one or more different pharmaceutical compositions for a period of time and repeating this sequential administration. Cycling therapy may be used, for example, to reduce the development of resistance to one or more of the compositions, to avoid or reduce the side effects of one or more of the compositions, and/or to improve the efficacy of the treatment.

"Polo-like Kinase 1 Inhibitor" or "PLK1 inhibitor" refers to a compound or pharmaceutical composition that is capable of inhibiting the expression and/or the activity of the polo-like kinase 1 protein. For example, administration of a PLK1 inhibitor may partially or completely interrupt the physical, chemical, electrostatic or any other interactions between PLK1 protein and MDM2 and/or p53 protein. Some non-limiting examples PLK1 inhibitors include BI-2536, cyclapolin 9, GW 843682X, TC-S 7005, Wortmannin, NMS-P937, GSK461364A, any compounds disclosed in any of the following patent references, U.S. Pat. No. 7,517,873, U.S. Pat. No. 7,977,336, U.S. Pat. No. 8,318,727, or any combination thereof. For example, a PLK1 inhibitor can treat one or more symptoms or causes of PLK1-mediated conditions, such as adrenocortical carcinoma. In some aspects of the invention, the PLK1 inhibitor can be administered with one or more other pharmaceutical compounds. In some embodiments, a PLK1 inhibitor can comprise a composition that augments expression of the PLK1 protein, such as the addition of small interfering RNAs ("siRNAs").

"MDM2 inhibitor" refers to a compound or pharmaceutical composition that is capable of inhibiting the expression and/or the activity of the MDM2 protein. For example, an MDM2 inhibitor may comprise a compound or composition that is capable of partially or completely interrupting the physical, chemical, electrostatic or any other interactions between MDM2 protein and p53 protein. Some non-limiting examples of MDM2 inhibitors include any nutlin (e.g., nutlin-3), caylin-1, HLI 373, caylin-2, JNJ 26854165, NSC 66811, trans-4-iodo, 4'-boranyl-chalcone, any compounds disclosed in any of the following patent references, U.S. Pat. No. 8,569,341, U.S. Pat. No. 7,851,626, U.S. Patent Publication No. 2011/0251252, or any combination thereof.

In some aspects of the invention, the MDM2 inhibitor can be administered with one or more other pharmaceutical compounds (e.g., a PLK2 inhibitor). For example, the MDM2 and PLK1 inhibitors can be administered in a single dose/pharmaceutical composition to the subject receiving the treatment. In other aspects, the MDM2 and PLK1 inhibitors can be administered in two separate doses/pharmaceutical compositions that are provided to the subject at the same time, sequentially, or at regular or irregular intervals. In a preferred embodiment of the invention, the MDM2 and PLK1 inhibitors are administered together, either simultaneously or sequentially.

The present invention provides a kit to determine the levels of marker expression in the sample. Such a kit will comprise a reagent for detecting the mRNA encoding a marker, the corresponding polypeptide, or any combination or fragment thereof. The reagent will comprise one or more molecules capable of specifically binding a nucleic acid sequence (DNA or RNA) encoding a gene, or the corresponding polypeptide.

"Mitotic catastrophe inducing composition" or "mitotic catastrophe inducing compound" refers to one or more pharmaceutical compositions that are able to trigger mitotic catastrophe. For example, mitotic catastrophe inducing compounds may be any composition that is able to activate an initiator caspase (e.g., caspase 2) to trigger the caspase cascade to trigger apoptosis via mitotic catastrophe. In some embodiments, a mitotic catastrophe inducing compound does not activate or cause to be activated caspases 8 and 9 and does activate or cause to be activated caspase 2. In a preferred embodiment, a mitotic catastrophe inducing composition or compound is any active ingredient that can activate or cause to be activated caspase 2. Some non-limiting examples of a mitotic catastrophe inducing compound in include PLK1 inhibitors, MDM2 inhibitors, docetaxel, paclitaxel, moscatilin, S23806, radiation (e.g., ionizing radiation), subamolide A, doxorubicin, nocodazole, or any combination thereof.

The kit may comprise one or more nucleic acid reagents for the detection of mRNA encoding a gene (either sense or antisense). The one or more nucleic acid reagents may be used for hybridization and/or amplification of the mRNA encoding the gene. The kit may comprise one or more pairs of primers for amplifying the mRNA encoding the gene. The kit may further comprise samples of total mRNA derived from tissue of various physiological states, such as normal/non-diseased, and diseased (e.g., from a subject with cancer), for example, to be used as controls. The kit may also comprise buffers, nucleotide bases, and other compositions to be used in hybridization and/or amplification reactions. Each solution or composition may be contained in a vial or bottle and all vials held in close confinement in a box for commercial sale. Another embodiment of the present invention encompasses a kit for use in detecting mRNA encoding a gene in a biological sample comprising oligonucleotide probes effective to bind with elevated affinity to mRNA encoding the gene in vitro or in situ and containers for each of these probes.

In a further embodiment, the invention encompasses a kit for use in determining the level of marker expression in a biological sample comprising one or more agents, such as, for example, one or more antibodies, specific for one or more polypeptides or fragments. In one particular embodiment, the kit will comprise one or more agents and one or more nucleic acid markers wherein the agents and nucleic acid markers are modified in a fashion appropriate for carrying out immuno-polymerase chain reaction assays.

One preferred embodiment of the invention is directed to a kit for determining the levels of gene expression in a mammalian biological sample, wherein said levels of marker expression is an indicator of the prognosis or diagnosis of cancer, said kit comprising: a) an antibody that specifically binds to a gene product or an antigen binding fragment thereof, b) a reagent useful for detecting the extent of interaction between said antibody and the marker; c) a reagent or solution useful for antigen retrieval; and c) positive and/or negative control samples. Said antibody may be directly linked to an indicator reagent, wherein said indicator reagent is selected from the group consisting of fluorescent, colorimetric, immunoperoxidase and isotopic reagents. Alternatively, the kit may further include a second indicator antibody linked to an indicator reagent, wherein said indicator reagent is selected from the group consisting of fluorescent, colorimetric, immunoperoxidase and isotopic reagents.

In one embodiment, the kit contains at least one primary antibody, at least one labeled secondary antibody, and at least one substrate (e.g., TMB). Alternatively, the kits can contain radiolabeled secondary antibody in place of the secondary antibody labeled with an enzyme. The kits may also contain disposable supplies for carrying out detection assays (e.g., microtiter plates, pipettes).

EXAMPLES

Materials and Methods

Clinical Samples

Three ACC specimens were collected as part of an ongoing Adrenocortical Carcinoma Biorespository. The study was conducted under Western Institutional Review Board (WIRB) approved protocol #20051769 with written consent. Tumor samples were flash frozen within 30 minutes of collection and stored at −80° C. Peripheral blood was collected by venipuncture in sodium heparin vacutainers and kept at −80° C. until DNA extraction.

Next Generation Sequencing:

Genomic and exome (tumor and normal), and whole transcriptome (tumor only) libraries were generated and paired-end sequenced on the Illumina HiSeq2000. A pool of four normal adrenal glands from different individuals was RNA sequenced as a control.

Whole Genome Library Preparation

Genomic DNA samples were fragmented on the Covaris E210 96-well high-throughput sonicator to a target size of 1000 bp. Libraries were prepared and indexed using Illumina's TruSeq DNA Sample Preparation Kits. Ligation products 1100-1200 bp were size selected on a 2% TAE gel, purified, and enriched and amplified with 10 cycles of PCR using the TruSeq kit's PCR Master Mix and primer cocktail. Final libraries were quantified using the Agilent Bioanalyzer and Qubit and insert sizes verified using the Bioanalyzer.

Exome Library Preparation 1.1 μg of genomic DNA was used to prepare each library using the Illumina TruSeq DNA Sample Prep Kit and TruSeq Exome Enrichment Kit. Samples were fragmented to a target size of 200-300 bp using sonication and fragmentation was verified on a 2% TAE gel. Samples were then end repaired, purified, and adenylated. Adapter indexes were ligated onto adenylated molecules, purified, and amplified using PCR. 500 ng of each sample was combined to create a pool for exome capture. The pooled samples underwent a 24-hour hybridization, and were then washed and targets were eluted. This step was repeated for a total of two hybridizations. Final eluted targets were PCR amplified and evaluated using the Agilent Bioanalyzer.

RNAseq Library Preparation 10 ng of total RNA was used to generate whole transcriptome libraries for RNA sequencing. Using the Nugen Ovation RNA-Seq System v2, total RNA was used to generate double stranded cDNA, which was subsequently amplified using Nugen's SPIA linear amplification process. Amplified products were cleaned using Qiagen's QIAquick PCR Purification Kit and quantitated using Invitrogen's Quant-iT Picogreen. 1 μg of amplified cDNA was fragmented on the Covaris E210 to a target size of 300 bp. Illumina's TruSeq DNA Sample Preparation Kit was used for preparing libraries from amplified cDNA. 1 μg of amplified cDNA was fragmented to a target insert size of 300 bp, end repaired, and cleaned using Ampure XP beads. Samples were then adenylated at the 3' end and indexed paired end adapters with T overhangs are ligated onto the A-tailed inserts. Ligation products were run on a 2% TAE gel and size selected at 450 bp. Ligation products were isolated from gel punches using Bio-Rad Freeze 'n Squeeze columns and Ampure XP beads. Cleaned ligation products were then PCR amplified and cleaned using Ampure XP beads, and quantified using the Agilent Bioanalyzer and Qubit.

Paired End Sequencing

Libraries with a 1% phiX spike-in were used to generate clusters on HiSeq Paired End v3 flowcells on the Illumina cBot using Illumina's TruSeq PE Cluster Kit v3. Clustered flowcells were sequenced by synthesis on the Illumina HiSeq 2000 using paired-end technology and Illumina's 200 cycle TruSeq SBS Kit, extending to 104 bp for each of two reads for whole genome libraries and 75 bp 83 bp for each of two reads for exome and RNAseq libraries.

Bioinformatic Analyses:

Converted FASTQ files were aligned with BWA (Burrows-Wheeler Aligner) against Grch 37.62 and processed to produce BAM files without duplicate reads and re-aligned to facilitate tumor-normal comparisons. Somatic variant (SNV) calls were made with Seurat and annotated with snpEff. Copy number analysis of copy number variants (CNVs) was completed by determining the log 2 difference of the normalized physical coverage for germline and tumor samples across a sliding 2 kb window of the mean. Translocations were called with both svdetect and breakdancer. TopHat, Cufflinks, and Cuffdiff (Center for Bioinformatics and Computational Biology, University of Maryland) were used to align RNA reads and compute differential gene expression. Pathway enrichment was evaluated in MetaCore (Thompson-Reuters).

Tissue Culture

ACC cell lines SW-13 and H295R were obtained from ATCC and authenticated by STR analysis on Aug. 24, 2012. BD140 lines (A-C) represent distinct subclones established from the tumor of ACC140. BD167 was also established. They are positive for DHEAS expression, confirming adrenocortical origin. SW-13 and the BD140-B were grown in DMEM supplemented with 10% FBS, 1% L-glutamine, 1% inulin-transferin-selenium (ITS), and penicillin-streptomycin. BD140-A, BD140-B and BD167 were grown in RPMI supplemented with 10% FBS, 1% L-glutamine, 1% ITS, and penicillin-streptomycin. H295R was grown in DMEM:F12 supplemented with 2.5% NuSerum, 1% L-glutamine, 1% ITS, and penicillin-streptomycin. All cells lines were grown at 37° C. in a 5% $CO_2$ atmosphere.

Caspase 3/7 Glo Assay for Apoptosis

ACC cell lines were plated and 24 hours later, 0.5 μM, 1 μM, 2.5 μM, and 5 μM of doxorubicin was added to the cultures. The activity of caspases 3 and 7 was assessed using Caspase 3/7 Glo (Promega, Madison, Wis.) at 8, 24, and 48 hours after drug addition according to manufacturer's instructions. Data was normalized to cells alone, then to vehicle alone and expressed as a percentage of vehicle alone.

Induction of apoptosis after treatment with BI-2536 and nutlin-3 alone or together in combination was determined using the Caspase 3/7 Glo assay (Promega, Madison, Wis.). H295R cells were plated at a density of 1750 cells/well in 40 μl of medium and SW-13 was plated at 1250 cells/wells in 40 μl DMEM with 2% FBS. 24 hours after plating, the cells were treated with 100 μM, 33.3 μM, 11.1 μM, 3.703 μM and 1.234 μM of BI-2536 and nutlin-3 in a 10 μl volume. Induction of apoptosis was determined by the cleavage of caspase 3/7 using the Caspase 3/7 Glo assay (Promega, Madison, Wis.) at 8, 16, 24 and 48 hours after compound addition. Percent caspase 3/7 activity was normalized to cells and to DMSO control. Induction of apoptosis with double compounds was determined as above except $IC_{25}$ concentrations (0.00684 μM for SW-13 and 0.0374 μM for H295R) of BI-2536 were kept constant and nutlin-3 was evaluated in serial dilution. 5 μM Doxorubicin (Tocris, Minneapolis, Minn.) was used as a positive control for induction of apoptosis. In those cases, percent caspase 3/7 activity was also normalization to the median caspase 3/7 activity of BI-2536 alone.

In Vitro Drug Dose-Response Curves

Sensitivity to BI-2536 and nutlin-3 (Tocris, Minneapolis, Minn.), was tested as follows. H295R cells were plated at a density of 1750 cells/well in 40 μl of medium and SW-13 cells were plated at 1250 cells/wells in 40 μl DMEM with 2% FBS in white 384-well plates and allowed to attach for 24 hours. The cells were dosed with 3-fold dilutions of BI-2536 and nutlin-3 in 10 μl of medium and cell viability was assessed after 96 hours for SW-13 and 120 hours for H295R cells by CellTiter Glo (Promega, Madison, Wis.). Cell viability was normalized to cells alone and DMSO controls. Double compound studies were conducted as above except $IC_{25}$ concentrations (0.00684 μM for SW-13 and 0.0374 μM for H295R) of BI-2536 were kept constant and nutlin-3 was evaluated in a serial dilution, where, cell viability was normalized to cells, to DMSO controls and then to the median viability of BI-2536 alone.

Dose response curves and $IC_{50}$ values for cell survival in the presence of the drugs were calculated using Prism software (GraphPad) using the log(inhibitor) vs. response−4 parameter function which fits the following equation: $Y=Bottom+(Top-Bottom)/[1+10^{(X-Log\ IC_{50})}]$ where X is the logarithm of concentration and Y is the percent cell survival. Y starts at the top and goes to bottom with a sigmoid shape as X increases. All experiments were done at least three technical replicates and values are represented as averages with standard error.

siRNA Knockdown of PLK-1

$2\times10^5$ SW-13 and $3.5\times10^5$ H295R cells were plated in 6-well plates in their respective media without antibiotics and allowed to attach overnight. The next day, for SW-13, Lipofectamine2000 reagent (Invitrogen, Carlsbad, Calif.) and for H295R TransIT-siQUEST reagent (Mirus Bio, Madison, Wis.) was used to transfect in 20 nM PLK-1 siRNA (Qiagen, Valencia, Calif.), an all-stars negative siRNA (Qiagen, Valencia, Calif.) as a negative control, and a universally lethal positive-control siRNA directed against ubiquitin B (UBBs1) (Qiagen, Valencia, Calif.) using the manufacturer's recommended protocols respectively. For transfection of SW-13 cells, 5 μl of Lipofectamine2000 and 20 nM PLK-1, negative-control, or UBBs1 siRNA were mixed together in equal volumes, in serum free media (SFM) and allowed to incubate at room temperature for 30 minutes. All the media from the SW-13 wells was aspirated off and 500 μl of the siRNA-Lipofectamine2000 mix was added to each well along with 1.5 ml of media without antibiotics. Cells were assayed for PLK-1 protein expression 72 hours after transfection. For transfection of H295R cells, 4 μl of TransIT-siQUEST reagent was diluted in SFM. 20 nM PLK-1, negative-control, or UBBs1 siRNA was added to the diluted transfection reagent and allowed to incubate at room temperature for 20 minutes. 250 μl of the siRNA-TransIT-siQUEST mix was added to each well containing 1.25 ml of media without antibiotics. Cells were assayed for PLK-1 protein expression by western blot 72 hours after transfection.

To determine cell viability after PLK-1 transfection, SW-13 cells were reverse transfected with siRNA to PLK-1 or control siRNA and assayed for viability after 96 hours. Briefly, 384 well plates were printed with 20 nM of Hs_PLK-1__7 siRNA, UBBs1, negative control siRNAs, including a non-silencing scrambled siRNA or a siRNA directed against green fluorescent protein (GFP). A total of 20 μl of diluted Lipofectamine2000 solution was added to each well. After 30 minutes, 1200 cells for SW-13 in 20 μl of medium were added per well and then cultured at 37° C. After 96 hours, viability was assessed by CellTiter Glo following the manufacturer's protocol. Relative luminescence values were normalized to cells and to cells with transfection agent to get normalized percent viability.

To determine viability of H295R cells after PLK-1 transfection, H295R were transfected with PLK-1, negative-control or UBBs1 siRNA and assayed for viability after 72 hours. Briefly, 20,000 H295R cells were plated in 80 μl in 96 well plates and allowed to attach overnight. The next day 20 μl of TransIT-siQUEST reagent and 20 nM PLK-1, negative-control or UBBs1 siRNA in SFM were added to each well containing 80 μl of media without antibiotics. Cells were assayed for viability using CellTitre Glo 72 hours after transfection as per the manufacturer's protocol. Relative luminescence values were normalized to cells alone and then cells with transfection agent alone to get normalized percent viability.

Total RNA Extraction $6\times10^5$ SW-13 and $7.5\times10^5$ H295R cells were plated in 10 $cm^2$ dishes in 10 ml of media. Cells were allowed to adhere for 24 hours and were then treated with their respective BI-2536 $IC_{10}$, $IC_{25}$ and $IC_{50}$ doses including DMSO controls. Total RNA was extracted 24 hours later using the mirVana miRNA Isolation Kit (Ambion, Inc, Grand Island, N.Y.) as per the manufacturer's protocol.

RT-qPCR Validation of 053 and 021 mRNA Levels

Total RNA was reverse transcribed utilizing both random hexamer and oligo-dT primers and the $RT^2$ First Strand cDNA Synthesis Kit (SABiosciences, Valencia, Calif.). The resulting cDNA was amplified on the iQ5 Real-Time PCR Detection System (Bio-Rad Laboratories, Inc, Hercules, Calif.) using primer sets for TP53 (p53), CDKN1A (p21) and ACTB (β-actin) and $RT^2$ SYBR Green Master Mix (all from SABiosciences, Valencia, Calif.) and run according to manufacturer's instructions. Melting curve analysis was performed to evaluate primer set specificity. Fold difference relative to β-actin, which was used as the reference gene, was calculated using the Pfaffl method taking into account reaction efficiencies.

Expression of Caspases Using RT-qPCR

Total RNA from tumors was extracted using the mirVana miRNA Isolation Kit (Ambion Inc., Grand Island, N.Y.) as per the manufacturer's protocol. 1 μg of total RNA was used to synthesize cDNA with oligo-dT and random hexamer primers from the RT2 First Strand cDNA Synthesis Kit (SABiosciences, Valencia, Calif.). RT-qPCR reactions were carried out with 1 μl of cDNA mix and 1 μl of primer sets for Caspases 1 (PPH00105C), 2 (PPH0011A), 3 (PPH00107C), 4 (PPH00366F), 6 (PPH00109B), 7 (PPH00110C), 8 (PPH00359F), 9 (PPH353B), 10 (PPH00106F) and β-Actin (PPH00073G) with the RT2 SYBR Green Master Mix (all from SABiosciences, Valencia, Calif.) as per the recommended manufacturer's protocol. A melting curve analysis was also performed to evaluate specificity of the primer sets. Fold change in the expression of the caspases was calculated using the Pfaffl method (Pfaffl M W, *A new mathematical model for relative quantification in real-time RT-PCR* Nucleic Acids Res. (29) e45 (2001)) using calculated primer efficiencies and using β-Actin as the reference gene.

Western Blot Analysis $6\times10^5$ SW-13 and $7.5\times10^5$ H295R cells were plated in 10 $cm^2$ dishes in 10 ml of media. Cells were allowed to attach for 24 hours after which they were treated with $IC_{10}$, $IC_{25}$, $IC_{50}$ concentrations of BI-2536 and DMSO vehicle control for 24 hours. Cells were lysed with RIPA buffer with protease and phosphatase inhibitors, and the resulting protein lysate quantitated by BCA (Pierce, Thermo Scientific, Pittsburgh, Pa.). Thirty micrograms of protein were loaded onto 4-12% Bis-Tris pre-cast gels (Invitrogen, Carlsbad, Calif.) and allowed to separate at 150V for 1 hour. The gels were then transferred onto PVDF membranes for 7 minutes using the iBLOT western transfer system (Invitrogen, Carlsbad, Calif.) at room temperature. Following the transfer of proteins, the membranes were blocked in 5% blocking solution made from, non-fat dry milk dissolved in 1×TBST (50 mM Tris.HCl, pH 7.4, 150 mM NaCl+0.1% Tween 20) for 1 hour. Primary PLK-1 antibody (Cell Signaling, Technology, Danvers, Mass.) at a dilution of 1:500 was added to membranes in 5% BSA (1×TBST+5% BSA) overnight at 4° C. Primary antibodies to MDM2 (AbCam, Cambridge, Mass.) and p53 (AbCam, Cambridge, Mass.) at a dilution of 1:500 were added to the membranes in 1% blocking solution overnight at 4° C. The next day the membranes were washed with 1×TBST twice for 10 minutes and appropriate HRP labeled secondary anti-rabbit (Cell Signaling Technology, Danvers, Mass.) for PLK-1 and anti-mouse (Cell Signaling Technology, Danvers, Mass.) for MDM2 and p53 antibodies were added to the blots at a dilution of 1:1000 for 2 hours at room temperature. The blots were then washed in 1×TBST four times for 10 minutes. The membranes were developed using the SuperSignal West Femto Chemiluminescent Substrate (Pierce, Thermo Scientific, Pittsburgh, Pa.) and were visualized and quantitated with the Bio Spectrum 500 Imaging System (UVP, Cambridge, UK).

The blots were processed as described above for the detection of β-Actin (AbCam, Cambridge, Mass.) in 5% blocking solution which was used as an internal loading control. The β-Actin antibody was used at a dilution of 1:1000 along with the anti-rabbit secondary antibody also at a dilution of 1:1000. The actin membranes were also detected using the SuperSignal West Femto Chemiluminescent Substrate (Pierce, Thermo Scientific, Pittsburgh, Pa.) and were visualized and quantitated with the Bio Spectrum 500 Imaging System (UVP, Cambridge, UK) and relative amounts of PLK-1, MDM2 and p53 protein are reported relative to β-Actin. All experiments were done in three technical replicates and are represented as averages with standard error.

To determine PLK-1 protein expression after siRNA knockdown, blots for PLK-1 and β-Actin were processed as described above. Relative amounts of the PLK-1 protein after siRNA knockdown are reported relative to β-Actin. All experiments were done in three technical replicates and are represented as averages with standard error.

Statistical Analysis

Statistical assessment of caspase expression and apoptosis was done in GraphPad Prism 6 (GraphPad Software, Inc., La Jolla, Calif.) using 2-way ANOVA followed by Sidak's multiple comparisons test (RT-qPCR) or Dunnett's multiple comparison test (apoptosis). p-values below 0.05 were considered to be significant.

Results

Example 1

Patient clinical information is listed in Table 1. These tumors were characterized by the presence of shared genomic alterations as well as tumor specific events that converged on common pathways.

TABLE 1

Clinical Description of ACC Patient and Tumor Characteristics

| Sample* | Age (years) | Survival (years) | Tumor Stage | Tumor Grade | Weiss Score | Tumor Hormone Status |
|---|---|---|---|---|---|---|
| ACC 129 | 55 | 0.583 | 2 | 4 | 4 | cortisol, DHEAS |
| ACC 132 | 51 | 6 | Recurrence | 2 | NA | non-functional |
| ACC 140 | 63 | 2.08 | 4 | 4 | 4 | non-functional |

Example 2

Differential Caspase Expression in ACC Samples

Differential gene expression was evaluated relative to a pool of 4 normal adrenals through pathway enrichment in GeneGo and analyzed the involvement of pathways involved in ACC pathogenesis, including p53 responses and IGF2 signaling. GeneGo analysis identified commonly affected pathways, including loss of caspase 9 (CASP9) expression.

In ACC 129, IGF2 signaling appeared to be directed towards suppression of apoptosis through 14-3-3. In ACC 132 and ACC 140, signaling was repressed, and instead, ACC 132 and ACC 140 have evidence of MET amplification and signaling. All tumors also under-expressed beta-catenin. p53 transcriptional response was disrupted in all tumors, with the two wild-type p53 tumors (ACC 129 and ACC132) over-expressing MDM2.

Because sporadic adult ACC is usually wild-type for p53 yet highly resistant to chemotherapy, cell death response pathways were studied, including the caspase cascade, which is central to both apoptosis and necroptosis. It was observed that all three tumors had a reduction in CASP9 expression. Each tumor harbored additional alterations in caspase signaling, most commonly resulting in loss of initiator caspase expression, as illustrated in FIG. 1.

Example 3

Confirmation of Differential Caspase Expression Via Quantitative RT-PCR

Figure 2:
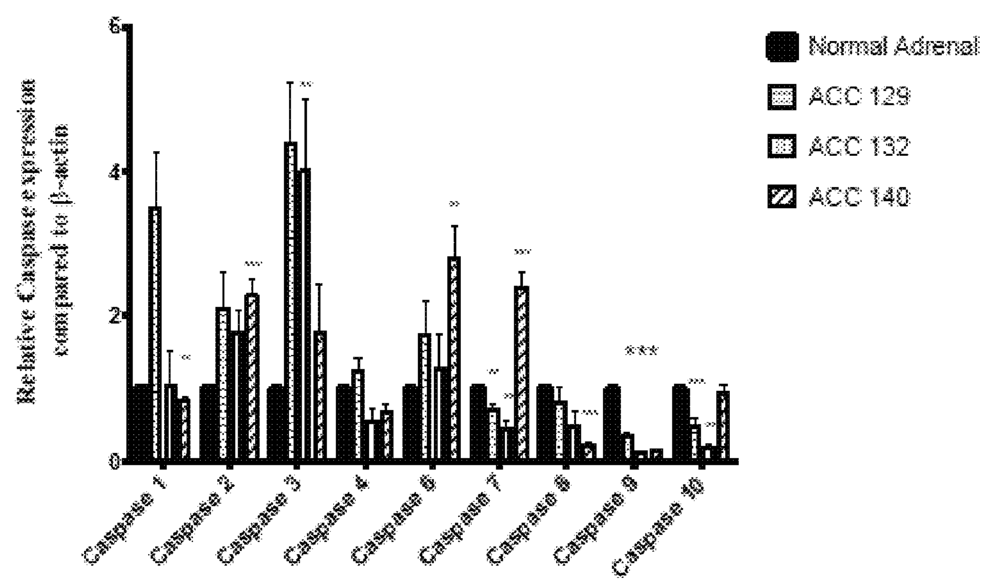
FIG. 2 is a series of graphs that illustrate that ACC tumors and cell lines are characterized by a lack of caspase 9 expression at the mRNA level. (A) RT-qPCR values of caspases 1-10 compared to normal adrenal RNA from each of the tumors assessed. (B) RT-qPCR values of caspases 1-10 in the two commercially available ACC cell lines, SW-13 and H295R. Data plotted is the mean with the SEM of three biological replicates with three technical replicates per biological replicate. $^{}p<0.01$, $^{*}p<0.0001$.
Figure 2:
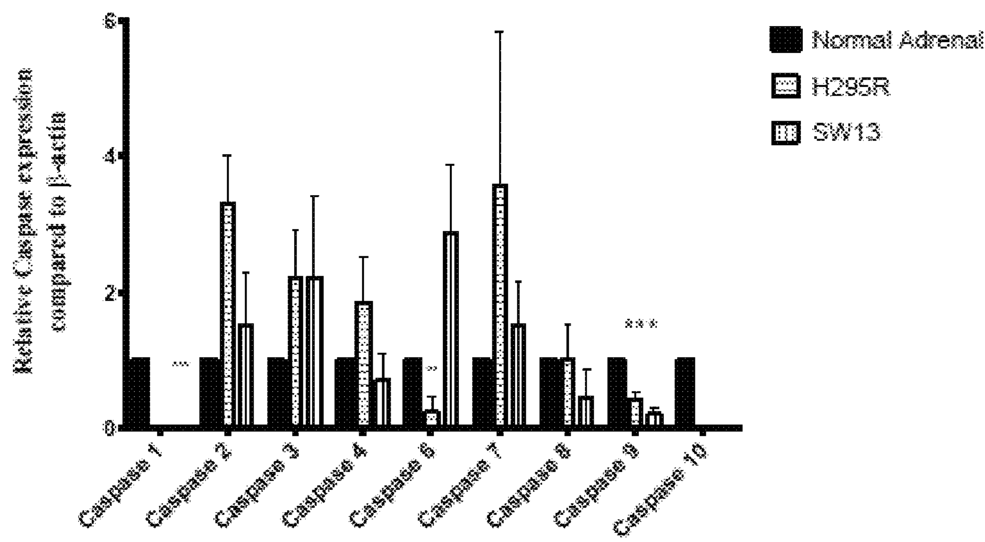

As shown in FIG. 2, the expression of multiple caspases was altered, with CASP9 being significantly under-expressed in all three tumors and in the ACC cell lines H295R and SW-13. The primary tumors (panel A) and the cell lines, H295R, and SW-13 (panel B), show increased expression of caspase 2, with over-expression being statistically significant in ACC140 and H295R. Additionally, two of the tumors over-express one or more of the effector caspases.

Example 4

Reduced Caspase Expression Correlates with Reduced Apoptotic Response

Figure 3:
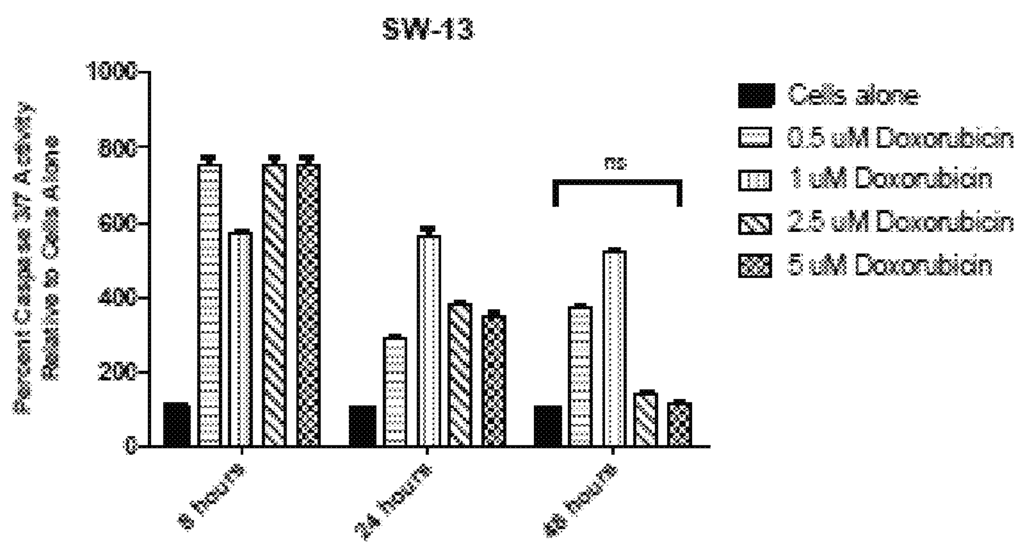
FIG. 3 is a series of graphs that illustrate that the lack of caspase 9 expression results in a delay of caspase 3/7 activation after doxorubicin exposure in all ACC cell lines, except SW-13. Bars indicate comparisons that were not significantly different using a corrected p-value of <0.05 as the cut-off.
Figure 3:
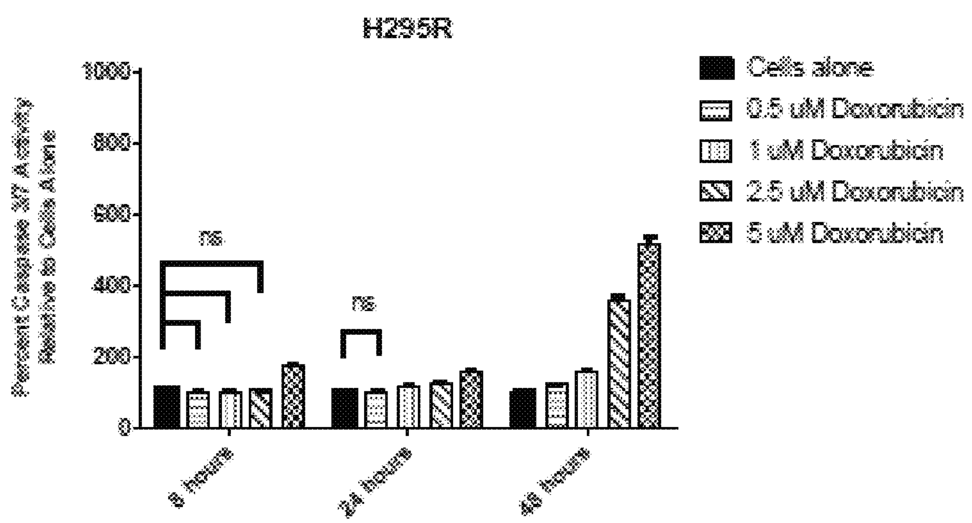
Figure 3:
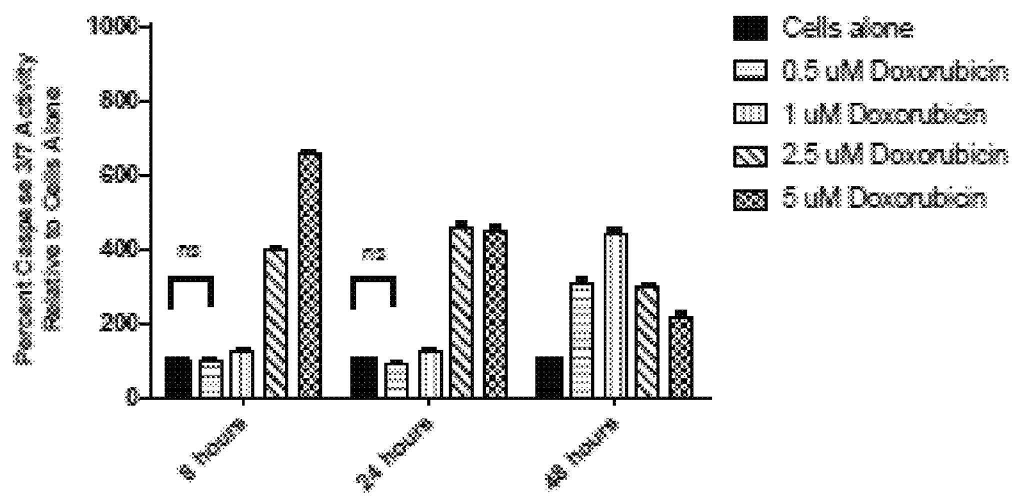
Figure 3:
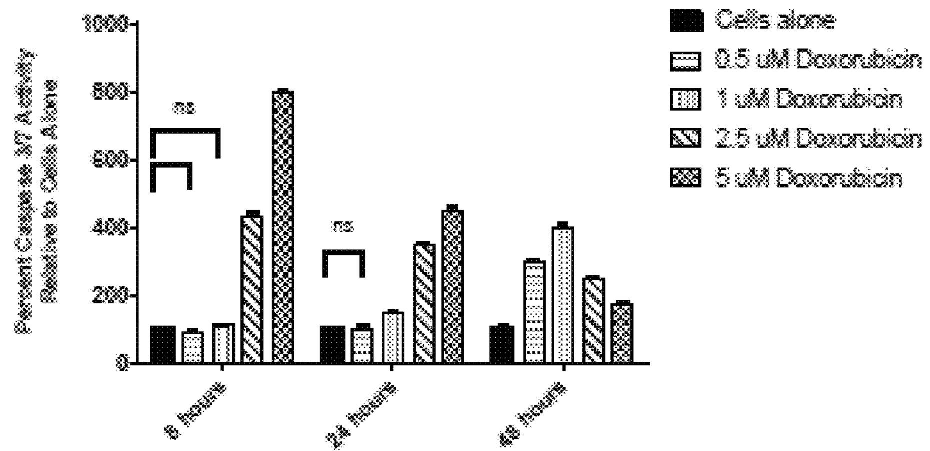
Figure 3:
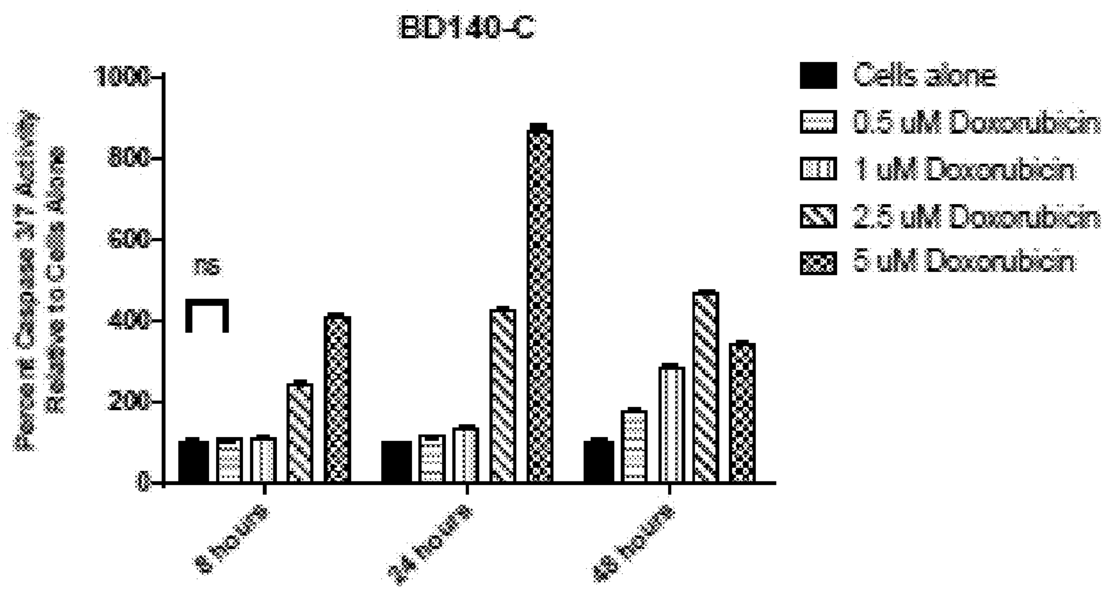

A time series was used for assaying caspase 3/7 activation following doxorubicin exposure using clinically relevant concentrations. FIG. 3 shows that apoptosis is delayed in the H295R cell line (panel B). There appears to be no impact on SW-13 response, with a significant induction within 8 hours (panel A). The BD140 lines (three different clones derived from ACC140) have different responses, but fall between H295R and SW-13, with moderate induction of caspase 3/7 activity only seen at 2.5 μM and 5 μM concentrations by 24 hours. At the doses of doxorubicin commonly used to assess caspase activation (0.5 μM and 1 μM), induction of caspase 3/7 activity was not seen until 48 hours in the BD140 lines.

Example 5

Inhibition of Polo-Like Kinase 1 (PLK-1) Reduces the Viability of ACC Cell Lines Examination of previous gene expression data (Demeure, M. J. et al., *PTTG*1 *overexpression in adrenocortical cancer is associated with poor survival and represents a potential therapeutic target* Surgery (154) 1405-1416 (2013)) showed that PLK1 was over-expressed in a subset of tumors with a mean fold-change relative to normal adrenal of 1.4. Since increased PLK-1 expression has been correlated to poor prognosis and aggressiveness of cancers, the effect of down-regulating PLK-1 on the ACC cell lines was investigated. Knocking down expression of PLK-1 using siRNA not only reduced the amount of PLK-1 protein (FIG. 4, panel A and B), but also decreased the viability of both H295R and SW-13 cell lines to levels close to that of the positive control, UBB1, after siRNA knockdown (FIG. 4, panel C), which indicates that the ACC cell lines were sensitive to the loss of PLK-1.

Figure 4:
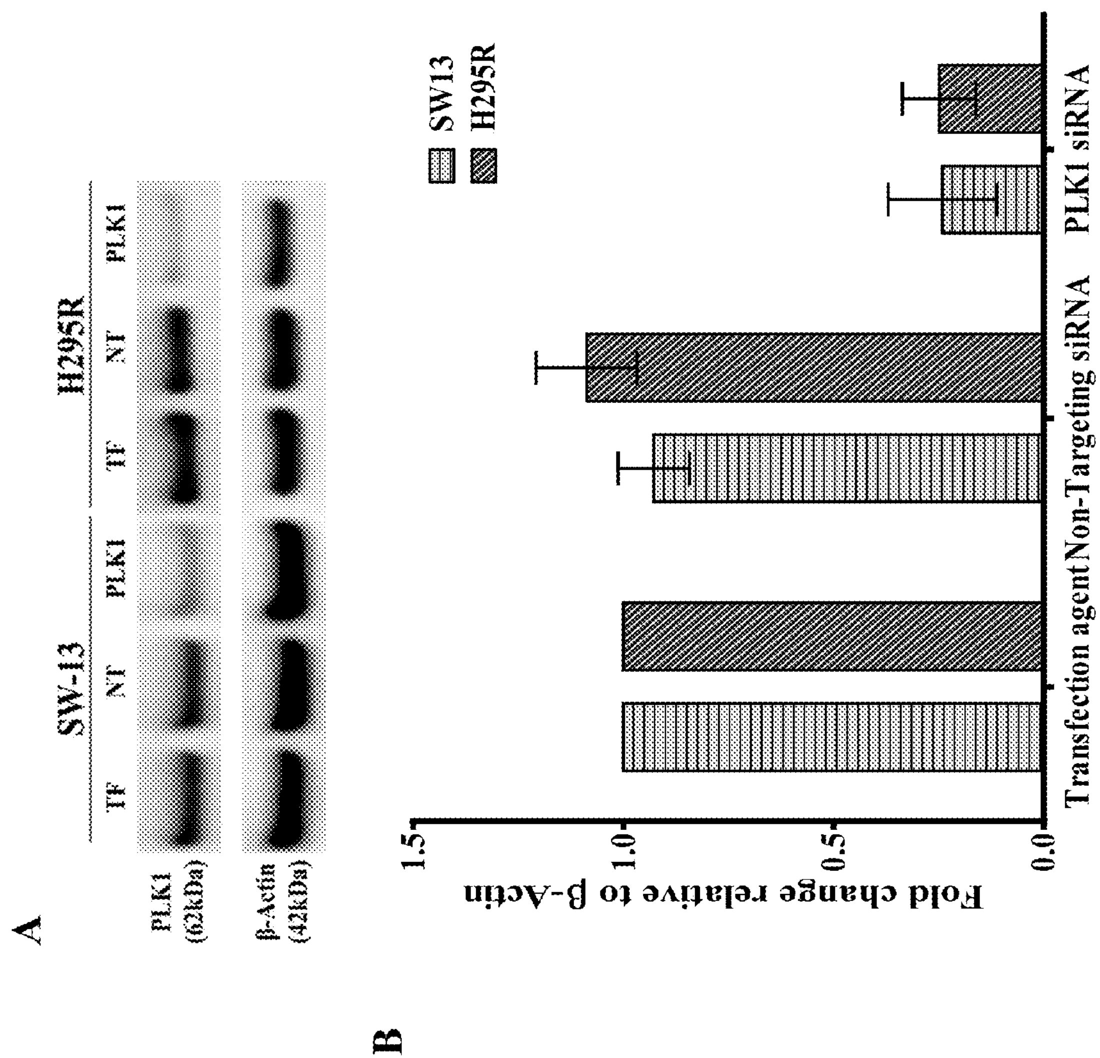
FIG. 4 illustrates that the inhibition of Polo-like kinase 1 (PLK-1) reduced the viability of ACC cell lines. (A) ACC cell lines, H295R and SW-13 were treated with PLK-1 siRNA and amount of PLK-1 protein was determined after 72 hours of siRNA treatment. (B) Quantitation of PLK-1 protein western after siRNA knockdown expressed relative to β-actin. (C) Knocking down expression of the PLK-1 protein reduced viability of the H295R & SW-13 cell lines as compared to the controls. (D and E) Treating the cells with BI-2536, an inhibitor of PLK-1, reduced the viability of both the H295R and SW-13 ACC cell lines. All experiments were performed in at least 3 technical replicates and data are represented as means with standard error. TF=Transfection agent and NT=Non-targeting siRNA.
Figure 4:
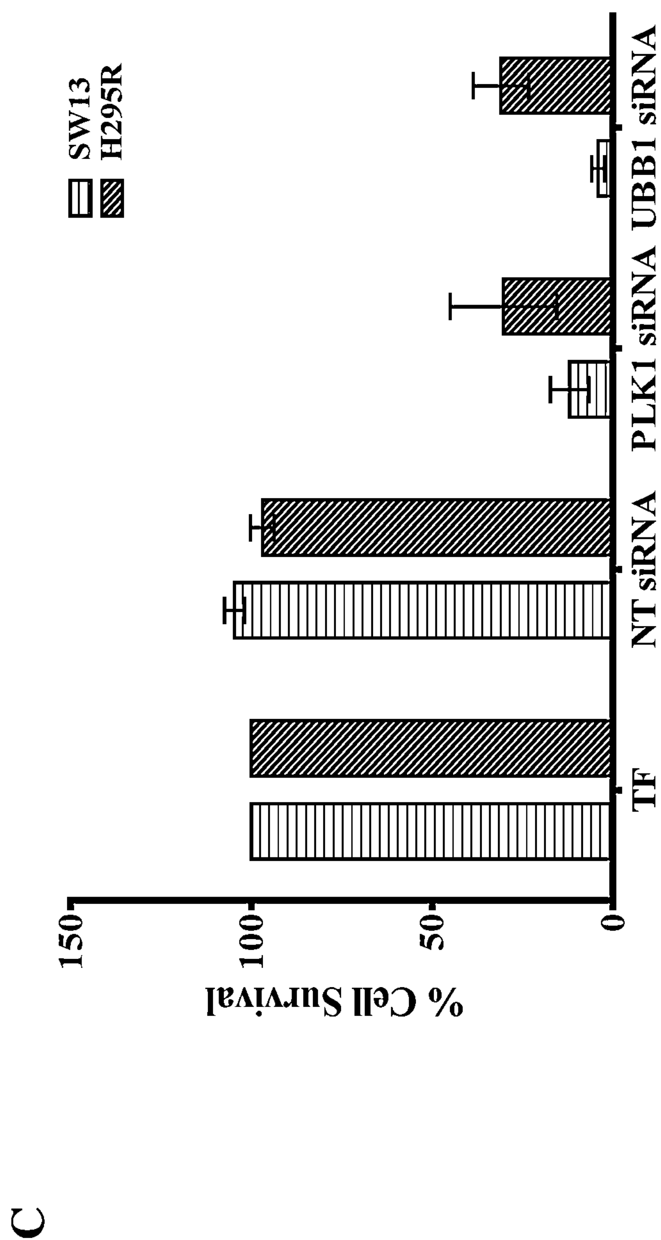
Figure 4:
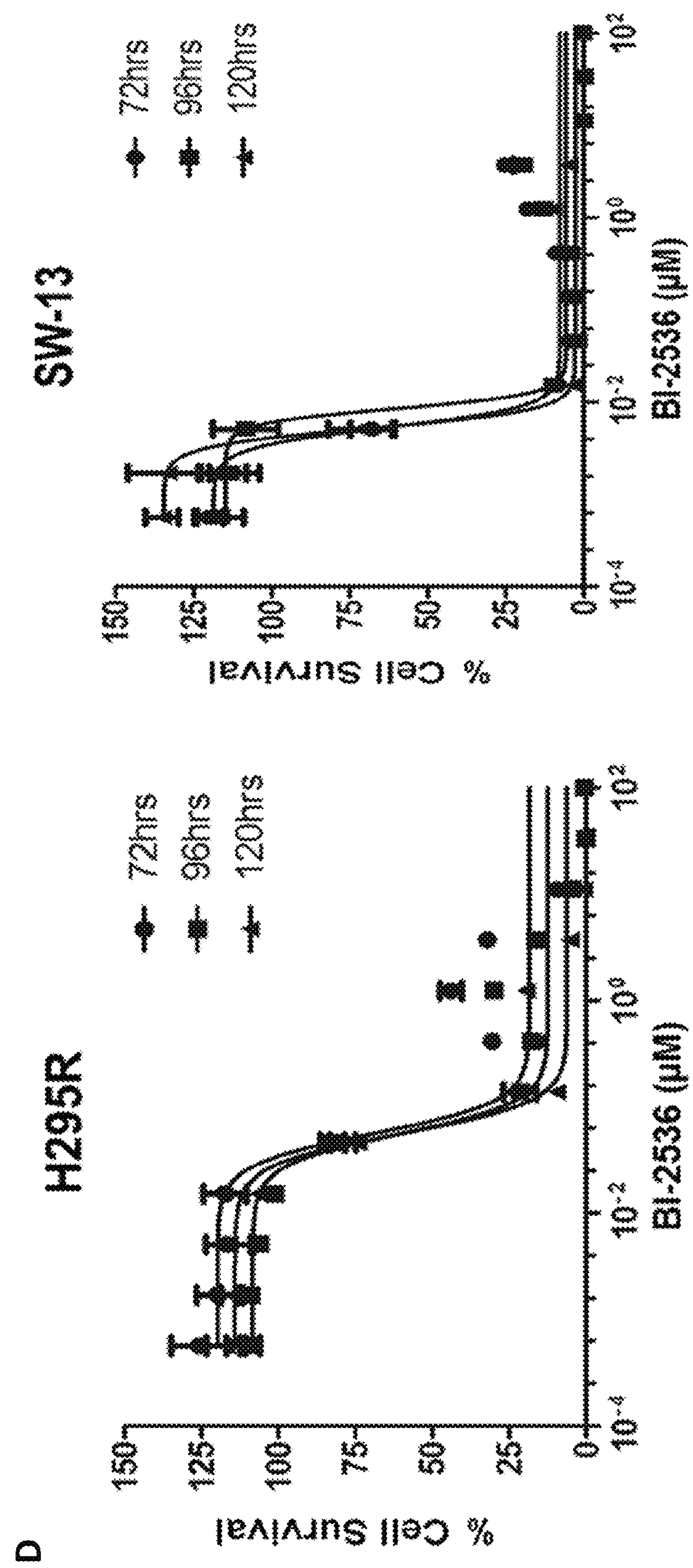

Exposure to the PLK-1 inhibitor, BI-2536, showed that both H295R and SW-13 cell lines were also sensitive to PLK-1 inhibition (FIG. 4, panel D and E). At 96 hours following addition of drug, H295R had an $IC_{50}$ value of 0.063 μM and SW-13 had with an $IC_{50}$ value of 0.0095 μM (FIG. 4, panel D and E, Table 2). These values are below the concentrations achieved clinically (31.2-55.20) following a single intravenous injection of 50-70 mg of BI-2536. Frost, A. et al., *Phase i study of the Plk*1 *inhibitor BI* 2536 *administered intravenously on three consecutive days in advanced solid tumors* Curr. Oncol. (19) 28-35 (2012).

TABLE 2

BI-2536 inhibitory concentrations

| Cell line | BI-2536 (μM) | | |
|---|---|---|---|
| | $IC_{10}$ | $IC_{25}$ | $IC_{50}$ |
| H295R | 0.00565 | 0.00684 | 0.0095 |
| SW-13 | 0.0222 | 0.0374 | 0.0628 |

Example 6

Inhibition of PLK-1 Reduces Levels of Mutant 053 Protein but not Wild Type p53

Figure 5:
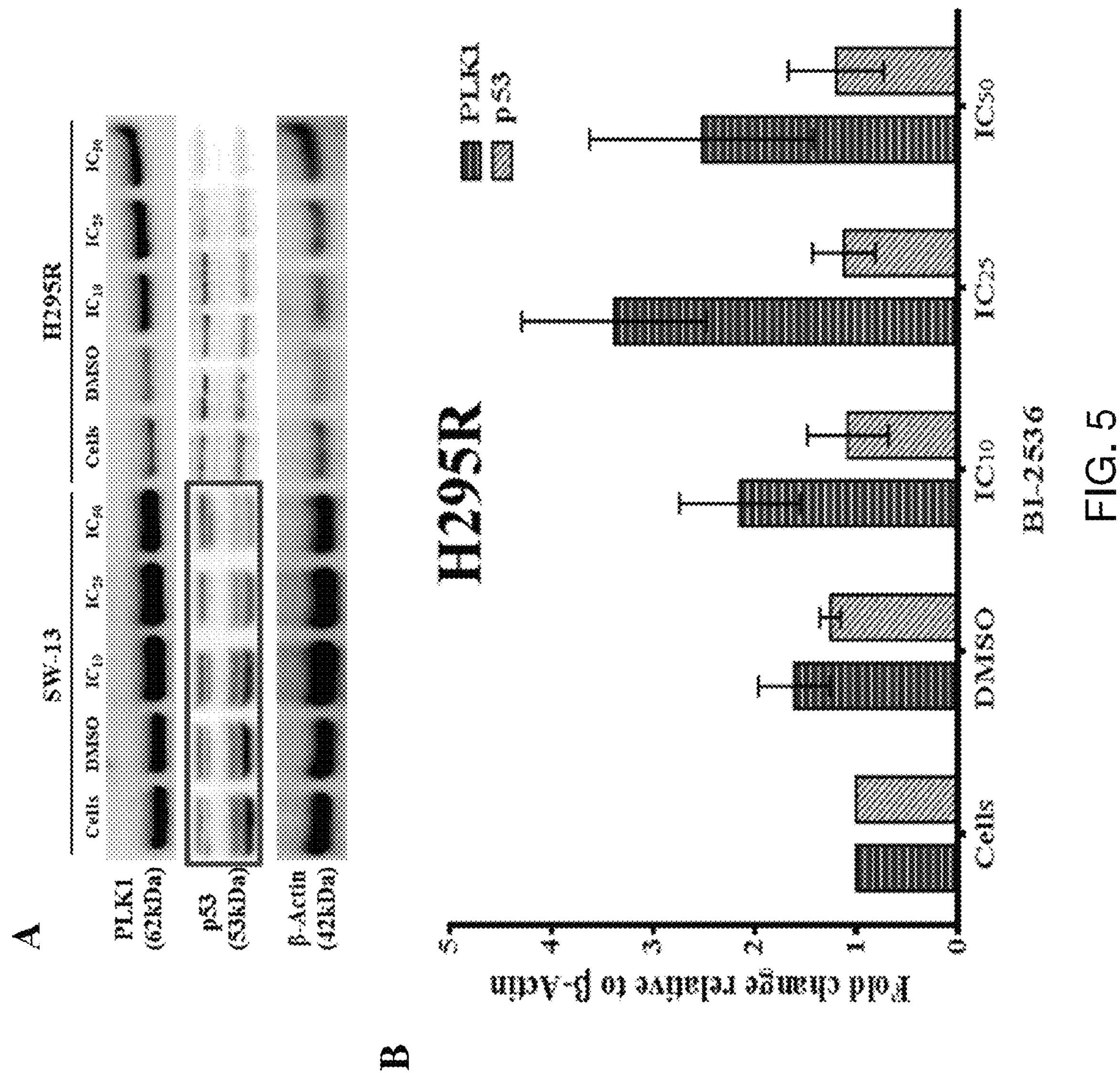
FIG. 5 illustrates that inhibition of PLK-1 reduces expression of mutant p53 protein in SW13 cells. As PLK-1 has been shown to physically interact with p53 to control its functions, the levels of the wild type p53 protein should not be affected after inhibition of PLK-1. (A) BI-2536 treatment resulted in a decrease in the amount of mutant p53 protein in the SW-13 cells, but did not change expression of the wild type p53 protein in the H295R cells. (B and C) Quantitation of PLK-1 and p53 protein western blots shown in panel (A) after BI-2536 treatment expressed relative to β-actin. (D) Inhibition of PLK-1 with BI-2536 did not reduce transcript levels of either wild type or mutant p53 as determined by qRT-PCR. All experiments were performed in at least 3 technical replicates and data are represented as means with standard error.
Figure 5:
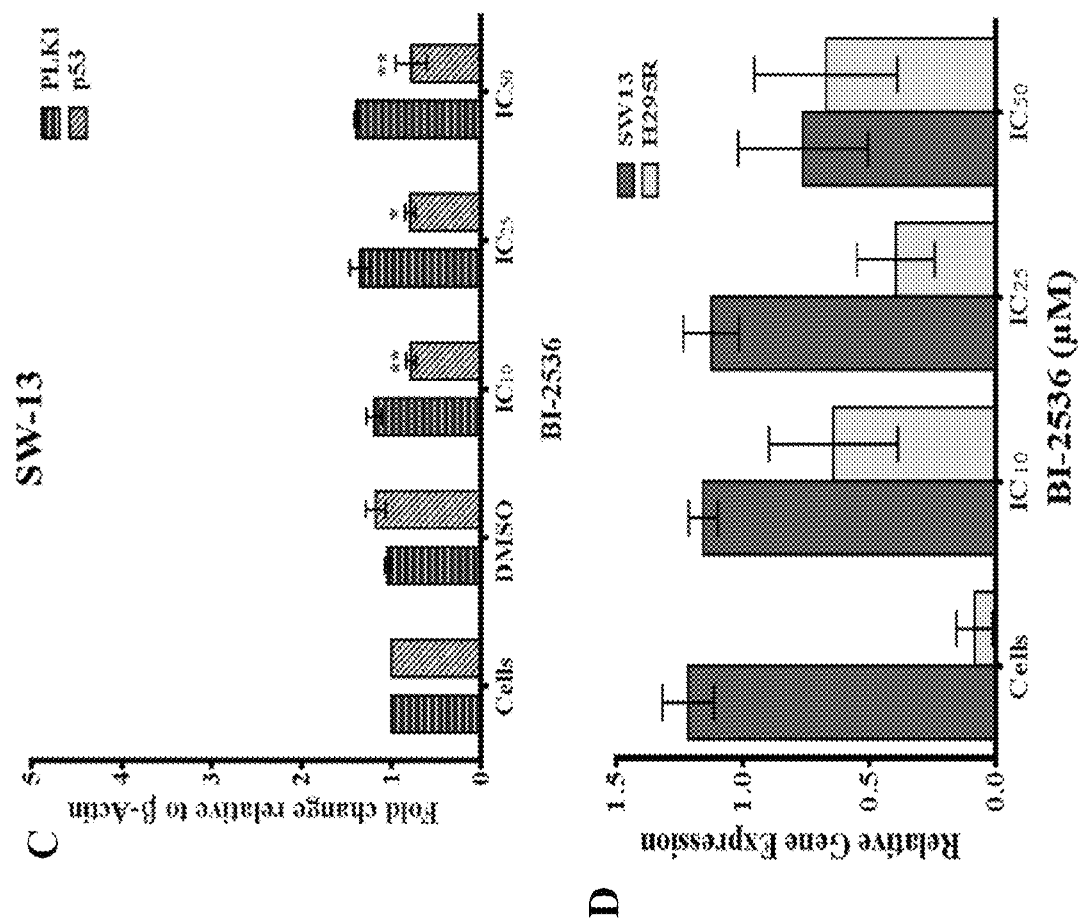

PLK-1 is a negative modulator of p53 activity but does not affect its expression levels. Ando, K. et al., *Polo-like kinase* 1 (*P*1*k*1) *inhibits p*53 *function by physical interaction and phosphorylation* J. Biol. Chem. (279) 25549-25561 (2004). p53 protein levels were examined by immunoblot using an antibody that recognizes both mutant and wild-type p53 isoforms. A dose-dependent decrease of mutant p53 protein levels was observed in SW-13 cells but not in the wild-type p53 protein levels in H295R cells (FIG. 5, panels A-C). Treatment with BI-2536 did not significantly affect the levels of p53 transcript in either of the two cell lines (FIG. 5, panel D).

Example 7

Inhibition of PLK-1 Restores Functioning of Wild Type p53

Figure 6:
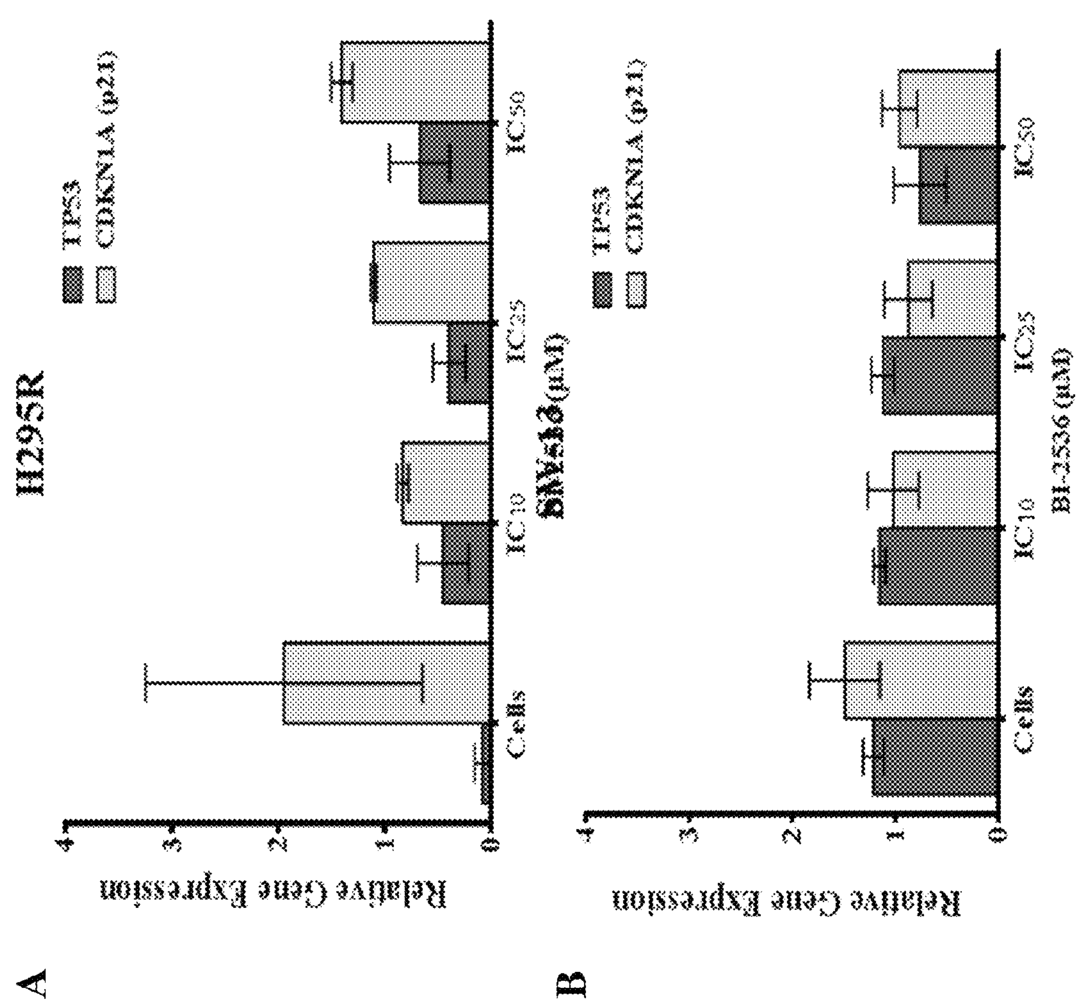
FIG. 6 illustrates that inhibition of PLK-1 restores p53 functioning. Since PLK-1 is a negative regulator of p53, inhibition of PLK-1 should restore p53 transactivation and apoptotic functions. (A) Treatment of H295R and SW-13 cells with BI-2536 resulted in the restoration of wild type p53's transactivation functions as seen by the increased transcription of its downstream gene, CDKN1A (p21), as determined by qRT-PCR. (B) BI-2536 treatment of the SW-13 did not increase the transcription of CDKN1A, as this cell line possess a mutant p53 gene. (C) Furthermore, inhibition of PLK-1 restored wild type p53's apoptotic response in H295R cells as determined by the Caspase 3/7 glo assay. (D) The apoptotic response was slightly delayed in the SW-13 cells with mutant p53 with maximum response observed at 48 hours. Doxorubicin was used as a positive control for apoptosis. All experiments were performed in at least 3 technical replicates and data are represented as means with standard error.
Figure 6:
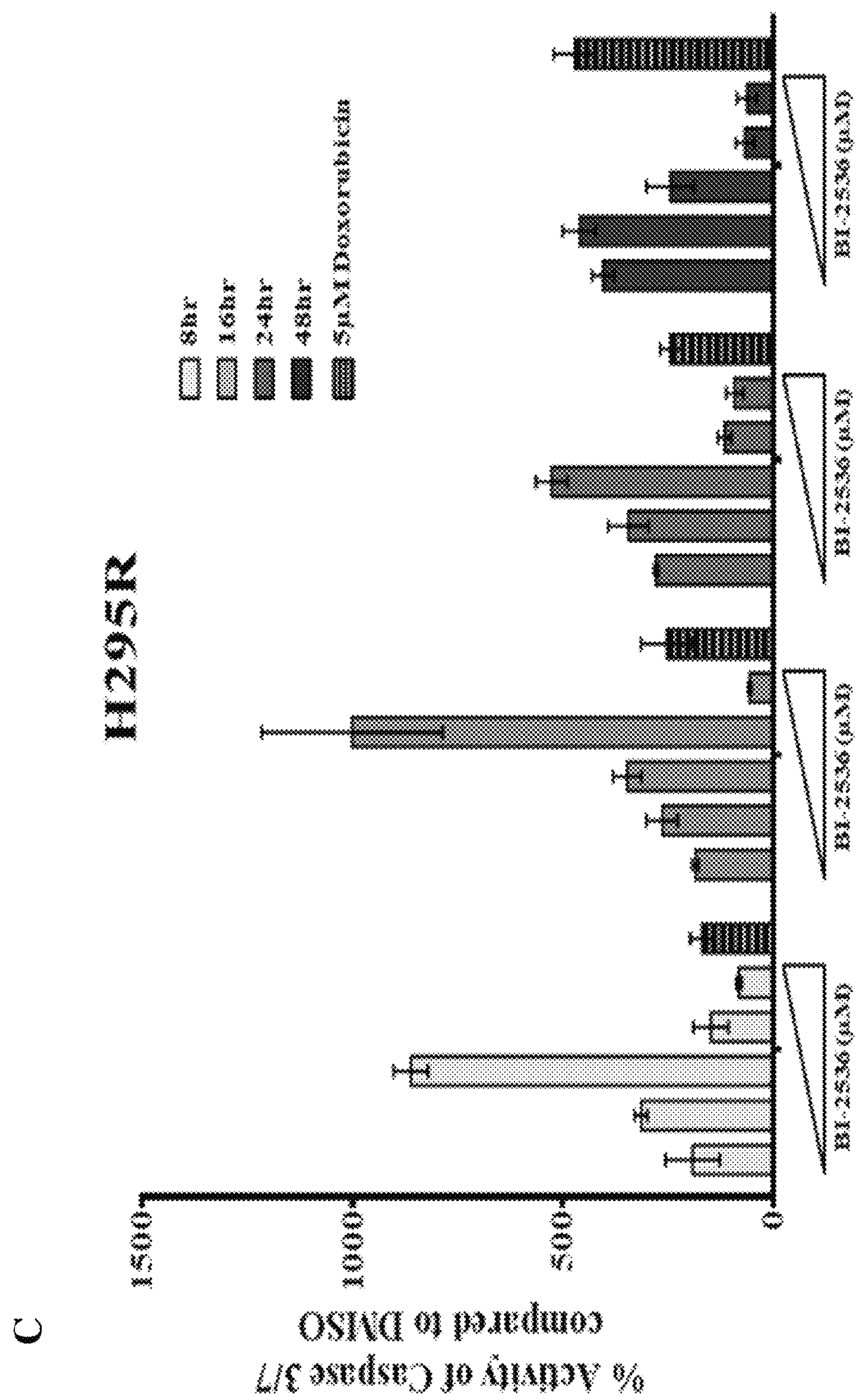
Figure 6:
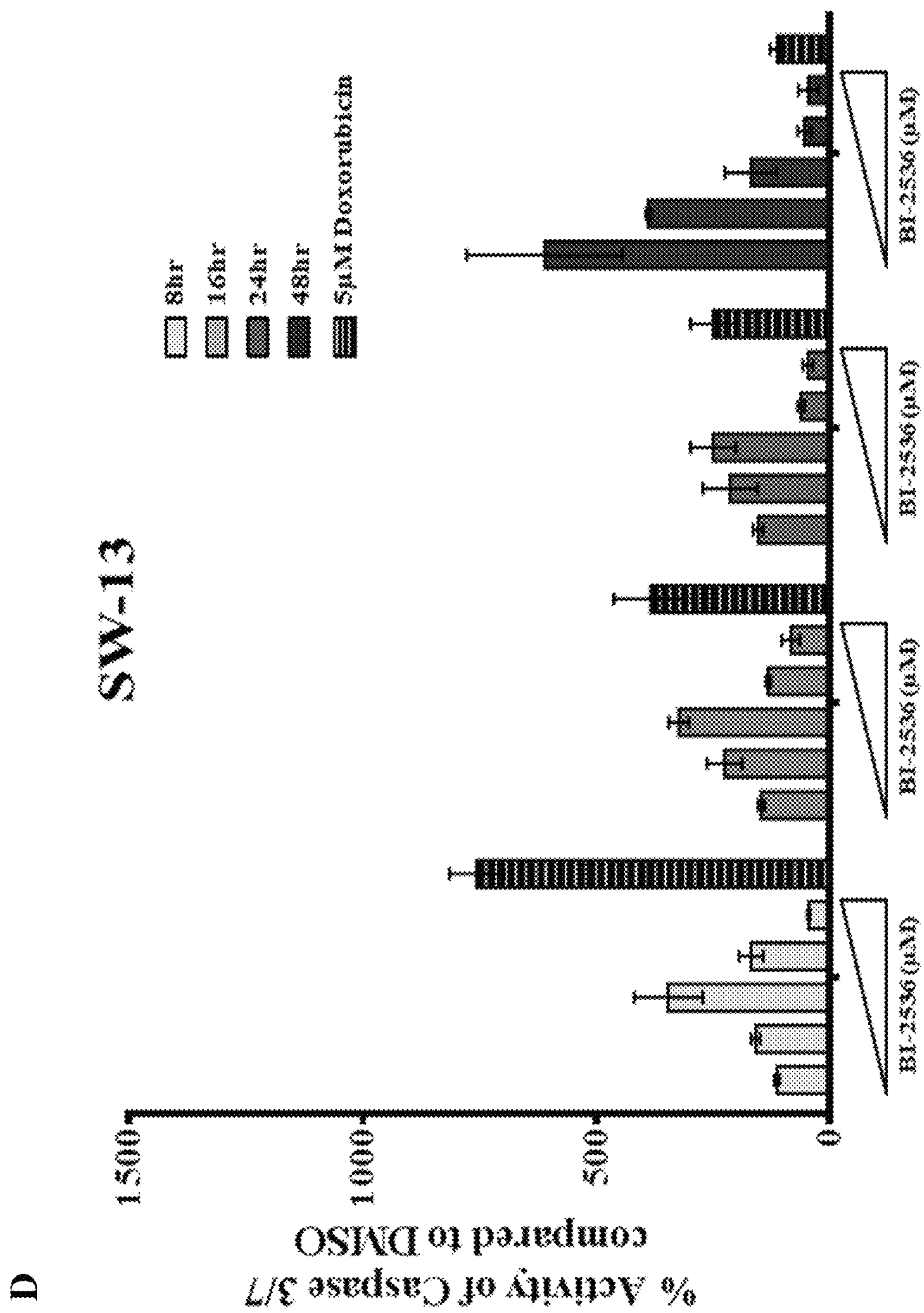

Inhibition of PLK-1 with BI-2536 resulted in a general trend of increased transcription of CDKN1A, a gene that encodes the p21 protein, in H295R cells with wild type p53 (FIG. 6, panel A). A decrease in mutant p53 protein in SW-13 cells after exposure to BI-2536 also reduced the amount of CDNK1A message (FIG. 6, panel B). Treatment with BI-2536 resulted in a robust induction of apoptosis after treatment with BI-2536 in H295R cells (FIG. 6, panel C) and in SW-13 cells with mutant p53 (FIG. 6, panel D). Maximum induction of apoptosis in SW-13 cells was observed at 48 hrs, while only high concentrations of BI-2536 resulted in an increase in apoptosis at early time points (FIG. 6, panels C and D).

Example 8

Synergy of PLK-1 Inhibition by BI-2536 with MDM2 Inhibition by Nutlin-3

Figure 7:
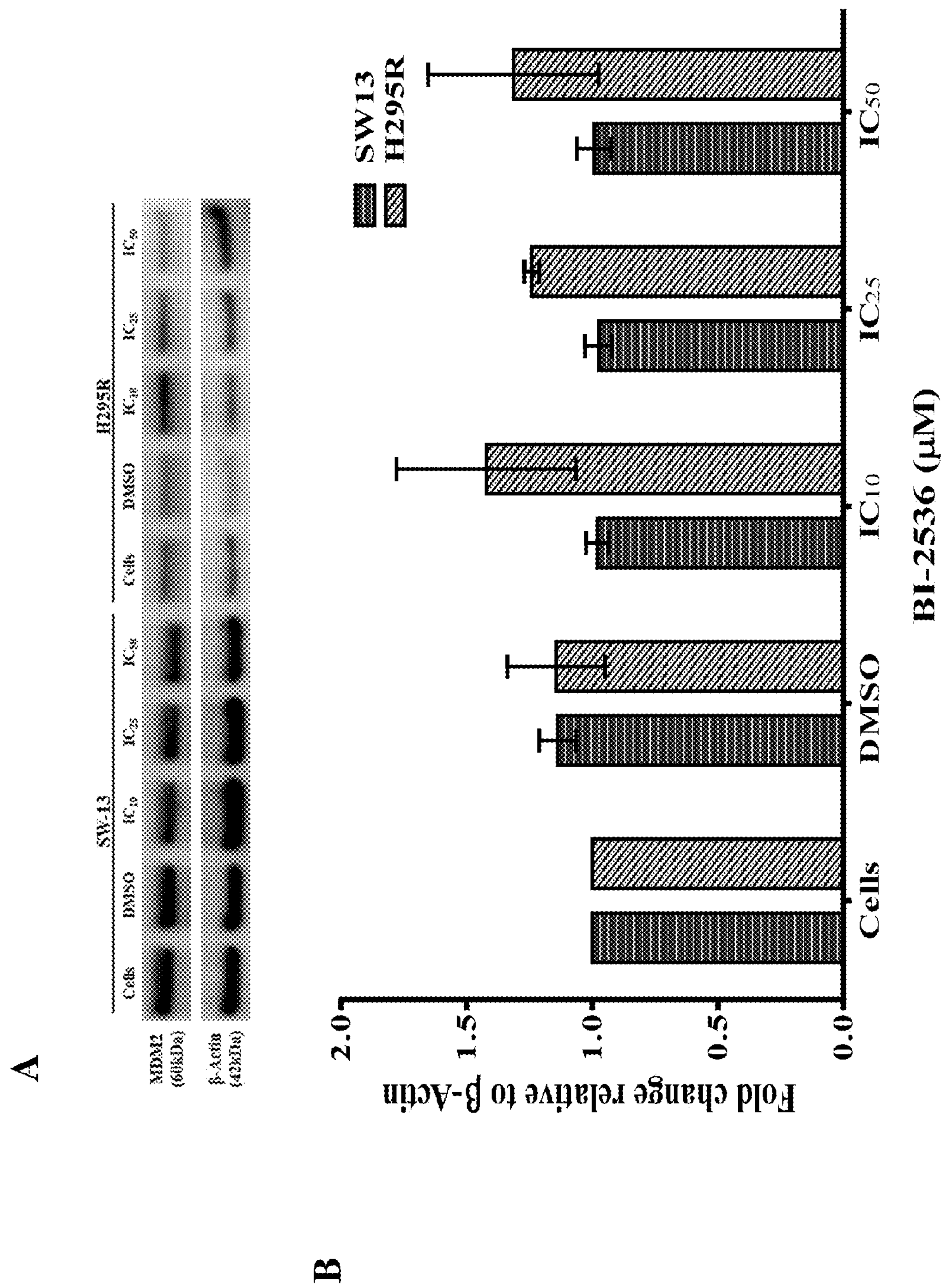
FIG. 7 illustrates that inhibition of MDM2 by nutlin-3 restores wild type p53's apoptotic response. Since PLK-1 also indirectly controls p53's activity via MDM2, the effect of PLK-1 inhibition on MDM2 functioning was determined. (A) Inhibition of PLK-1 with BI-2536 did not change the levels of the MDM2 protein. (B) Quantitation of the MDM2 protein western blot after BI-2536 treatment expressed relative to β-actin. (C) Treating the cells with nutlin-3, an inhibitor of MDM2, reduced the viability of both the H295R and SW-13 ACC cell lines. (D) Inhibition of MDM2 restored wild type p53's apoptotic response in H295R cells as determined by the Caspase 3/7 glo assay. (E) A small increase in apoptosis was observed in the SW-13 cells with mutant p53. Doxorubicin was used as a positive control for apoptosis. All experiments were performed in at least 3 technical replicates and data are represented as means with standard error.
Figure 7:
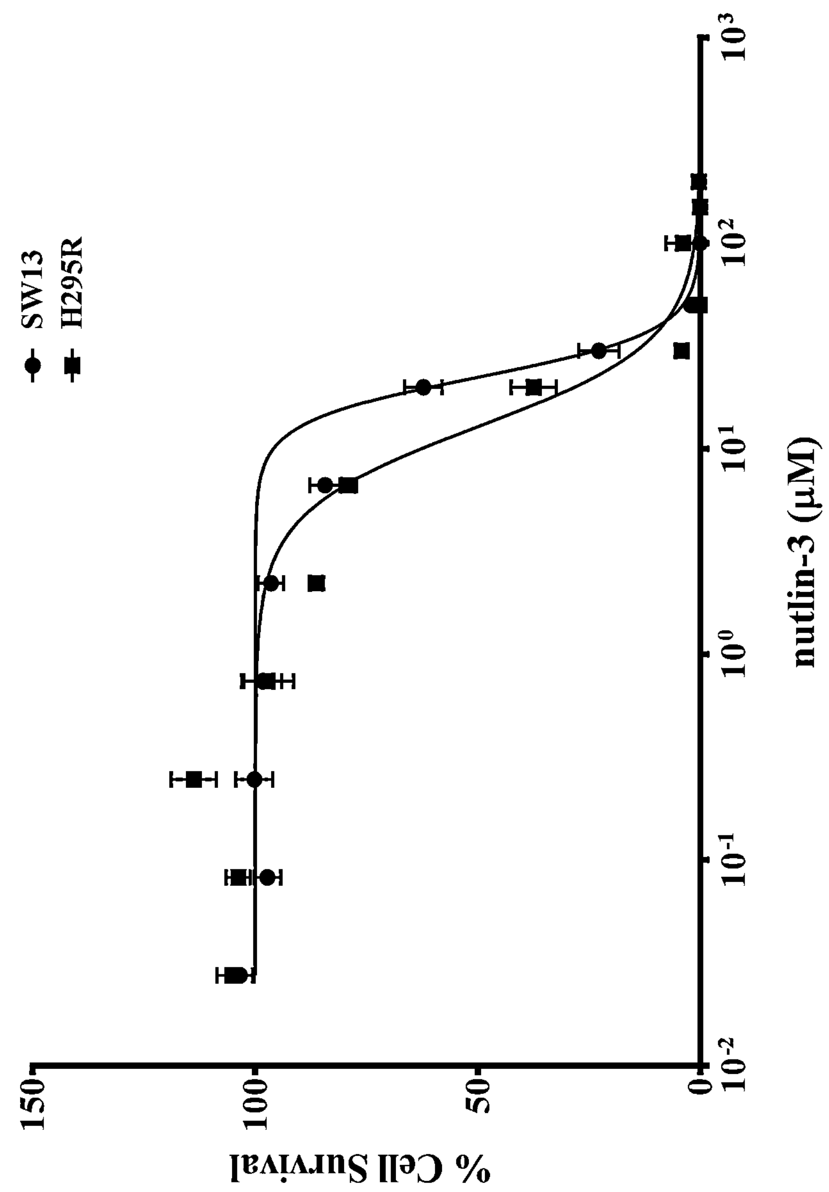
Figure 7:
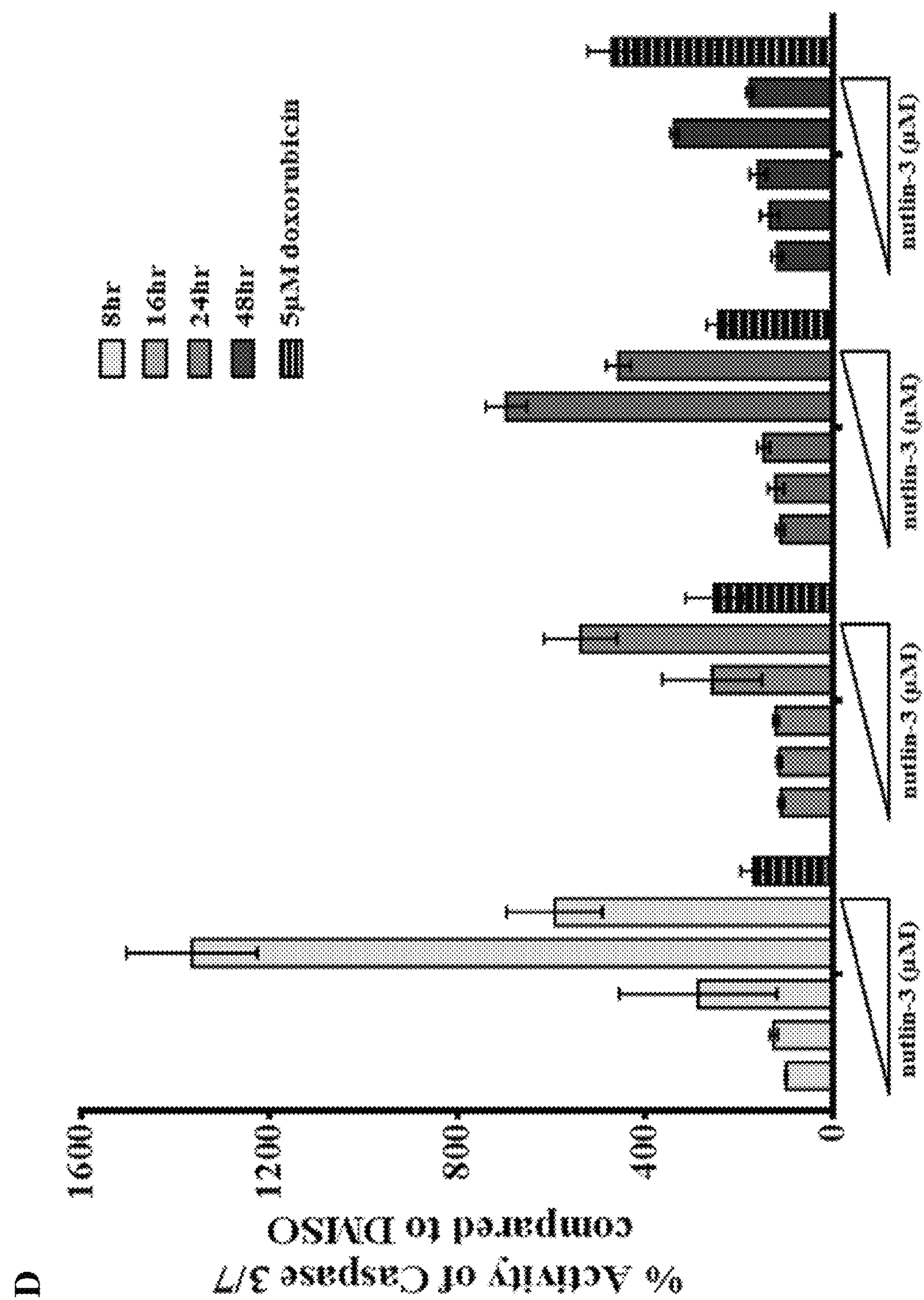
Figure 7:
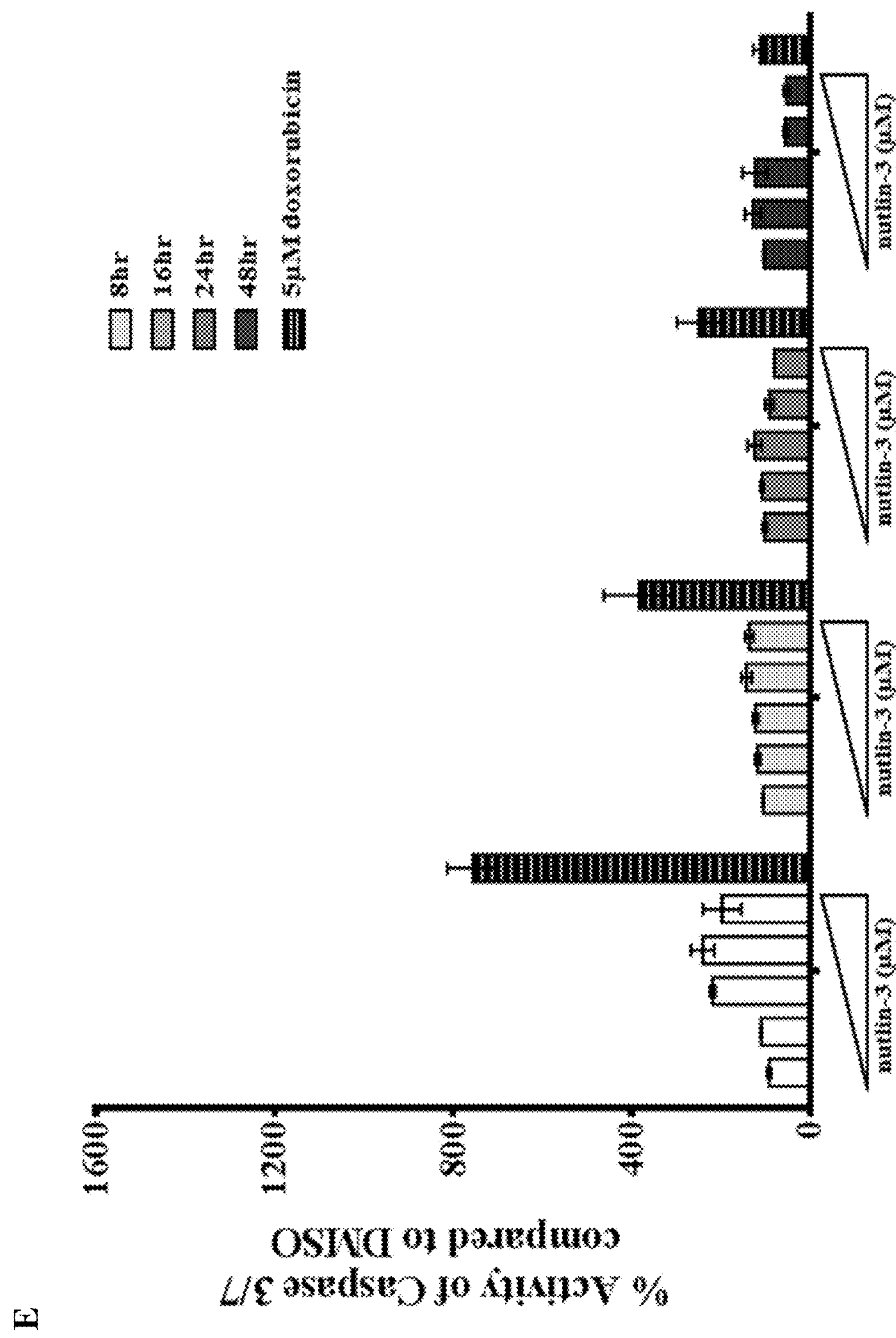

Although both PLK-1 and MDM2 regulate p53 activity independently, these two molecules also cooperate to modify p53 function. PLK-1 phosphorylates MDM2 at serine 260, stimulating the activity of MDM2 and increasing the turnover of p53. Dias, S. S. et al., *Polo-like kinase*-1 *phosphorylates MDM*2 *at Ser*260 *and stimulates MDM*2*-mediated p*53 *turnover* FEBS Lett. (583) 3543-3548 (2009). Inhibition of PLK-1 by BI-2536 does not affect the levels of the MDM2 protein (FIG. 7, panels A and B). Inhibiting MDM2 with the MDM2-specific inhibitor, nutlin-3, reduced viability of ACC cells through the restoration of p53 function. Treating both H295R and SW-13 cells with nutlin-3 decreased their cell viability (FIG. 7, panel C) and restored the apoptotic response in H295R cells, which have wild type p53 (FIG. 7, panels D and E).

Figure 8:
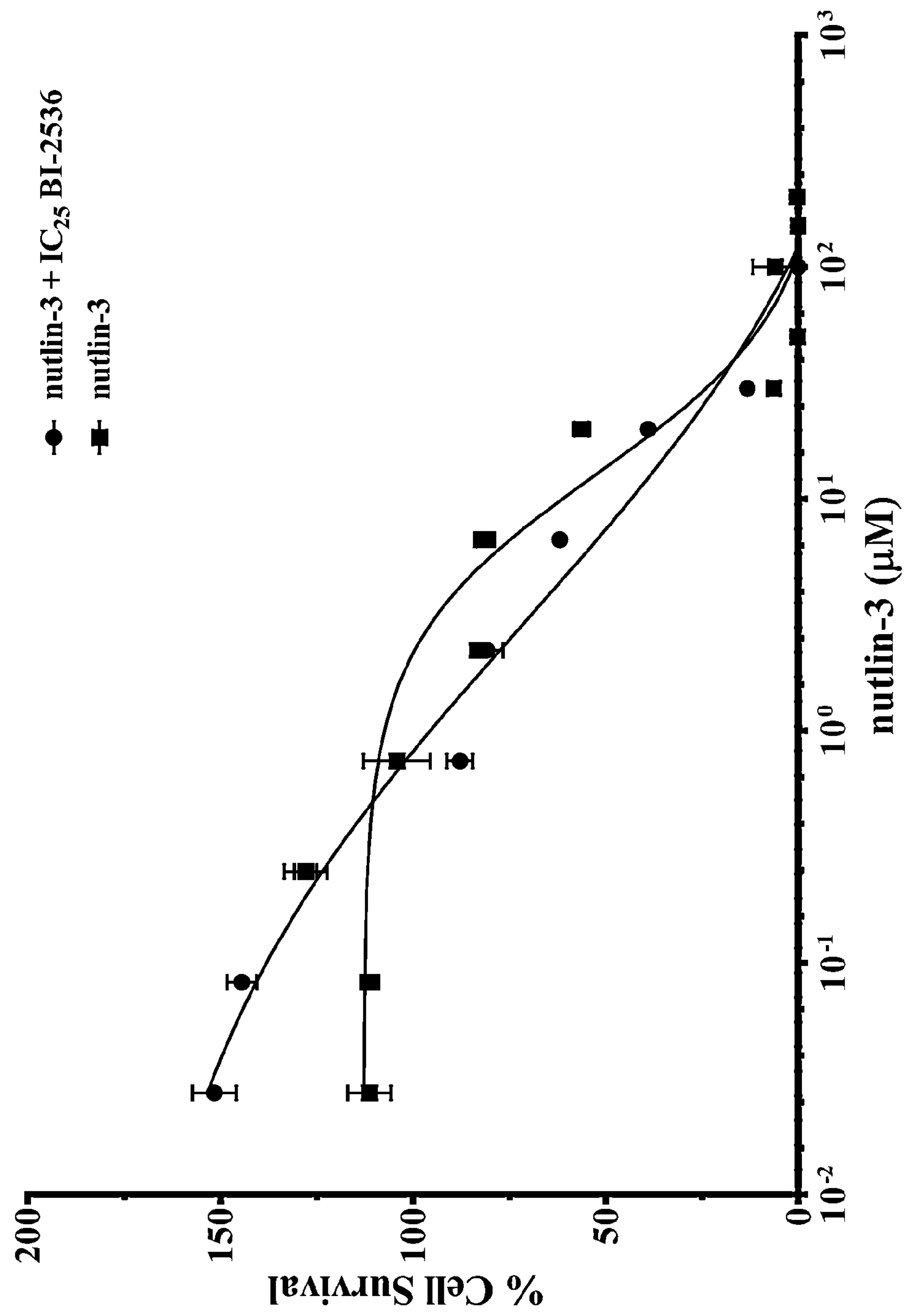
FIG. 8 illustrates the synergy of PLK-1 inhibition by BI-2536 with MDM2 inhibition by nutlin-3. Since PLK-1 plays a role in controlling p53 directly and indirectly via MDM2, the synergy of inhibition of PLK-1 and MDM2 inhibition was investigated. (A and B) Treatment of H295R (A) and SW-13 (B) cells with BI-2536 sensitized both the cell lines to nutlin-3 treatment. (C and D) Dual inhibition of PLK-1 and MDM2 resulted in an additive response in the H295R cells (C), with wild-type p53, whereas no additive apoptotic response was seen in the SW-13 cells (D) with mutant p53. Doxorubicin was used as a positive control for apoptosis. All experiments were performed in at least 3 technical replicates and data are represented as means with standard error.
Figure 8:
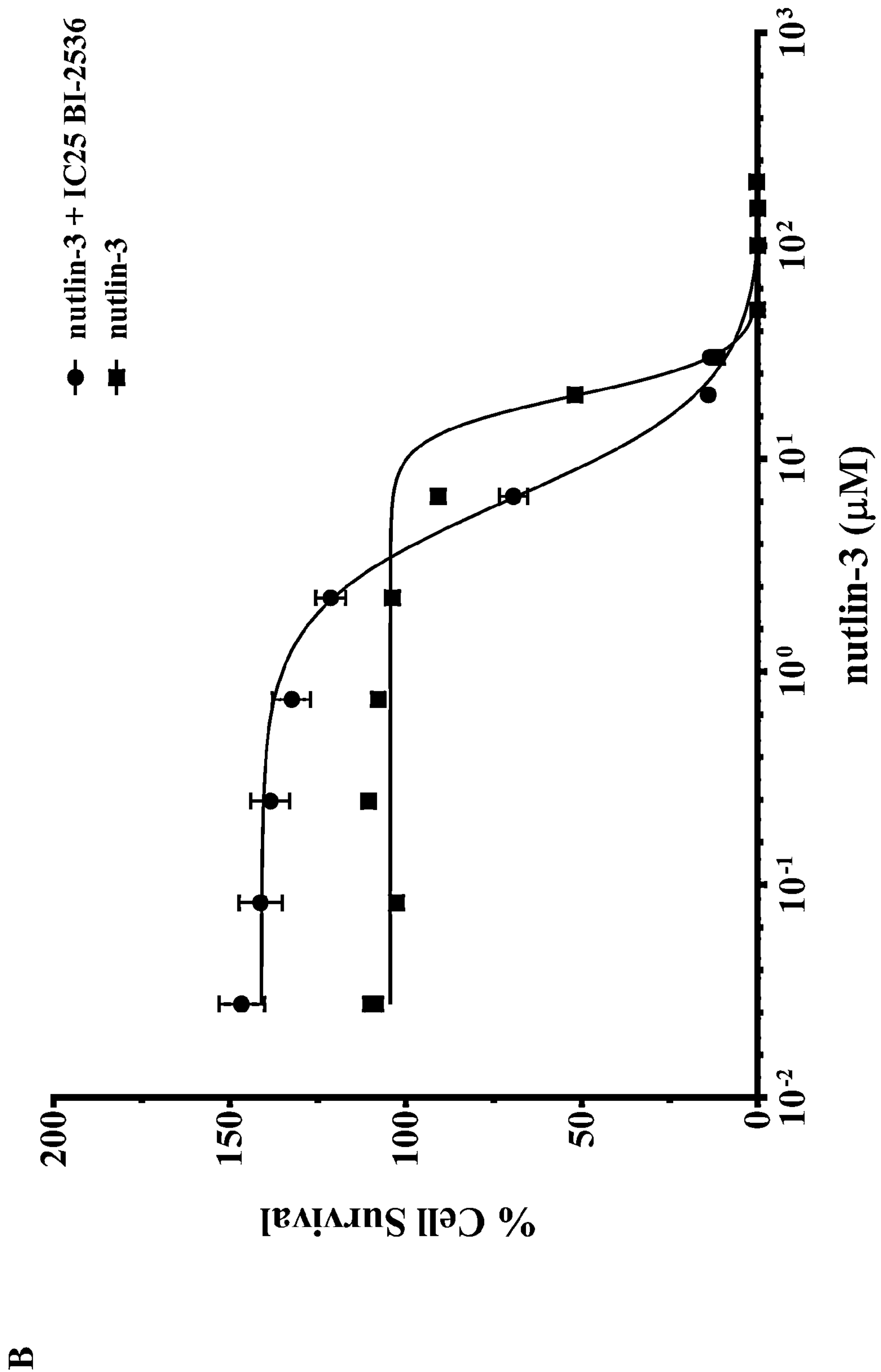
Figure 8:
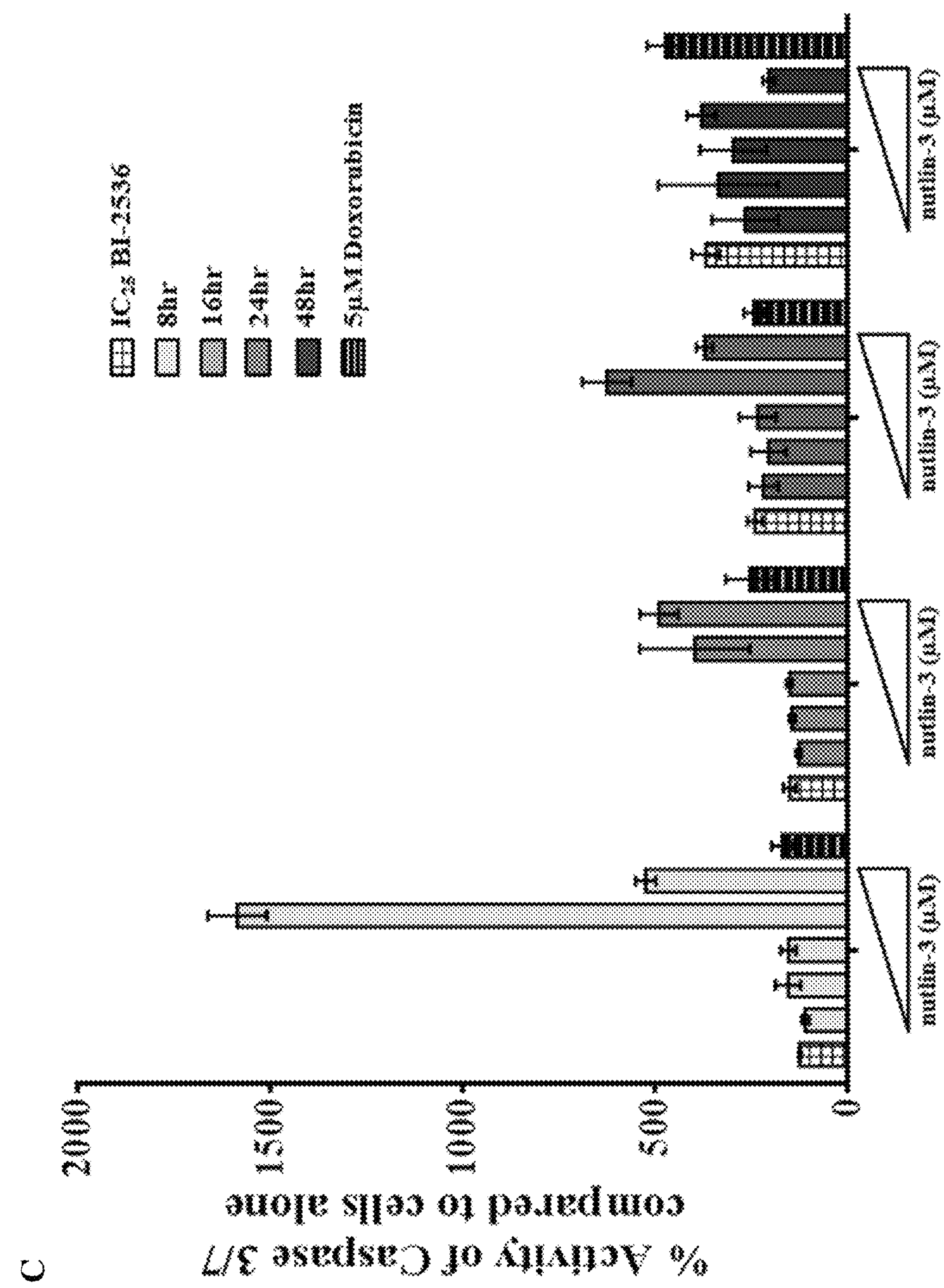
Figure 8:
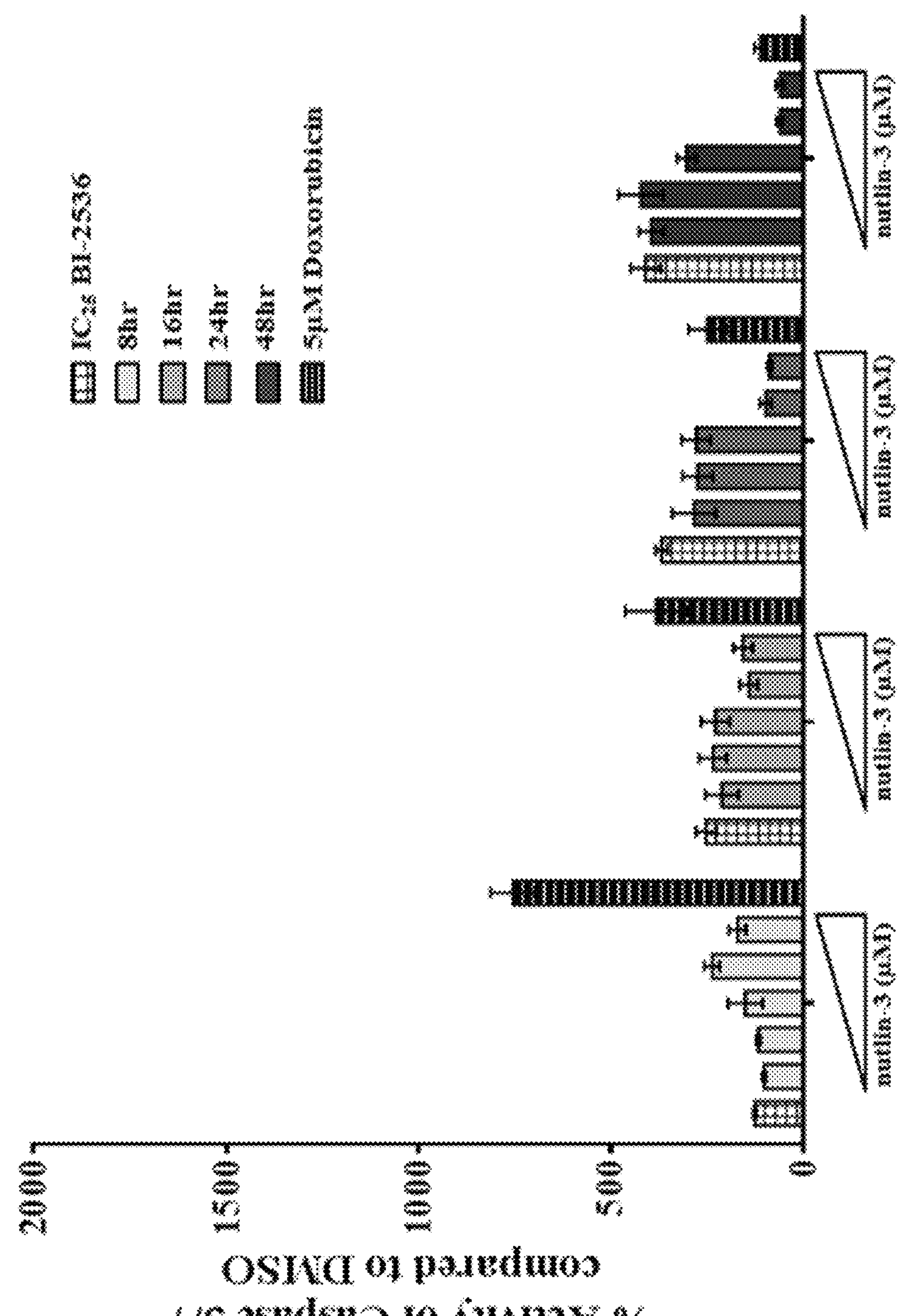

Given that PLK-1 directly modulates p53 functions as well as indirectly modulating MDM2 functions, the potential role of PLK-1 inhibition in sensitizing ACC cells to the effects of nutlin-3 was investigated. A decrease in the $IC_{50}$ values of nutlin-3 was observed when combined with the $IC_{25}$ concentration of BI-2536 (FIG. 8, panels A and B; Table 3). This effect was independent of p53 mutation status, as both ACC cell lines responded in a similar fashion. Combined inhibition of PLK-1 and MDM2 did not increase apoptotic response of SW-13 over that seen with BI-2536 alone, whereas an additive apoptotic response was observed in H295R cells with wild-type p53, which is responsive to MDM2 inhibition (FIG. 8, panels C and D; Table 3).

TABLE 3

IC$_{50}$ values of BI-2536 and nutlin-3 alone and in combination.

| Compound | H295R (IC$_{50}$ Value in μM) | SW-13 (IC$_{50}$ Value in μM) |
|---|---|---|
| BI-2536 | 0.0628 | 0.0094 |
| nutlin-3 | 12.75 | 19.78 |
| nutlin-3 + BI-2536 | 2.838 | 6.502 |
| Combination Index | 0.22 | 0.33 |

What is claimed is:

1. A method of treating endocrine cancer in a subject, the method comprising the steps of:

receiving a sample of a tumor from the subject;

adding a reagent to a mixture comprising the sample, the reagent specifically binds to a first marker having a sequence selected from the group consisting of SEQ ID NO. 1, SEQ ID NO. 2, SEQ ID NO. 4, and SEQ ID NO. 5;

subjecting the mixture to conditions that allow detection of binding of the reagent to the first marker;

assessing an expression level of the first marker in the sample based on a level of binding of the reagent to the marker; and detecting reduced expression of the first marker in the sample as compared to a control sample and administering a therapeutically effective amount of a pharmaceutical composition comprising a mitotic catastrophe inducing composition to the subject.

2. The method of claim 1, wherein the endocrine cancer is a cancer of an adrenal gland.

3. The method of claim 2, wherein the endocrine cancer is a malignant cancer of the adrenal gland.

4. The method of claim 3, wherein the malignant cancer of the adrenal gland is adrenocortical carcinoma.

5. The method of claim 1, wherein the reagent is selected from the group consisting of an oligonucleotide and an antibody.

6. The method of claim 1, wherein the mitotic catastrophe inducing composition is a mouse double minute 2 (MDM2) inhibitor.

7. The method of claim 1, wherein the mitotic catastrophe inducing composition is a PLK1 inhibitor selected from the group consisting of BI-2536, cyclapolin 9, GW 843682X, TC-S 7005, Wortmannin, NMS-P937, and GSK461364A.

8. The method of claim 1 and further comprising determining if a second marker having a sequence substantially similar to a sequence selected from the group consisting of SEQ ID NO. 3 and SEQ ID NO. 6 comprises a p53 wild type sequence in the subject being treated.

9. A method of treating a subject with a caspase cascade defect, the method comprising the steps of:

Identifying a subject with a caspase cascade defect comprising detecting reduced expression of a first marker having a sequence selected from the group consisting of SEQ ID NO:1, SEQ ID NO:2, SEQ ID NO:4, and SEQ ID NO:5 in a sample from the subject, relative to a control sample; and administering a therapeutically effective amount of mitotic catastrophe inducing composition to the subject with a caspase cascade defect.

10. The method of claim 9, wherein the mitotic catastrophe inducing composition is a PLK1 inhibitor selected from the group consisting of B1-2536, cyclapolin 9, GW 843682X, TC-S 7005, Wortmannin, NMS-P937, and GSK461364A.

11. The method of claim 10, wherein the PLK1 inhibitor is BI-2536.

12. The method of claim 9, wherein mitotic catastrophe inducing composition is an MDM2 inhibitor selected from the group consisting of a nutlin, caylin-1, HLI 373, caylin-2, JNJ 26854165, NSC 66811, and trans-4-Iodo, 4'-boranyl-chalcone.

13. The method of claim 12, wherein the MDM2 inhibitor is a nutlin.

14. The method of claim 13, wherein the nutlin is nutlin-3.

* * * * *

SEQUENCE LISTING

<160> NUMBER OF SEQ ID NOS: 6

<210> SEQ ID NO 1
<211> LENGTH: 2750
<212> TYPE: DNA
<213> ORGANISM: Homo sapiens

<400> SEQUENCE: 1
gtgctctgag tttttggttt ctgtttcacc ttgtgtctga gctggtctga aggctggttg 60
ttcagactga gcttcctgcc tgcctgtacc ccgccaacag cttcagaaga aggagcagcc 120
cctgggtgcg tccactttct gggcacgtga ggttgggcct tggccgcctg agcccttgag 180
ttggtcactt gaaccttggg aatattgaga ttatattctc ctgcctttta aaaagatgga 240
cttcagcaga aatctttatg atattgggga acaactggac agtgaagatc tggcctccct 300
caagttcctg agcctggact acattccgca aaggaagcaa gaacccatca aggatgcctt 360
gatgttattc cagagactcc aggaaaagag aatgttggag gaaagcaatc tgtccttcct 420
gaaggagctg ctcttccgaa ttaatagact ggatttgctg attacctacc taaacactag 480
aaaggaggag atggaaaggg aacttcagac accaggcagg gctcaaattt ctgcctacag 540
ggtcatgctc tatcagattt cagaagaagt gagcagatca gaattgaggt cttttaagtt 600
tcttttgcaa gaggaaatct ccaaatgcaa actggatgat gacatgaacc tgctggatat 660
tttcatagag atggagaaga gggtcatcct gggagaagga aagttggaca tcctgaaaag 720
agtctgtgcc caaatcaaca agagcctgct gaagataatc aacgactatg aagaattcag 780
caaaggggag gagttgtgtg gggtaatgac aatctcggac tctccaagag aacaggatag 840
tgaatcacag actttggaca aagtttacca aatgaaaagc aaacctcggg gatactgtct 900
gatcatcaac aatcacaatt ttgcaaaagc acgggagaaa gtgcccaaac ttcacagcat 960
tagggacagg aatggaacac acttggatgc aggggctttg accacgacct ttgaagagct 1020
tcattttgag atcaagcccc acgatgactg cacagtagag caaatctatg agattttgaa 1080
aatctaccaa ctcatggacc acagtaacat ggactgcttc atctgctgta tcctctccca 1140
tggagacaag ggcatcatct atggcactga tggacaggag gcccccatct atgagctgac 1200
atctcagttc actggtttga agtgcccttc ccttgctgga aaacccaaag tgtttttat 1260 tcaggcttgt caggggggata actaccagaa aggtatacct gttgagactg attcagagga 1320
gcaaccctat ttagaaatgg atttatcatc acctcaaacg agatatatcc cggatgaggc 1380
tgactttctg ctggggatgg ccactgtgaa taactgtgtt tcctaccgaa accctgcaga 1440
gggaacctgg tacatccagt cactttgcca gagcctgaga gagcgatgtc ctcgaggcga 1500
tgatattctc accatcctga ctgaagtgaa ctatgaagta agcaacaagg atgacaagaa 1560
aaacatgggg aaacagatgc ctcagcctac tttcacacta agaaaaaaac ttgtcttccc 1620
ttctgattga tggtgctatt ttgtttgttt tgttttgttt tgttttttg agacagaatc 1680

```
tcgctctgtc gcccaggctg gagtgcagtg gcgtgatctc ggctcaccgc aagctccgcc   1740

tcccgggttc aggccattct cctgcctcag cctcccgagt agctgggact acaggggccc   1800

gccaccacac ctggctaatt ttttaaaaat atttttagta gagacagggt ttcactgtgt   1860

tagccagggt ggtcttgatc tcctgacctc gtgatccacc cacctcggcc tcccaaagtg   1920

ctgggattac aggcgtgagc caccgcgcct ggccgatggt actatttaga tataacacta   1980

tgtttattta ctaattttct agattttcta ctttattaat tgttttgcac tttttttataa   2040

gagctaaagt taaataggat attaacaaca ataacactgt ctcctttctc ttatgcttaa   2100

ggctttggga atgtttttag ctggtggcaa taaataccag acacgtacaa aatccagcta   2160

tgaatataga gggcttatga ttcagattgt tatctatcaa ctataagccc actgttaata   2220

ttctattaac tttaattctc tttcaaagct aaattccaca ctaccacatt aaaaaaatta   2280

gaaagtagcc acgtatggtg gctcatgtct ataatcccag cactttggga ggttgaggtg   2340

ggaggattgc ttgaacccaa gaggtcaagg ctgcagtgag ccatgttcac accgctgcac   2400

tcaagcttgg gtgacagaac aagaccccgt ctcaaaaaaa attttttttt taataaaaca   2460

aaatttgttt gaaatctttt aaaaattcaa atgattttta caagttttaa ataagctctc   2520

cccaaacttg ctttatgcct tcttattgct tttatgatat atatatgctt ggctaactat   2580

atttgctttt tgctaacaat gctctggggt ctttttatgc atttgcattt gctctttcat   2640

ctctgcttgg attattttaa atcattagga attaagttat ctttaaaatt taagtatctt   2700

ttttcaaaaa catttttttaa tagaataaaa tataatttga tcttattaaa              2750
```

<210> SEQ ID NO 2
<211> LENGTH: 3038
<212> TYPE: DNA
<213> ORGANISM: Homo sapiens

<400> SEQUENCE: 2

```
ttggccctgg gggcggggcg aggcgcagag gtgcgtcctg agggcggggc ggtgacgcaa     60

gagcgactcc tgggggcggg gcgaggcctt ggagatgcgt ccggaggcgg tggggagcga    120

agactgaccc ggggccgtga cgcgggggca ggccctgggg cgggggcggg tcctggggac    180

tggggcgggc ggccgaggcc cggaagcgga ctgaggcggc ctggagtctt agttggctac    240

tcgccatgga cgaagcggat cggcggctcc tgcggcggtg ccggctgcgg ctggtggaag    300

agctgcaggt ggaccagctc tgggacgccc tgctgagccg cgagctgttc aggccccata    360

tgatcgagga catccagcgg gcaggctctg gatctcggcg ggatcaggcc aggcagctga    420

tcatagatct ggagactcga gggagtcagg ctcttccttt gttcatctcc tgcttagagg    480

acacaggcca ggacatgctg gcttcgtttc tgcgaactaa caggcaagca gcaaagttgt    540

cgaagccaac cctagaaaac cttaccccag tggtgctcag accagagatt cgcaaaccag    600

aggttctcag accggaaaca cccagaccag tggacattgg ttctggagga tttggtgatg    660

tcggtgctct tgagagtttg aggggaaatg cagatttggc ttacatcctg agcatggagc    720

cctgtggcca ctgcctcatt atcaacaatg tgaacttctg ccgtgagtcc gggctccgca    780

cccgcactgg ctccaacatc gactgtgaga agttgcggcg tcgcttctcc tcgctgcatt    840

tcatggtgga ggtgaagggc gacctgactg ccaagaaaat ggtgctggct ttgctggagc    900

tggcgcagca ggaccacggt gctctggact gctgcgtggt ggtcattctc tctcacggct    960

gtcaggccag ccacctgcag ttcccagggg ctgtctacgg cacagatgga tgccctgtgt   1020
```

```
cggtcgagaa gattgtgaac atcttcaatg ggaccagctg ccccagcctg ggagggaagc   1080
ccaagctctt tttcatccag gcctgtggtg gggagcagaa agaccatggg tttgaggtgg   1140
cctccacttc ccctgaagac gagtcccctg gcagtaaccc cgagccagat gccaccccgt   1200
tccaggaagg tttgaggacc ttcgaccagc tggacgccat atctagtttg cccacaccca   1260
gtgacatctt tgtgtcctac tctactttcc caggttttgt ttcctggagg gaccccaaga   1320
gtggctcctg gtacgttgag accctggacg acatctttga gcagtgggct cactctgaag   1380
acctgcagtc cctcctgctt agggtcgcta atgctgtttc ggtgaaaggg atttataaac   1440
agatgcctgg ttgctttaat ttcctccgga aaaaactttt ctttaaaaca tcataaggcc   1500
agggcccctc accctgcctt atcttgcacc ccaaagcttt cctgccccag gcctgaaaga   1560
ggctgaggcc tggactttcc tgcaactcaa ggactttgca gccggcacag ggtctgctct   1620
ttctctgcca gtgacagaca ggctcttagc agcttccaga ttgacgacaa gtgctgaaca   1680
gtggaggaag agggacagat gaatgccgtg gattgcacgt ggcctcttga gcagtggctg   1740
gtccagggct agtgacttgt gtcccatgat ccctgtgttg tctctagagc agggattaac   1800
ctctgcacta ctgacatgtg gggccaggtc accctttgct gtgaggctgt cctgtacatt   1860
gtgggatgtt cagcactgtc ccttgcctca atgccagtaa cgcgtcttcc tgagtggtgc   1920
caaacaaaaa ggttctcagg tgttgccaaa tatgtcctgg ggtataaaac tttcctcgcc   1980
tgacaaccac tggtctgtag ggatttttgg ctacacacaa accagtatcg ctcatagatc   2040
agcaaaccgg ggcctactag agtctgaaca gctgtaatct atgaattcta agtgaaattt   2100
taaaaattgt taatttttcc tatattgcat taattttaaa aaataaatct gaggcaaata   2160
tggactctct tttgcctatt tcttccctca ttttgctcca actctttctt cttccttaca   2220
aaagagactt ttgctttttt cgaaacattt ccccatgttt ttctggggtc tcgctatgtt   2280
gcccaggctg gtctcaaact cctgggctca agtgaccctc ccaagtagct cttactacag   2340
gcgtgcacca ttgcacccag ccccatttat tcatgtctta tttcacttga tccttatccc   2400
atcccaggaa ggcaacaagg gtgagaaccc tgtgctcagg gaggttaggt ctcttgtcca   2460
agggaaaacg attatccaga gaagagacct ggccagaacc tgggtcccct gagtcctagc   2520
catgcttccc atgtgcctta cttgctgaag cacccccgga ctgcagtgtg aacgtgctgt   2580
gcaatagtga cacgctgggc ttccccacaa ggctccaccc tgaggtcttt taagctgtcc   2640
ttatgccagc ctatttcttg ctttttgggc cttttttttt ggagataggg tctcactctg   2700
tcgcccaggc tggagtgcaa tgacgcaatc ttggcttatt gcagtctcga cctcctgggc   2760
tcaagagatc cttccacctc agccacctga gtagcttgga ctacaggtgt gcaccacctc   2820
tcccagttaa tttttgtatt tttagtagag acagagttat gccatgttac tcaggctggt   2880
cttgaactcc tggactcaag cgatcagcct gccttagcct cccaaagtgc aggggttaca   2940
ggcttgagcc attgcgcctg acctatttct ggttcttagg gccctggatg ttaggatgga   3000
tttctgaatt aataataata ataaaaccct catcaaga                           3038
```

<210> SEQ ID NO 3
<211> LENGTH: 32772
<212> TYPE: DNA
<213> ORGANISM: Homo sapiens

<400> SEQUENCE: 3

```
ctccttggtt caagtaattc tcctgcctca gactccagag tagctgggat tacaggcgcc     60
cgccaccacg cccagctaat tttttgtatt tttaatagag atggggtttc atcatgttgg    120
```

```
ccaggctggt ctcgaactcc tgacctcagg tgatccacct gcctcagcct cccaaagtgc    180
tgggattaca ggagtcagcc accgcaccca gccccaacta atttttgtat ttgagtagag    240
acagggtttt accatgttgg ccaggctggt ctaaaactct tcacctcagg tgatccaccc    300
atctcagcct cccaaagtgt tgggattaca ggcgtgagcc accgtgcctg gccctggatt    360
tcactcttgc ccacccataa accattcact cttctgtttt aaaactctct tggccgggcg    420
cagtggctca tgcctgtaat cccagcactt tgggaggcca aggtgggcag atcacaaggt    480
caggagttcg agaccagcct ggccaatatg atgaaccccc catctctact aaaaaaatac    540
aaaaaaatta gccgggtgtg gtggcacatg cctgtaatcc cagctactcg gaaggttgag    600
gcaggagaat cacttaaacc tgggaggcgg aggttgcggt gagctgagat ggtgccactg    660
cactccagcc tggacaacag agcaagactc tgtctcaaac aaacaaacaa aaaaaacctc    720
tctcatggcc tggcatggtg gctcacgcct gtaatcctag cactttggaa ggctgaggca    780
ggtggatcac ctgaggtcag gagtttgaga ccagccaggc caacgtggca aaacctgtct    840
ctactaaaaa tacaaaaatt aagccaggcg cggtggctca tgcctataat cccagcactt    900
tgggaggccg agaccggcgg atcaaatgtc aggagtacga gaccatcctg gccaatatgg    960
taaaaccccg tctctattta aaaaaataca aaaattagct gggcatggtg gcgggtgcct   1020
gtaatcccag ctactcggga ggctgaggca ggagaatcgc ttgaatccag gaggcagagg   1080
ttgcagtgag ccgagatcac gccattgcac tccagcctgg gcgacagagc aagactcgtc   1140
tcaaaaaaaa aaaaaaaaca cctctctcat gacttcccaa ataaactcca aatgccttac   1200
ccataagaac caacacgacg tggctgctct tctctgtcct cacccctctg tccccctcac   1260
ttgcctcagt ctggctatac cagcattctg ggtttttgt tttgtgtttg tttgtttgtt    1320
tgtttgtttg tttgtttgtt ttgggatgga gtctcactct gtcacccagg ctggagtgca   1380
gtgacatgat cttggctcac tgcaacctcc atctcctggg ttcaaatgat tcttctgctt   1440
cagcctctca agtagctggg attacaggca cccaccatca cacccagcta atttttgtat   1500
ttttgtagag atgaggtttt gccatgttgg ccaggctggt ctcaaactct tgacctcagg   1560
tgatctgccc acctcagcct cccaaagtgc tgggattaca ggtgtgagcc actgagccca   1620
gtctgttttg ttgtttttttg agatggagtc tcactctgtc gcccaggctg gagtgcagtg   1680
gtacaatttt gtctgactgc agcctccacc tcctgagttt aagagattct cctgcctcag   1740
ccacacaagt agctgggatt acaggcgcgt gccaccacat gcgtctaatt ttggtatttt   1800
tagtagcgat ggggttttgc catattggcc aggctggtct cgaactcctg gcctcaagtg   1860
atctgcacac ctcggcctcc tgagtagctg ggattacagg cgtgagccac catgcagggc   1920
ctttctggtc ttttaacgca caaagctatt tcccagttct gggtgtttat agtatcattg   1980
ccagttcctg gaaagctctt tccagaagcc ttcacatgac tgatccctta tcctccttca   2040
ggtcttagct caaatgcctc cttttcagag agctccttcc tgaccatttt atgcaatgtg   2100
ctttcctcta gttagtctct cttcattctg tgtatttcct tcagagcatt tatcatcatc   2160
ttggtcctga tgcttgctgg tttacatgtt tgttgtctgt ctcccacaca gaaagcaaac   2220
cagcccttca tctgtcttgt ccaccacttt atcccagcac agtgactaac atatatcagt   2280
agtcaatcaa taaatagcta taagccaggc acggtgactc acacctgtga tccccgcact   2340
ttgggaggcc aaggtgggcg gatcctctga ggtcaggaat ttgatatcag cctgcccaac   2400
atggcgaaac cccgtctcta ctaaaactat aaaaattagt cgagtgtgat ggcgtgcgcc   2460
```

```
tgtaatacca gctacttgtg aggctgaggc aggagaatcg cttgaacccg ggaggcagag   2520
gttgcagtga gccgagatca caccacagca ctccagcctg ggtgacagag caagaccttg   2580
tctcaaaaaa ataagaaata gaaatatata tatgctgcca caagaaattc actacttttt   2640
agcaaaaaac acagattcct aattaaagaa aggggaaacc tctctctaaa taacttcaga   2700
attcggggca gaaaacgcta catgtggaaa ctcgtcttga aaaacagtcc cgtttgtgaa   2760
caggaaacac ttggactaca ctttttccat ctccacgaag gacttaaatg tgcagcattg   2820
atgaagaggc agttagcccc agtccttacc atttctgcat attccacctg ctccccctca   2880
tggtacagct ctgggggcag gttataaatt cgcaagatgt tatcagcact attggtcaag   2940
atgcaggaac cgtcaggagc cctagaaaca ggggagagtt agaaagctgg ccagacctat   3000
gcttttcaag tgtagggcta gggctgagcc tgcctctggg gtaggtaagc ccccctgaat   3060
ccttgaggga agtagaagac acaaactgct agataaaatg taagctcagt ctaaaagggc   3120
tacgtgccgc ttctcccagc tctggggcat ccctctccta gaaaactgga ctgttttaca   3180
gtgaaaatct cgggggtggt cagctccctg ccccgttgtt atccttacca cttacagcct   3240
ttcaagaagt tctcaggttg ggtgctgaac tctgaccagg aaccactgag aaatcgaggc   3300
agctgggaga agctgtagtt ccaagcgctg aaaggaagat gggggacaat aaacctgggt   3360
cgccaagcaa agggggcaga ggcctggaga agtgggtctc aggaccagag gacagatcga   3420
cctcacactt catctcccca gactccacac tccactgcca tcaccactta cgtgtctccc   3480
tcgtcctctg cagcgggttc cccagaggta tcttccatgg cttttccaga ccccaactct   3540
ggcccgttcg cttcttcttc agaaaggctc ccgtttgctt cttctgcagg aaggcttgta   3600
ttttcagaaa gttcttgctc ctcgattcga ggactcaact cactagggga accaaactct   3660
gtttccaggg gagtggagag agaaactggg tccccctccc gtagctcctg ggacacagct   3720
gagccagcca caggatctgg ggacaaccgg ggcggatccc ccctttcggg aggcggtggc   3780
atcagttcag agtccgcatt tttattcatc ggggaagcgt ggggagaagg atgggctgga   3840
gctgggtcct ggtctgaagg acagcagtcc ggagctaacg gttgagtctc caaagtcttc   3900
atactgcaga ggaagcacag cggagattag cctcagccag gatggcttcg aagttctcag   3960
ggatccgacg cagagctaaa gaaacccacc tgtgcttccc tcctcttctg ggagtaggca   4020
gaagactccc gggaggagag gcgaacagcg gacgccaatt cttttgaaag cactgtgttc   4080
cttagcaccg cgggtcgcta cgggcctctt gctgtcgcgg gatttcggtc caccttccga   4140
ttgggccgcc gcatcccgga tcagatttcg cgggcgaccc acggaacccg cggagccggg   4200
acgtgaaagg ttagaaggtt tcccgttccc atcaagccct agggctcctc gtggctgctg   4260
ggagttgtag tctgaacgct tctatcttgg cgagaagcgc ctacgctccc cctaccgagt   4320
cccgcggtaa ttcttaaagc acctgcaccg cccccccgcc gcctgcagag ggcgcagcag   4380
gtcttgcacc tcttctgcat ctcattctcc aggcttcaga cctgtctccc tcattcaaaa   4440
aatatttatt atcgagctct tacttgctac ccagcactga tataggcact caggaataca   4500
acaatgaata agatagtaga aaaattctat atcctcataa ggcttacgtt tccatgtact   4560
gaaagcaatg aacaaataaa tcttatcaga gtgataaggg ttgtgaagga gattaaataa   4620
gatggtgtga tataaagtat ctgggagaaa acgttagggt gtgatattac ggaaagcctt   4680
cctaaaaaat gacattttaa ctgatgagaa gaaaggatcc agctgagagc aaacgcaaaa   4740
gctttcttcc ttccaccctt catatttgac acaatgcagg attcctccaa aatgatttcc   4800
accaattctg ccctcacagc tctggcttgc agaattttcc accccaaaat gttagtatct   4860
```

```
acggcaccag gtcggcgaga atcctgactc tgcaccctcc tccccaactc catttccttt   4920
gcttcctccg gcaggcggat tacttgccct tacttgtcat ggcgactgtc cagctttgtg   4980
ccaggagcct cgcaggggtt gatgggattg ggttttccc ctcccatgtg ctcaagactg   5040
gcgctaaaag ttttgagctt ctcaaaagtc tagagccacc gtccagggag caggtagctg   5100
ctgggctccg ggacactttt gcgttcgggc tgggagcgtg ctttccacga cggtgacacg   5160
cttccctgga ttgggtaagc tcctgactga acttgatgag tcctctctga gtcacgggct   5220
ctcggctccg tgtattttca gctcgggaaa atcgctgggg ctgggggtgg ggcagtgggg   5280
acttagcgag tttgggggtg agtgggatgg aagcttggct agagggatca tcataggagt   5340
tgcattgttg ggagacctgg gtgtagatga tggggatgtt aggaccatcc gaactcaaag   5400
ttgaacgcct aggcagagga gtggagcttt ggggaacctt gagccggcct aaagcgtact   5460
tctttgcaca tccacccggt gctgggcgta gggaatccct gaaataaaag atgcacaaag   5520
cattgaggtc tgagactttt ggatctcgaa acattgagaa ctcatagctg tatattttag   5580
agcccatggc atcctagtga aaactggggc tccattccga aatgatcatt tgggggtgat   5640
ccggggagcc caagctgcta aggtcccaca acttccggac ctttgtcctt cctggagcga   5700
tctttccagg cagcccccgg ctccgctaga tggagaaaat ccaattgaag gctgtcagtc   5760
gtggaagtga gaagtgctaa accaggggtt tgcccgccag gccgaggagg accgtcgcaa   5820
tctgagaggc ccggcagccc tgttattgtt tggctccaca tttacatttc tgcctcttgc   5880
agcagcattt ccggtttctt tttgccggag cagctcacta ttcacccgat gagaggggag   5940
gagagagaga gaaaatgtcc tttaggccgg ttcctcttac ttggcagagg gaggctgcta   6000
ttctccgcct gcatttcttt ttctggatta cttagttatg gcctttgcaa aggcaggggt   6060
atttgttttg atgcaaacct caatccctcc ccttctttga atggtgtgcc ccacccccgcg   6120
ggtcgcctgc aacctaggcg gacgctacca tggcgtgaga cagggaggga aagaagtgtg   6180
cagaaggcaa gcccggaggt attttcaaga atgagtatat ctcatcttcc cggaggaaaa   6240
aaaaaaagaa tgggtacgtc tgagaatcaa attttgaaag agtgcaatga tgggtcgttt   6300
gataatttgt cggaaaaaca atctacctgt tatctagctt tgggctaggc cattccagtt   6360
ccagacgcag gctgaacgtc gtgaagcgga aggggcgggc ccgcaggcgt ccgtgtggtc   6420
ctccgtgcag ccctccggcc cgagccggtt cttcctggta ggaggcggaa ctcgaattca   6480
tttctcccgc tgccccatct cttagctcgc ggttgtttca ttccgcagtt tcttcccatg   6540
cacctgccgc gtaccggcca ctttgtgccg tacttacgtc atctttttcc taaatcgagg   6600
tggcatttac acacagcgcc agtgcacaca gcaagtgcac aggaagatga gttttggccc   6660
ctaaccgctc cgtgatgcct accaagtcac agaccctttt catcgtccca gaaacgtttc   6720
atcacgtctc ttcccagtcg attcccgacc ccacctttat tttgatctcc ataaccattt   6780
tgcctgttgg agaacttcat atagaatgga atcaggctgg gcgctgtggc tcacgcctgc   6840
actttgggag gccgaggcgg gcggattact tgaggatagg agttccagac cagcgtggcc   6900
aacgtggtga atccccgtct ctactaaaaa atacaaaaat tagctgggcg tggtgggtgc   6960
ctgtaatccc agctattcgg gagggtgagg caggagaatc gcttgaaccc gggaggcaga   7020
ggttgcagtg agccaagatc gtgccactac actccagcct gggcgacaag aacgaaactc   7080
cgtctcaaaa aaaagggggg aatcatacat tatgtgctca tttttgtcgg gcttctgtcc   7140
ttcaatgtac tgtctgacat tcgttcatgt tgtatatatc agtattttgc tccttttcat   7200
```

```
ttagtatagt ccatcgattg tatatccgtc cttttgatgg ccttttgagt tgtttcccat   7260
ttgcggttat gaaataaagc tgctataaac attcttgtac aattcttttt gtgatcatat   7320
gttttcgtgt ttcttggaga aatacttagg aggggaattg cgagtttgga agtaaaaagt   7380
agctgtattt tgaacttttt cagaagctct gagttttcca gagcggttgt accattttac   7440
actccaacta gcaaggtatg ggagttatta tggttgtgcc acagccttcc ggacattagg   7500
tattgtcagt ctttctaatg tggtatatcc ttgtggttgt aatttacagt tctctattga   7560
ctaaggatgt tcagcatttt ttcatgtgcc tattggccat tcgtattttg tttgtaaagt   7620
agctcttcga gtcttttacc tgttattttg gtttttttgtt tgtttttatt gttcagttgt   7680
gggactgctt tatacattct ggatacaagt cctttatcag atccatgtgt cgtgaatgtt   7740
ttcttctgat ctgttgcttg cctatttgtt tgctttacag agtttacagt atcttaagag   7800
gagtggattt atcttttttta tgttcagtat ttgccttgtc ctgtttagga catctttttt   7860
ttttttttta accccagggt catgaagata ttatcttaca ttttctttta ggacctttat   7920
ggttgtaagt tttacagtaa ggtccttgag ccattaatta attcttaaaa ttaattgttt   7980
atggtgtgag gtgtaggagt cagtctctgg tatctttcct gtatggaaat ccagttattc   8040
tgtctccact tgttgaaata ggcttccttt ctctactgaa tgcttttaat tttaattatt   8100
ttacagttgg agtatagggc taccatttta gtgctatttt ctttttttct ttgttaattt   8160
ttgagacagg gactcacact gttgcccagg ctagagtaca atggcacaat caaggcttac   8220
tgcagcctcg aacccctggg ctcaagcagt cctctagcag cctcacgagt agctgggatt   8280
actccaccac acccagctaa ctattttatt tttttgtatt gacaggatct cactatgttg   8340
cccaggctgg tctcaaactg ctggcctcaa gctttcatcc catctcggcc tcccaaagtg   8400
ctgggattac aggtgtgagc caccatgcct gacctcttag tgctattttc tatttatctc   8460
ctctgttctc tgctctcttt aaacgttgga ggaagaaaca gtacccatct tacacaaact   8520
cttcagaaaa cagaggaaca gactgggcgc ggtggctcat acctgtaatc tcagcacttt   8580
ggtacgctga ggcaggggat catttgaggt cgggagttcg agaccagcct ggccaacacg   8640
gcgaaacccc atctctacta aaaatacaaa aagtagctag gcgtggtgac acatacctgt   8700
aatgccagtt actcaggagg ctgaggcaca agaatccctt gaacctggga agcggaggtt   8760
gcagtgagcc gagattgcgc cactgcactc cagcctgggc aacagagtga gaccctgtct   8820
cagaaaaaaa aagaaagaaa gaaaaaatag aggaatattt cccaacttgt tttcgaagcc   8880
agcataatcc tggtaccaaa accaaacaag gacattataa gaaaagaaaa tatagaccaa   8940
tattcctgtt agcatagaca tgcaacagct aaccaatttt agcaaaccaa acctggtaat   9000
atagaaaaaa ggataaatag gccagtcgcg gtggctcacg cctgtaatcc cagcactttg   9060
ggaggctgag gcaggcagat cacttgaggt caggagtttg agaccagcct gaccaacatg   9120
gtgaaacccc gtttctaata aaaatacaaa aatcaggctg ggcacggtgg ctcacgcctg   9180
taatcccagc actttgggag gccgaggtgg gcagatcacg aggtcaggag ttcaagacca   9240
gcctgaccaa tgtggtgaaa cgccatctct actaaaaata caaaaatcag ccggtgtggt   9300
ggcacctgcc tgtaatccca gctactcagg aggctgaggc agaattgctt gaacccggga   9360
ggcagaggtt gcagtgagcc aagatcgtgc cactgcactc cagcctgggc gacagagcaa   9420
gacttcatct caaaaaaaaa aaaaaattag ctgggcatgg tggtgggcac ctgaaatccc   9480
agctactcgg gagtctgagg caggagaatc gcttgaaccc aggaggcaga agttgcactg   9540
agctgggatc acaccattgc actccagcct gggcaacaga gtgagactcc atctcaaaaa   9600
```

```
aagaaaaaga aaaaggataa atacattcta accaaataat gtttatctca tgattgtagc   9660
tgattcaaca ttcaaaaatt ggcctggtgc agtagctcag gcctgtaatc ccaacatttt   9720
aggaggctga ggcaggaaga tctcttgagc ccaggatttc aagaccagcc tgggcaacat   9780
agtcagactg gtctttactg gggggaaaaa aatcagtctg tgtaattcac cacattaaca   9840
aagggaaaca taaaaaccct atgatcattt caacagatgt agcaaaagca gttaatgata   9900
ttcaacacat atgcatgatt acaaaccaac caacctccta gcaaactagg gaaaggaaac   9960
ttaacctagt ttgataacag ggcgtccaca gtcggagttc cactagcagc atacataatg  10020
gtagaaaact cagtgctgcc gggcgcggtg gctcacgcct gtaatgccag cactttggga  10080
ggcctaggcg ggcggatcac gaggtcagga gatcgagact gtcctgacta gcatgctgaa  10140
accccgtctc tactaaaaat acaaaaacaa aaaattagcc gggcatggtg gcgggcgcct  10200
atagtcccag ctactcggga ggctgaggcg agagaatggc gtgaacccgg gaggcggagc  10260
ttgcagagcc tagatcgtgc cactgcactc cagcctgggt gacagagtga gacttcgtct  10320
caaaaaaaaa aaaaaaaaaa aaagaaaaga aaactcaacg ctttttcctc taagatcagg  10380
aactagaaaa ggatttgact ctcacaacgt tgataccata ctggaggttt taaccaggca  10440
agaaaaagaa ataatgaggg ccgggtgcgg tggctcaggc ctgtaatccc agcactttgg  10500
gaagccgaga cgggtggatc acgaggtcag gagatcgaga ccatcctggc taacacggtg  10560
aaaccctgtc tctactaaat atacaaaaaa ttagccgggc gtagtggcgg gcgcctgtag  10620
tcccagctac tcgggaggct gaggcaggag aatggcgtga actcaggggg cggagcttgc  10680
agtgagctga gatcgagcca ctgcactcca gcctgggcga cagagcaaga ctgtgtctca  10740
aaaaaaaaaa aagaaaaaga aataatgatt agtggcccga tgtctcacgc ctataatccc  10800
agcactttgg gaggccgagg tggcagatc acctgaggtc tggagttgga gaccagcctg  10860
acaaagatgg tgaaacctcg tctctattaa aatattaaaa aaatagccag gcgttggccg  10920
ggtacagtgg ctcatgcctg taatcccagc actttgggag gccgaggtgg gtggatcacc  10980
tgaggtcagg agttcaacac cagcctggcc aacatggtga aaccccatct ctactaaaaa  11040
tacaaaaatt agccgggcgt agtggcgggc gcctgtaatc ccagctactt gggaggctta  11100
ggcaggagaa tcgcttgaac ctgggaggcg gaggttgtag tgagccgaga ttgcaccatt  11160
gcactccagc ctgggtgaca aaagcaaaaa ctccgtctca aaaaaaaaag aattagccag  11220
gggtagtggt gaacgcctgt agtcccagct actcaggagg cagaggcagg agaatcactt  11280
gaacccagga ggcagaggtt gcagtgagcc gagattgtcc cattgcactc cagcctaggc  11340
gacaagagca aaattccatg tcaaaaaaaa aaaaaaaaaa ggaaagaaaa aaaataacga  11400
ttagaaagga agaaataaaa cacattcaca gccagtatga ttctatacat acatgtccta  11460
atggggccag gcgtggtggc tcatgcctgt aatcctagca cttttaggag gctgaggcag  11520
gtggcttccc tgggaccagc ctggccaaca tggtgaaacc ccaactctaa taaaaataca  11580
aaaaatcagc caggcgtggt gacgggcacc tctaatccca gctactcagg aggctgaggc  11640
aggagaattg cttggacctg ggaggcagag gttgcagtga gccgagatcg cgctattgca  11700
ctccagcctg ggcaacaaga gtgaaactcc ggcagggtgt ggtggcttac gcctgtaatc  11760
ccagcacttc gggaggctga ggcaggccga tcacctgagg tcaggagttt gagaccaacc  11820
taacatggtg aaaccccgtc tctactaaaa atacaagaat tagctgggtg tagtggtggg  11880
cgcctgtaat cccagctact tgggaggctg agacagaaga attgcttgaa cccaggaggt  11940
```

```
ggaggttgca gtgagctgag atcatgccat tgcacaccac gccgggcaac agagcgagat  12000
tccgtctcaa aaaaaaaaaa aaagagtgaa actctatctc aaaaaaaaaa aaaagtccta  12060
atggaaaatc cataaaaagc taccaaaact aataaataaa tatagcaggg ttgcaggtta  12120
cagggcaata tagttatccc tctatctgta ggggcttggt tctgggactc ctcacacacc  12180
aaacccacag atgtctaagt cccatatata agacggtata gtatttggat ttaacctaca  12240
catatcctcc catatagttt aaattatctc tagattactt acattacccc catacaatga  12300
aaatgctaat gtacatgcaa gtatgtatgt aagtacttgt actatattgt ttagggaatc  12360
actggacata taggccttca agactgatac cagcagccac tgttaagatt ctggtcaggc  12420
ctgcccctgt ttggggtctc agttgatctc attgccttcc cacccagcca agggcacctg  12480
catttctctt ggctccctgg ccatttggaa ggcctagttc agcctggcac atttgtatcc  12540
tggcccactg atgctggtac ccctgggaag gtcctgctct gaaaaacacg gagattttag  12600
ttgctactga agatttgaga gataaagaca gggagacctg tctgtagacc tgtgtccctc  12660
caagtgggat tgagactttg ggccccccat ttcaggacag cacctcctgg cctgttgact  12720
gaatagatcc ctgaaggagg tgtacttgca ttaatggagt gggggtggga gcagtaccac  12780
agatccgcac taacaatcac acagttctct ctagaataat aatatagaac aagtgaaata  12840
gaacaattgc agaaagagct aacctttgtt gagctcttac tgtgtgccca gcactttcct  12900
caactctaca tttcccataa tacacagagt actaggtagg ccaggcttgg tggctcacgc  12960
ctgtaatccc agcactttag gaggccaagg ggggtggatc acctgaggtc gggagttcaa  13020
gaccagcctg accaacatgg tgaaaccccg tctctactag aagtacaaaa ttagccaggt  13080
gtggtggcac atgcttgtag tcctagctac tcagcaggct gaggcaggag aatcatttga  13140
atccgggagg aggttgcagt aagcggagat agtgccactg tactccagcc tgggcaataa  13200
gagctgagac tccgtctcaa aataaaataa aataaaataa aataaaataa aataaaataa  13260
aaaaagaaaa gagcctgcca ttaaaggagc tgtttggtag gggatgtttt gtcagtgcaa  13320
acaacagaaa agtgggctgg gcacagtggt tcatgcctgt aatcccagca ctttgggagg  13380
ccaaggcggg cggatcacct gaagttggga gttcaagacc agcctgacca atatggagaa  13440
accccgtctc tactaaaaat acaaaattag ccgggcgcag tggcgcatgc ctgtaatccc  13500
agctactcgg gaggctgagg caggagaatc gcttgaacct gggaggcaga ggttgcggtg  13560
agccgagatc gcaccattgc actccagcct ggacgagagc aaaactctgt ctcaaaaaaa  13620
aaaaaaaaca gaaaagtgta acaaacactt acagtaggca tgtttcttag caaatctgat  13680
gacaaatttg gcataaagaa agagagcatc cctgaaaaaa aaaaaaagaa aaagaaagag  13740
agcatcctgc ctgggcaaca tagtgaaacc ctgcctctac aaaaaaactc aaaaattggc  13800
cgggtgcagt ggctcacacc tgtaatccca gcactttggg agtcggaggc gggaggatca  13860
cctgaggtca ggagttcgaa accagcctgg ccaacatggc aaaaccccat ctctactaaa  13920
aatacaaaaa attaatcagg cgcattggtg ggcgcctgta atcccagcta ctcaggaagt  13980
tgaggcaaga ggatcgcttg aatctgggag gtggaggtta cagtgagtcg agatcacacc  14040
actgcactct agcctgggtg acagggcgag actccgtctc caaaaaaaaa aagaaaaaga  14100
aaaagactaa aaaattagcc aggcaggcct ctgtggtccc agctacttgg gaggctgagg  14160
caggagaatc actgagccca ggagtccgag gctgtagtga gccatgattg caccactgta  14220
ccctagcttg ggcaacaaag caagaccctg cctcaaaaga aaaaagaaag aaagaaagaa  14280
catggcgggc caggcacagt ggctcacacc tgtaatccca gcgctttgag aggccgaggc  14340
```

```
aggtggatca caaggtcagg agttccacac cagcctggcc aacatggtga aaccctgtct  14400
ctactaaaaa tacaaaaaat cagccaggca tggtggcagg ggcctgtaat cccagctact  14460
cgggaggctg aggcaggaga attgcttgaa accagaaggc agaggttgca gtgagcctag  14520
actgcaccac tgcactccag cctgggcgaa aagagccaaa ctccatctca aaaaacaaac  14580
aaaaaaacaa aacaaaagaa aacatggcaa agcctttgaa agcttgtctg ggagaaggtg  14640
cgatgatagt tgcataactt cgtgcaagat gctggtccac acaggggctg ccccttgctc  14700
tttctcgctc tcttaacctc tcatataaca ggcttgtgtg ttattcacat ttattgagcc  14760
caagcaggtg caaggcattg tgatctaata ctttggtcag caagacaaca agatagatca  14820
ctgccctgcc cttaggaagt gtatatgcta ttagaggaaa cagataaaat aaacaaggaa  14880
aagtatcaga caatgtaagt gctatgagaa tgcaaatgag gtgatgtgaa ttaaaatagg  14940
atgacttaaa gtctgcacgg gaaggagcct acccccatgt tcctggctag ccaaggaacc  15000
accagttgat tagcagagaa gggcagccag tctagctaga gcttttgggg aagagggagt  15060
ggttgttaag agatgagatt aaagaagccg agacgggcca ttcgtgaggg gtttgtaatg  15120
cagggctgag gagtgtccga agagaatggg caggtgagcg gtgagacagt tgttcttcca  15180
gaagctttgc agtgaaagga atcaaagaaa tggagccgtg tatcaggtgg ggaagggtgg  15240
gggccaaggg ggtgtccttc cccatacaga gattgcaggc tgagaatgac tatatccttg  15300
ttaacaggag gtgggagcag ggcacggtag ctcacacctg taatcttggc actttaggag  15360
gctgaggcgg gccgatcacc tgaagtaagg agttcgagac cagcctggcc aacatgcaaa  15420
gccctgtctc tactaaaaat acaaaaatta gctgggtgtg gtggtactcg cctgtaatcc  15480
cagctactcg ggagactgag gcaggagaat ggcttgaacc cggaaggtag aggttgcagt  15540
gagctgagat catgccactg tgctccagcc taggtgacag agagagactc catctcaaaa  15600
aaaaaaaaaa aatacaggaa gggagttggg aatagggtgc acatttagga agtcttgggg  15660
atttagtggt gggaaggttg gaagtccctc tctgattgtc ttttcctcaa agaagtgcat  15720
ggctggtgag ggtggggca ggagtgcttg ggttgtggtg aaacattgga agagagaatg  15780
tgaagcagcc attcttttcc tgctccacag gaagccgagc tgtctcagac actggcatgg  15840
tgttggggga gggggttcct tctctgcagg cccaggtgac ccagggttgg aagtgtctca  15900
tgctggatcc ccacttttcc tcttgcagca gccagactgc cttccgggtc actgccatgg  15960
aggagccgca gtcagatcct agcgtcgagc cccctctgag tcaggaaaca ttttcagacc  16020
tatggaaact gtgagtggat ccattggaag ggcaggccca ccacccccac cccaacccca  16080
gccccctagc agagacctgt gggaagcgaa aattccatgg gactgacttt ctgctcttgt  16140
ctttcagact tcctgaaaac aacgttctgg taaggacaag ggttgggctg gggacctgga  16200
gggctgggga cctggagggc tggggggctg gggggctgag gacctggtcc tctgactgct  16260
cttttcaccc atctacagtc ccccttgccg tcccaagcaa tggatgattt gatgctgtcc  16320
ccggacgata ttgaacaatg gttcactgaa gacccaggtc cagatgaagc tcccagaatg  16380
ccagaggctg ctccccccgt ggcccctgca ccagcagctc ctacaccggc ggcccctgca  16440
ccagccccct cctggcccct gtcatcttct gtcccttccc agaaaaccta ccagggcagc  16500
tacggtttcc gtctgggctt cttgcattct gggacagcca agtctgtgac ttgcacggtc  16560
agttgccctg aggggctggc ttccatgaga cttcaatgcc tggccgtatc cccctgcatt  16620
tcttttgttt ggaactttgg gattcctctt caccctttgg cttcctgtca gtgttttttt  16680
```

```
atagtttacc cacttaatgt gtgatctctg actcctgtcc caaagttgaa tattcccccc  16740
ttgaatttgg gcttttatcc atcccatcac accctcagca tctctcctgg ggatgcagaa  16800
cttttctttt tcttcatcca cgtgtattcc ttggcttttg aaaataagct cctgaccagg  16860
cttggtggct cacacctgca atcccagcac tctcaaagag gccaaggcag gcagatcacc  16920
tgagcccagg agttcaagac cagcctgggt aacatgatga aacctcgtct ctacaaaaaa  16980
atacaaaaaa ttagccaggc atggtggtgc acacctatag tcccagccac ttaggaggct  17040
gaggtgggaa gatcacttga ggccaggaga tggaggctgc agtgagctgt gatcacacca  17100
ctgtgctcca gcctgagtga cagagcaaga ccctatctca aaaaaaaaaa aaaaaaagaa  17160
aagctcctga ggtgtagacg ccaactctct ctagctcgct agtgggttgc aggaggtgct  17220
tacgcatgtt tgtttctttg ctgccgtctt ccagttgctt tatctgttca cttgtgccct  17280
gactttcaac tctgtctcct tcctcttcct acagtactcc cctgccctca acaagatgtt  17340
ttgccaactg gccaagacct gccctgtgca gctgtgggtt gattccacac ccccgcccgg  17400
cacccgcgtc cgcgccatgg ccatctacaa gcagtcacag cacatgacgg aggttgtgag  17460
gcgctgcccc caccatgagc gctgctcaga tagcgatggt gagcagctgg ggctggagag  17520
acgacagggc tggttgccca gggtccccag gcctctgatt cctcactgat tgctcttagg  17580
tctggcccct cctcagcatc ttatccgagt ggaaggaaat ttgcgtgtgg agtatttgga  17640
tgacagaaac acttttcgac atagtgtggt ggtgccctat gagccgcctg aggtctggtt  17700
tgcaactggg gtctctggga ggaggggtta agggtggttg tcagtggccc tccaggtgag  17760
cagtaggggg gctttctcct gctgcttatt tgacctccct ataaccccat gagatgtgca  17820
aagtaaatgg gtttaactat tgcacagttg aaaaaactga agcttacaga ggctaagggc  17880
ctcccctgct tggctgggcg cagtggctca tgcctgtaat cccagcactt tgggaggcca  17940
aggcaggcgg atcacgaggt tgggagatcg agaccatcct ggctaacggt gaaaccccgt  18000
ctctactgaa aaatacaaaa aaaaattagc cgggcgtggt gctgggcacc tgtagtccca  18060
gctactcggg aggctgagga aggagaatgg cgtgaacctg ggcggtggag cttgcagtga  18120
gctgagatca cgccactgca ctccagcctg ggcgacagag cgagattcca tctcaaaaaa  18180
aaaaaaaaaa ggcctcccct gcttgccaca ggtctcccca aggcgcactg gcctcatctt  18240
gggcctgtgt tatctcctag gttggctctg actgtaccac catccactac aactacatgt  18300
gtaacagttc ctgcatgggc ggcatgaacc ggaggcccat cctcaccatc atcacactgg  18360
aagactccag gtcaggagcc acttgccacc ctgcacactg gcctgctgtg ccccagcctc  18420
tgcttgcctc tgacccctgg gcccacctct taccgatttc ttccatacta ctacccatcc  18480
acctctcatc acatccccgg cggggaatct ccttactgct cccactcagt tttcttttct  18540
ctggctttgg gacctcttaa cctgtggctt ctcctccacc tacctggagc tggagcttag  18600
gctccagaaa ggacaagggt ggttgggagt agatggagcc tggtttttta aatgggacag  18660
gtaggacctg atttccttac tgcctcttgc ttctcttttc ctatcctgag tagtggtaat  18720
ctactgggac ggaacagctt tgaggtgcgt gtttgtgcct gtcctgggag agaccggcgc  18780
acagaggaag agaatctccg caagaaaggg gagcctcacc acgagctgcc cccagggagc  18840
actaagcgag gtaagcaagc aggacaagaa gcggtggagg agaccaaggg tgcagttatg  18900
cctcagattc acttttatca cctttccttg cctctttcct agcactgccc aacaacacca  18960
gctcctctcc ccagccaaag aagaaaccac tggatggaga atatttcacc cttcaggtac  19020
taagtcttgg gacctcttat caagtggaaa gtttccagtc taacactcaa aatgccgttt  19080
```

```
tcttcttgac tgttttacct gcaattgggg catttgccat cagggggcag tgatgcctca  19140
aagacaatgg ctcctggttg tagctaacta acttcagaac accaacttat accataatat  19200
atattttaaa ggaccagacc agctttcaaa aagaaaattg ttaaagagag catgaaaatg  19260
gttctatgac tttgcctgat acagatgcta cttgacttac gatggtgtta cttcctgata  19320
aactcgtcgt aagttgaaaa tattgtaagt tgaaaatgga tttaatacac ctaatctaag  19380
gaacatcata gcttagccta gcctgctttt tttttttttt tttttggaga cagagtctca  19440
ctctgtcacc caggctggag tgcagtggcg ggatctcggc tcactgcaac ctccgccttc  19500
tgggttcaag cgattctcct gcctcagccc actgagtagc tgggattaca ggcacctgcc  19560
ccgacgccca gctaattttt tgttatttat ttattttttt ttttagtaga gatgaggttt  19620
caccatgttg gccaggctag tctcgaactc ctgaccttgt gatctgcctg ccttggcctc  19680
ccaaagtgct gggattacag gcgtgagcca ccgcacccgg cctgcctagc ctacttttat  19740
tttattttta atggagacag catcttgctc tgttgcccag gctggattac agtgatgtga  19800
tcatagctca ttataccctc ctgggctcaa gcaatccccc taactctgcc tccccagtag  19860
ctaggaccac aggcatacac caccataccc agctaatttt taaaattttt tgtagataga  19920
tagagtctca ctatgttgcc caggctggtc tctagcctac ttttttgaga caaggtcttg  19980
ctctgtcacc caggctggat agagtgcagt agtgcagtca cagctcactg cagcctccac  20040
ctcccaggct ccatccatcc tcccagctca gcctcccaag ttgcttcaac tacaggcctg  20100
caccaccatg cctggctaat ttttatttat ttatttttat tttattttat tttatttttt  20160
tgagactcag tctcactctg tcgcccaggc tggagtgcag tggcatgatc tcggctcact  20220
gcaacctctg cctcctgggt tcaagtgatt ctcctgcctc agcctcccga atagctagga  20280
ctacaagcgc ctgctaccac gcccagctaa tttttgtatt tttagtagag acagggtttc  20340
accatgttgg ccaggctggt ctcgaacttc tgaccatgtg atccgcccgc ctcggcctcc  20400
caaagtgctg ggattacagg tgtgagccac cacgcccggc taatttttat ttatttattt  20460
aaagacagag tctcactctg tcactcaggc tagagtgcag tggcaccatc tcagctcact  20520
gcagccttga cctccctggg ctccggtgat ttcaccctcc caagtagcta ggactacagg  20580
cacatgccac gacacccagc taattttta ttttctgtga agtcaaggtc ttgctacgtt  20640
gcccatgctg gtatcaaacc cctgggctca atcaatcctt ccacctcagc ctccccaagt  20700
attggggtta caggcatgag ctaccacact cagccctagc ctacttgaaa cgtgttcaga  20760
gcatttaagt taccctacag ttgggcaaag tcatctaaca caaagccctt tttatagtaa  20820
taaaatgttg tatatctcat gtgatttatt gaatattgtt actgaaagtg agaaacagca  20880
tggttgcatg aaaggaggca cagtcgagcc aggcacagcc tgggcgcaga gcgagactca  20940
aaaaaagaaa aggccaggcg cactggctca cgcctgtaat cccagcattt cgggaggctg  21000
aggcgggtgg atcacctgag gtcaggagtt caagaccagc ctagccaaca tggtgaaacc  21060
ccgtctctac taaaatacaa aaattaaccg ggcgtgatgg caggtgcctg taatcccagc  21120
tacttgggag gctgaggcag gagaatcgct tgaaccagga ggcggaggtt gcagggagcc  21180
aagatggcgc cactgcactc cagcctgggc gatagagtga gactccgtct cagaaaaaaa  21240
agaaaagaaa cgaggcacag tcgcatgcac atgtagtccc agttacttga gaggctaagg  21300
caggaggatc tcttgagccc aagagtttga gtccagcctg aacaacatag caagacatca  21360
tctctaaaat ttaaaaaagg gccgggcaca gtggctcaca cctgtaatcc cagcactttg  21420
```

```
ggaggtggag gtgggtagat cacctgacgt caggagttgg aaaccagcct ggctaacatg  21480
gtgaagcccc atctctacta aaaacacaaa aattagccag gtgtggtagc acacgcctgt  21540
agtcccagct actcgggagg ctgaggcaca agaatcactt gaaccccaga ggcggagatt  21600
gcaatcagcc aagattgcac cattgcactc ccgcctgggc aacagagtga gaccccatct  21660
caaaataaat aaataaatat ttttaaaagt cagctgtata ggtacttgaa gtgcagtttc  21720
tactaaatgc atgttgcttt tgtaccgtca taaagtcaaa caattgtaac ttgaaccatc  21780
ttttaactca ggtactgtgt atatacttac ttctcccct cctctgttgc tgcagatccg  21840
tgggcgtgag cgcttcgaga tgttccgaga gctgaatgag gccttggaac tcaaggatgc  21900
ccaggctggg aaggagccag gggggagcag ggctcactcc aggtgagtga cctcagcccc  21960
ttcctggccc tactcccctg ccttcctagg ttggaaagcc ataggattcc attctcatcc  22020
tgccttcatg gtcaaaggca gctgacccca tctcattggg tcccagccct gcacagacat  22080
tttttagtc ttcctccggt tgaatcctat aaccacattc ttgcctcagt gtatccacag  22140
aacatccaaa cccagggacg agtgtggata cttctttgcc attctccgca actcccagcc  22200
cagagctgga gggtctcaag gaggggccta ataattgtgt aatactgaat acagccagag  22260
tttcaggtca tatactcagc cctgccatgc accggcaggt cctaggtgac ccccgtcaaa  22320
ctcagtttcc ttatatataa aatggggtaa gggggccggg cgcagtggct cacgaatccc  22380
acactctggg aggccaaggc gagtggatca cctgaggtcg ggagtttgag cccagcctga  22440
ccaacatgga gaaaccccat ctctactaaa aatacaaaag tagccgggcg tggtgatgca  22500
tgcctgtaat cccagctacc tactcgggag gctgaggcag gagaatcgct tgaacccggg  22560
aggcagaggt tgcggtgagc tgagatctca ccattacact ccagcctggg caacaagagt  22620
gaaactccgt ctcaaaaaag ataaataaag taaaatgggg taagggaaga ttacgagact  22680
aatacacact aatactctga ggtgctcagt aaacatattt gcatggggtg tggccaccat  22740
cttgatttga attcccgttg tcccagcctt aggcccttca aagcattggt cagggaaaag  22800
gggcacagac cctctcactc atgtgatgtc atctctcctc cctgcttctg tctcctacag  22860
ccacctgaag tccaaaaagg gtcagtctac ctcccgccat aaaaaactca tgttcaagac  22920
agaagggcct gactcagact gacattctcc acttcttgtt ccccactgac agcctcccac  22980
ccccatctct ccctcccctg ccattttggg ttttgggtct ttgaaccctt gcttgcaata  23040
ggtgtgcgtc agaagcaccc aggacttcca tttgctttgt cccggggctc cactgaacaa  23100
gttggcctgc actggtgttt tgttgtgggg aggaggatgg ggagtaggac ataccagctt  23160
agattttaag gtttttactg tgagggatgt ttgggagatg taagaaatgt tcttgcagtt  23220
aagggttagt ttacaatcag ccacattcta ggtaggggcc cacttcaccg tactaaccag  23280
ggaagctgtc cctcactgtt gaattttctc taacttcaag gcccatatct gtgaaatgct  23340
ggcatttgca cctacctcac agagtgcatt gtgagggtta atgaaataat gtacatctgg  23400
ccttgaaacc accttttatt acatggggtc tagaacttga cccccttgag ggtgcttgtt  23460
ccctctccct gttggtcggt gggttggtag tttctacagt tgggcagctg gttaggtaga  23520
gggagttgtc aagtctctgc tggcccagcc aaaccctgtc tgacaacctc ttggtgaacc  23580
ttagtaccta aaaggaaatc tcaccccatc ccacaccctg gaggatttca tctcttgtat  23640
atgatgatct ggatccacca agacttgttt tatgctcagg gtcaatttct tttttctttt  23700
ttttttttt ttttcttttt ctttgagact gggtctcgct ttgttgccca ggctggagtg  23760
gagtggcgtg atcttggctt actgcagcct ttgcctcccc ggctcgagca gtcctgcctc  23820
```

agcctccgga gtagctggga ccacaggttc atgccaccat ggccagccaa cttttgcatg 23880
ttttgtagag atggggtctc acagtgttgc ccaggctggt ctcaaactcc tgggctcagg 23940
cgatccacct gtctcagcct cccagagtgc tgggattaca attgtgagcc accacgtcca 24000
gctggaaggg tcaacatctt ttacattctg caagcacatc tgcattttca ccccaccctt 24060
cccctccttc tccctttta tatcccattt ttatatcgat ctcttatttt acaataaaac 24120
tttgctgcca cctgtgtgtc tgaggggtga acgccagtgc aggctactgg ggtcagcagg 24180
tgcaggggtg agtgaggagg tgctgggaag cagccacctg agtctgcaat gagtgtgggc 24240
tggggggccc agtgcccggg ttccgggagg ggaacaaagg ctggagactg ggtcagtctg 24300
cgggctgcat gacaacaagg gagggggtgg ctccattcat aactcaggaa ccaaccgtcc 24360
ctcctcccct ccggccacgg ctggcacaag gttctctccc tcccctgctt ctaggactgg 24420
gctgcttccc cctcggcagc ctctcaccaa ggattacggg atttaaatgt ctgatttagc 24480
aaggctgagc ctccagggtg gccatctgct ccatcagaaa gtggcaggat acctgggttc 24540
ccaaggggaa caggggtggg tgctactgga tggagagagg ccagtgggag gcctgctagc 24600
cagggtccca ggaaagtggg ggcagctaag gtaagagtag ggtgtgtggg ctaggtcctt 24660
cccagcatcc cctcatcctg ggcctcatgc caggtagctg aatgaattga agctttaaac 24720
tctgccagga aaacctttca aagggcttct tgggataggg aggagagtcg ggttgaggag 24780
ctcagtactg cctgcccatg ctcctcaggg ctgctggctc ccagggaggg gggctgggag 24840
caggcaggct cttccccatc acccactgct ctcttggagc cagtgcttga aggggcagtc 24900
agacatggct tgcccttcct cctccctggt ggtggagatg ggtgttaggg tccagtgggt 24960
gctactgtcc aggggggctt ctggggccac cagcctgtca gctcatcaac caggctgaag 25020
gtgcaagcag gagccccttg ccttgcccca aggatcccag acagctatga agccaccagc 25080
cttcctgacc tcaagaccac cttttttttt tctctttctt actagggaat gccaaacact 25140
ctccccagga gatccagacc cgcctctttc agagactttt aacttaaaca tctgtcccta 25200
cccagcaggc aaactagagc tcctgaagct cagtccctgt ccttgcctct gtagacaggt 25260
caccttgatg agcttccttt tttttttttt aatttttttt tattttaggc tttattgggg 25320
cataattgat cccccaaaat tgcatacatt caaggtatgc agtgtgatga tttgatatgg 25380
gggtatattg tgaaaccatt accacaatca aattaatcag cacgtccatc atcacacaca 25440
gttaccattt gtgtgtgtgc acgtgtgttc acctacgacg aggacacttg gacctactct 25500
gcagatctca agtaaacaga aaatctccct ttttgacaac catcctccac cctttcaatc 25560
ccaacctttt cctagattat gtccctagct ctgtttttat ttctgctgtg ctgcttcaga 25620
tccattctga ctctgccaaa cccttctttg tgagctgata gattgctgga ttgagaatta 25680
cagctgggcg cggtggctca cgcctgtaat cccaacactg tgggaggcca aggccggcgg 25740
atcacttgag gtcaggagtt ggagaccagc ctgaccaaca agatgaaacc ccatctctac 25800
taaaaataca aaattagctg ggcatggtgg tgcacgcctg taatctcatc ttcttgggag 25860
gctgaggcag gagaattgct tgaacccggg aggtggaggt tgcagtgagc caagatcctg 25920
ccattgcact ccagcctggg caacaacagt gaagctccat ctcaaaacac acaaaaaaaa 25980
gaagtacaaa gtctgagact tcaggccagc tctgctacac tatatactct aacctctctg 26040
gtcctacttg gtgacttctt tccctctggt cgtgttcaag ttcccgtccc atccagtcaa 26100
gcaggtactc attggtacct taccctgtgc caggagctgt tctaggccct ggaaacctat 26160

```
ggcagacatg ttccctaccc tcccactcaa agagcccagg ccttatccta atgagatctg  26220
aaatcaaatc tcccaatttc ctcatggctt cagtctaaac ttgtaattca caaccttaaa  26280
tcaatatgtt ctattttttt atttagaaaa catttccggc caggcacggt ggatcacacc  26340
tgtaatccca gctactcggg aggctgaggc aggagaatcg cttgaaccca ggaggcagag  26400
ggttgcagtg agccgagatt gcgccattgc actctagcct gggcaacaga gcaagactcc  26460
atctcaaaaa agaaaaaaaa atggaagaaa aaaaaatttc cccctcattt taggaacacg  26520
aggtctccaa atctaaaatt cgtactctga ggagattgaa tagccttaaa tgctttcatc  26580
attaaaaaga aaagaaagga acctggtatg catcctaaaa atgaaaaata tacctacctg  26640
taatcccagc acacagcaca ttgggaggct aaagcaggag gataacttga ggccaggagt  26700
ttcagatcag cctgggcaac atagcaacac cccatttctt tttcttttct tttttttttg  26760
gagacacagt ctcgctctgt tactcaggct ggagtgcagt ggctcaatct cagctcactg  26820
caagctctgc ctcccaggtt catgccattc tcctgcctca gcctcccgag tagctgggac  26880
tacaggcgcc cgccaccacg cctggctaat tttttgtatt tttagtagag acagggtttc  26940
accgtgttag ccaggatggt ctcgatctcc tgacctcgtg atccgccagc cttggcctcc  27000
taaagtactg ggattacagg cgtgagccac tgcgcctggc cacaacaccc catttctatt  27060
ttaataaaat aaaatactgt gaaaaacatt tacaattttt aaattttaat tttaaaatta  27120
aacttatatt tattcatttg tgtgtgtggg tttttttttt tttttttttt tgcttttttt  27180
ttgagatgga gtgtcactct gtcacccagg ctggagtgca gtggcgtgat ctctgcctcc  27240
cggttcaagt gattctcctg ccatagcctc ccaagtagct gggactacag gtacacgcca  27300
ccacgccggg ttaatttttg tatttttagt agagacagga tttcactgtg tcgccaggct  27360
agcctcgaac tcctgacctc aggtgattcg cccaccttgg cctcccaaag tgctgtgatt  27420
acaagcgtga gccaccgtgc ccagcccaaa gttggtttta atagcagaaa atctatcaac  27480
ataattcaat atattaaatt tagaaagaaa aattatctat catatcaaca gatactgaaa  27540
ggaatttgat taaatttcag tagccatttc cttaaaaaag aaaacacttt aacacagtaa  27600
tagactgata atggaatacc aattttccta ataagttaaa cattaagata atttcaatta  27660
aggtcaagag ctgggccagg tgcagtggct cacacctgta atcccaacac tttggaggcc  27720
aaggtgggtg gatcacctga ggtcaggagt ggagaccagc ctggctgaca atagtgaaat  27780
cctgcctcta ctaaaaacac aaaaaattag ctgggcatgg tggtgggcac ctataatccc  27840
agctactggg aaggctgaga caggagaatt gcttgaacct gggaggcgga ggttgcagtg  27900
agcaaagatc acaccattgc actccagcct gggcgacaga gccagagtca gtctcaaaaa  27960
aaaaaagagg tggccacacc tataatccaa acattttgtg aggccaaggc aggagaattg  28020
cttcaggcca agagttgaac acctcgtcaa catagccaga cctctctcta gatagataga  28080
tagatgatag atagagagat agatagatga tagatagaga gatagataga tgatagatag  28140
atagatagat agatagatag atagatagat agatagatag atagatagat aatctggccg  28200
ggtgtggagg ctcacgcctg taatcccagc actttgggag gctgaggcgg gcagatcacg  28260
aggacaagag attgaaacca tcctggctaa caaggtgaaa ccccgtctct actaaaaata  28320
caaaaaatta ggcgggtgtg gtggcacgcg cctgtagtcc tagctattca ggaggctgag  28380
acaggagaat tgcttgaatc cgaaaggcgg aggttgcagc gagccgagat cgtgccactg  28440
cactccagcc tgggtgacag agcaagactc catctcaaaa taaataaata aataatcaag  28500
aacagtataa ggggctgtat ggtggctcat gcctgtgatc ccagcacttt gggaggccaa  28560
```

```
ggtgggagga tcccttgaga ccagcccagg caacagagaa agaccctgtc tctatttaaa  28620
aaaattaaaa actggccggg cacggtggct cacgcctgta attccagcgc ttgggaggcc  28680
aaggcaggca catcaggagg tcaggagttc gagaccagcc tggccaacgt ggtgaaaccc  28740
cgtctctact aaaaatacaa aaagtagcta ggcgtggtgg caggcacctg taatcccagc  28800
tacttgggag gctgaggcag gagaatcgct tgaacccagg aggcggaggt tgcagtgggc  28860
aaagatcgtg ccattgcact cagcctgggt gacagggcaa gactccatct caaaataaat  28920
aaacaaagta attaattaat taaattaaaa actgtgggga tatagactta ctctggtttt  28980
attttttctt ttcttttctt ttcttttttc tgagacggag tctcgctctg ttgcccaggc  29040
tggagtacag tggcgtggtt tctgttctct gcaacctcca cctcccggat tcaagcgatt  29100
ctcttgcctc agcctcttga atacctggaa ttacaggtgc ctgccaccac ccccggctaa  29160
tttttgtat ttttagtaga gacagggttt caccatgttg gccaagctgg tctcgaactc  29220
ctgacctcat gatccacccg cctctgcctc ccaaagcact gagactacag gagtgagcca  29280
ctgtgcccag cctactctgg ttttagtgca ttcaagagga acaaaaaagg aagaaaatca  29340
ctagtaaata tacctctttc tggttagagt ggatgtttgg aaattatata tatattatat  29400
tatattatat atattatata tatacacaaa cacgtacata catgcacaca catatatgcc  29460
tttttgatta taggatagta taccaaaact cagaaatatt atggaattaa cagaatttag  29520
taaggcagat aagtagtagg tagaaaaata ttaattttat cttccagcag aagcactgtg  29580
aaaaattaga caacaagaaa acattccatt caaaataatg acaataaggc cgggcatggt  29640
ggctcacacc tgtaatccca gcactttggg aggctgaggc aggaggatca tctgaggtca  29700
agtttgagat cagcctggcc aacatggtga caccctgtct ctactgaaaa tacaaaaatc  29760
agccagctat ggtagtgtaa gcctgtaatt ccagctactc gggaggtcga agcagaagaa  29820
tcacttgaac ccaggaggca gagattgcag tgagccaaga tcctgccagt gctttccagc  29880
ctgggcaaca gtgtgaggct ccatctcaaa aaaaaaaaaa aaaaaaagac aatagcaata  29940
aacattaaga aatgtgtaat aggaatggca cacacaaaga aggaatggca cagagcctgt  30000
atgcagaaga ccacaaaccc ttatttaacg acgtaagcca agatccaaag aaaatgatag  30060
attctcagat gggaaaacta aaaaaataag aaaaatcaat tatctcgaga taaatataat  30120
ataatgcaat ttcaattaga atcccaaatt ttcattgtgt gtgtgtgtga gttgggtaaa  30180
tttatcataa atgtatagga acgagtaagt gtcactagtt gtttaaataa atactggatt  30240
tgggccaggc atggtggctc acgcctctaa tcccagcact ttgggagacc gaggcgggca  30300
gatcatgagg tcaggagatc gagaccatct ggccaacata gtgaaaactc gtctctacta  30360
aagatacaaa aaattagctg ggcatggtgg cacgtgcctg tagttccagc tactctggag  30420
gctgaggcag gagagttgct tgaacccggg aggtggaggt tgcaatgagc cgagatcctg  30480
tcactgcact ccaccctggc gacaaagtga gactccgtct ctctctctct ctttaggcca  30540
aggcaggtgg atcacctgag gtcaggagtt caagacagcc tggccaacat agcgaaatcc  30600
catctctact aaaaatacaa aaattagcct ggcagtggtg gcccacgcct gtaatcccag  30660
ctactaaggg ggctgaggca ggaggatctc ttaaccaggg aggaggaggt tgcagtgagc  30720
agagattgtg ccactgcact ccagcctgtg caacagagtg agactctgtc tcaaaaaaaa  30780
taaataaaca aaatactgga ggccgggcac ggtggctccc gcctgtaatc ccagcacttt  30840
gggaggccaa ggcgggtgaa tcgctttcag ctcaggagtt ccggaccagt ctgggcaaca  30900
```

```
tggcaaaacc ccgtctatac taaaaataca aaacttagcc aggcgtggta gtgcatacct  30960

ataatcccag ctactcgaga ggctgaggca ggagaatccc ttgaaaccgg gaggcagagg  31020

ttgcagtaag ctgaaatcgt gccactgcac tccagcctgg acgacacagc gggagactgt  31080

ctcaataaat aaaataaata atataaaata acataaataa taaaattgta aataataagt  31140

aaataataag caacagaatg gagagggggt cctatttgcc ttgccagatt ttagagaact  31200

tagtataggc taggcaggtg cagtggctca cgcctgtaat cccagcactt tgggagtcca  31260

aggcagtgga tcacatgagg tcaggagttc aagaccagcc tgaccaacat ggtgaaaccc  31320

catctctact aaaaatacaa aattagccag gcatggtggc acatgcctgt aatcccagct  31380

acttgggagg ctgaggcagg agaatcactt gaactcgaga ggtggaagct gcagcgagct  31440

gagatcacgc tactgtactc cagcctgggc aacaagagtg agactccatc aaaaaaaaaa  31500

aaaaagaaac gagaaaaaaa aaaagaaaac ttactatata actgctggaa tgaggtggat  31560

gtgacatatg gagtggtaga caaaccaagg aaagcaagta acaaatacag gagatgttct  31620

catacaggag aattattaca tggccaaaat tagcatttca atttaattgg aacacattag  31680

atatatttgt tcttttgttc tttttgttat cttttttttt tttttttttt tttttttttt  31740

gagacagagt ttcgctctca ttgcccaggc tggagtgtaa tggtgtgatc ttgactcacc  31800

gcaacctccg cttcctacgt tgaagtgatt ctcctgcctc agcctcccga gtagccggga  31860

ttacaggcat acgccaccac acctggctaa tttttttttgc attttcagta gagacagggt  31920

ttctccatgt tgatcaggct ggtttcgaac tcctgagctt aggtgatccg cccacctcag  31980

cctcccaaag tgctgggatt acaggcgtga gccactgtgc ccggccccta tctctttttt  32040

tgtttgtttg ttttctgaga tggaatctgg ctctctcacc caggctagag tgcaatggca  32100

cgatgttggc tcactgcaac atccacgtcc cgggttcaag cgattcttct gcctcagcct  32160

cccaagtagc tgggattaca ggtgcctgtc gccacatcca gctaattttt tgtattttta  32220

gtagagacag ggtttcaccg tgttccccag gctggtctca aactcctgag ctccggcaat  32280

ccacccgcct cggcttccca aagcgctagg attacaggcg tgagccaccg cacctggccc  32340

ctatctctta aaaatatatt tttttgccca acacacattt ccaagttgcc ttgggggaaa  32400

aaaaataaat gaagctggca caactgaaaa aataaaactg gggccttggc caggcacagt  32460

ggctcaggcc tataatccca gcactttggg aagctgaggt gggaggatca cttgaggtca  32520

ggagttcgag accagtctgg ctaacacggt gaaaaccctt ctctactaaa aatacaaaag  32580

tcagccaggc gtagtggtgt gcacctgtaa tcccagctac tcaggtagct gaggcatgag  32640

aatcacatga acctggaaag tggaggttgc agtgagccga gattgcacca ctgcactcca  32700

gcctgggtaa ggaaatgaga ctctgtctcc aaaaaaaaaa aaaagatact acaaagtcaa  32760

gagacaaaca at                                                      32772
```

```
<210> SEQ ID NO 4
<211> LENGTH: 479
<212> TYPE: PRT
<213> ORGANISM: Homo sapiens

<400> SEQUENCE: 4

Met Asp Phe Ser Arg Asn Leu Tyr Asp Ile Gly Glu Gln Leu Asp Ser
1               5                   10                  15

Glu Asp Leu Ala Ser Leu Lys Phe Leu Ser Leu Asp Tyr Ile Pro Gln
            20                  25                  30

Arg Lys Gln Glu Pro Ile Lys Asp Ala Leu Met Leu Phe Gln Arg Leu
```

```
        35                  40                  45

Gln Glu Lys Arg Met Leu Glu Glu Ser Asn Leu Ser Phe Leu Lys Glu
    50                  55                  60

Leu Leu Phe Arg Ile Asn Arg Leu Asp Leu Leu Ile Thr Tyr Leu Asn
65                  70                  75                  80

Thr Arg Lys Glu Glu Met Glu Arg Glu Leu Gln Thr Pro Gly Arg Ala
                85                  90                  95

Gln Ile Ser Ala Tyr Arg Val Met Leu Tyr Gln Ile Ser Glu Glu Val
            100                 105                 110

Ser Arg Ser Glu Leu Arg Ser Phe Lys Phe Leu Leu Gln Glu Glu Ile
        115                 120                 125

Ser Lys Cys Lys Leu Asp Asp Asp Met Asn Leu Leu Asp Ile Phe Ile
    130                 135                 140

Glu Met Glu Lys Arg Val Ile Leu Gly Glu Gly Lys Leu Asp Ile Leu
145                 150                 155                 160

Lys Arg Val Cys Ala Gln Ile Asn Lys Ser Leu Leu Lys Ile Ile Asn
                165                 170                 175

Asp Tyr Glu Glu Phe Ser Lys Glu Arg Ser Ser Ser Leu Glu Gly Ser
            180                 185                 190

Pro Asp Glu Phe Ser Asn Gly Glu Glu Leu Cys Gly Val Met Thr Ile
        195                 200                 205

Ser Asp Ser Pro Arg Glu Gln Asp Ser Glu Ser Gln Thr Leu Asp Lys
    210                 215                 220

Val Tyr Gln Met Lys Ser Lys Pro Arg Gly Tyr Cys Leu Ile Ile Asn
225                 230                 235                 240

Asn His Asn Phe Ala Lys Ala Arg Glu Lys Val Pro Lys Leu His Ser
                245                 250                 255

Ile Arg Asp Arg Asn Gly Thr His Leu Asp Ala Gly Ala Leu Thr Thr
            260                 265                 270

Thr Phe Glu Glu Leu His Phe Glu Ile Lys Pro His Asp Asp Cys Thr
        275                 280                 285

Val Glu Gln Ile Tyr Glu Ile Leu Lys Ile Tyr Gln Leu Met Asp His
    290                 295                 300

Ser Asn Met Asp Cys Phe Ile Cys Cys Ile Leu Ser His Gly Asp Lys
305                 310                 315                 320

Gly Ile Ile Tyr Gly Thr Asp Gly Gln Glu Ala Pro Ile Tyr Glu Leu
                325                 330                 335

Thr Ser Gln Phe Thr Gly Leu Lys Cys Pro Ser Leu Ala Gly Lys Pro
            340                 345                 350

Lys Val Phe Phe Ile Gln Ala Cys Gln Gly Asp Asn Tyr Gln Lys Gly
        355                 360                 365

Ile Pro Val Glu Thr Asp Ser Glu Glu Gln Pro Tyr Leu Glu Met Asp
    370                 375                 380

Leu Ser Ser Pro Gln Thr Arg Tyr Ile Pro Asp Glu Ala Asp Phe Leu
385                 390                 395                 400

Leu Gly Met Ala Thr Val Asn Asn Cys Val Ser Tyr Arg Asn Pro Ala
                405                 410                 415

Glu Gly Thr Trp Tyr Ile Gln Ser Leu Cys Gln Ser Leu Arg Glu Arg
            420                 425                 430

Cys Pro Arg Gly Asp Asp Ile Leu Thr Ile Leu Thr Glu Val Asn Tyr
        435                 440                 445

Glu Val Ser Asn Lys Asp Asp Lys Lys Asn Met Gly Lys Gln Met Pro
    450                 455                 460
```

```
Gln Pro Thr Phe Thr Leu Arg Lys Lys Leu Val Phe Pro Ser Asp
465                 470                 475
```

```
<210> SEQ ID NO 5
<211> LENGTH: 416
<212> TYPE: PRT
<213> ORGANISM: Homo sapiens

<400> SEQUENCE: 5

Met Asp Glu Ala Asp Arg Arg Leu Leu Arg Arg Cys Arg Leu Arg Leu
1               5                   10                  15

Val Glu Glu Leu Gln Val Asp Gln Leu Trp Asp Ala Leu Leu Ser Arg
            20                  25                  30

Glu Leu Phe Arg Pro His Met Ile Glu Asp Ile Gln Arg Ala Gly Ser
        35                  40                  45

Gly Ser Arg Arg Asp Gln Ala Arg Gln Leu Ile Ile Asp Leu Glu Thr
    50                  55                  60

Arg Gly Ser Gln Ala Leu Pro Leu Phe Ile Ser Cys Leu Glu Asp Thr
65                  70                  75                  80

Gly Gln Asp Met Leu Ala Ser Phe Leu Arg Thr Asn Arg Gln Ala Ala
                85                  90                  95

Lys Leu Ser Lys Pro Thr Leu Glu Asn Leu Thr Pro Val Val Leu Arg
            100                 105                 110

Pro Glu Ile Arg Lys Pro Glu Val Leu Arg Pro Glu Thr Pro Arg Pro
        115                 120                 125

Val Asp Ile Gly Ser Gly Gly Phe Gly Asp Val Gly Ala Leu Glu Ser
    130                 135                 140

Leu Arg Gly Asn Ala Asp Leu Ala Tyr Ile Leu Ser Met Glu Pro Cys
145                 150                 155                 160

Gly His Cys Leu Ile Ile Asn Asn Val Asn Phe Cys Arg Glu Ser Gly
                165                 170                 175

Leu Arg Thr Arg Thr Gly Ser Asn Ile Asp Cys Glu Lys Leu Arg Arg
            180                 185                 190

Arg Phe Ser Ser Leu His Phe Met Val Glu Val Lys Gly Asp Leu Thr
        195                 200                 205

Ala Lys Lys Met Val Leu Ala Leu Leu Glu Leu Ala Gln Gln Asp His
    210                 215                 220

Gly Ala Leu Asp Cys Cys Val Val Val Ile Leu Ser His Gly Cys Gln
225                 230                 235                 240

Ala Ser His Leu Gln Phe Pro Gly Ala Val Tyr Gly Thr Asp Gly Cys
                245                 250                 255

Pro Val Ser Val Glu Lys Ile Val Asn Ile Phe Asn Gly Thr Ser Cys
            260                 265                 270

Pro Ser Leu Gly Gly Lys Pro Lys Leu Phe Phe Ile Gln Ala Cys Gly
        275                 280                 285

Gly Glu Gln Lys Asp His Gly Phe Glu Val Ala Ser Thr Ser Pro Glu
    290                 295                 300

Asp Glu Ser Pro Gly Ser Asn Pro Glu Pro Asp Ala Thr Pro Phe Gln
305                 310                 315                 320

Glu Gly Leu Arg Thr Phe Asp Gln Leu Asp Ala Ile Ser Ser Leu Pro
                325                 330                 335

Thr Pro Ser Asp Ile Phe Val Ser Tyr Ser Thr Phe Pro Gly Phe Val
            340                 345                 350

Ser Trp Arg Asp Pro Lys Ser Gly Ser Trp Tyr Val Glu Thr Leu Asp
```

```
        355                 360                 365

Asp Ile Phe Glu Gln Trp Ala His Ser Glu Asp Leu Gln Ser Leu Leu
    370                 375                 380

Leu Arg Val Ala Asn Ala Val Ser Val Lys Gly Ile Tyr Lys Gln Met
385                 390                 395                 400

Pro Gly Cys Phe Asn Phe Leu Arg Lys Lys Leu Phe Phe Lys Thr Ser
                405                 410                 415


<210> SEQ ID NO 6
<211> LENGTH: 393
<212> TYPE: PRT
<213> ORGANISM: Homo sapiens

<400> SEQUENCE: 6

Met Glu Glu Pro Gln Ser Asp Pro Ser Val Glu Pro Pro Leu Ser Gln
1               5                   10                  15

Glu Thr Phe Ser Asp Leu Trp Lys Leu Leu Pro Glu Asn Asn Val Leu
            20                  25                  30

Ser Pro Leu Pro Ser Gln Ala Met Asp Asp Leu Met Leu Ser Pro Asp
        35                  40                  45

Asp Ile Glu Gln Trp Phe Thr Glu Asp Pro Gly Pro Asp Glu Ala Pro
    50                  55                  60

Arg Met Pro Glu Ala Ala Pro Pro Val Ala Pro Ala Pro Ala Ala Pro
65                  70                  75                  80

Thr Pro Ala Ala Pro Ala Pro Ala Pro Ser Trp Pro Leu Ser Ser Ser
                85                  90                  95

Val Pro Ser Gln Lys Thr Tyr Gln Gly Ser Tyr Gly Phe Arg Leu Gly
            100                 105                 110

Phe Leu His Ser Gly Thr Ala Lys Ser Val Thr Cys Thr Tyr Ser Pro
        115                 120                 125

Ala Leu Asn Lys Met Phe Cys Gln Leu Ala Lys Thr Cys Pro Val Gln
    130                 135                 140

Leu Trp Val Asp Ser Thr Pro Pro Pro Gly Thr Arg Val Arg Ala Met
145                 150                 155                 160

Ala Ile Tyr Lys Gln Ser Gln His Met Thr Glu Val Val Arg Arg Cys
                165                 170                 175

Pro His His Glu Arg Cys Ser Asp Ser Asp Gly Leu Ala Pro Pro Gln
            180                 185                 190

His Leu Ile Arg Val Glu Gly Asn Leu Arg Val Glu Tyr Leu Asp Asp
        195                 200                 205

Arg Asn Thr Phe Arg His Ser Val Val Val Pro Tyr Glu Pro Pro Glu
    210                 215                 220

Val Gly Ser Asp Cys Thr Thr Ile His Tyr Asn Tyr Met Cys Asn Ser
225                 230                 235                 240

Ser Cys Met Gly Gly Met Asn Arg Arg Pro Ile Leu Thr Ile Ile Thr
                245                 250                 255

Leu Glu Asp Ser Ser Gly Asn Leu Leu Gly Arg Asn Ser Phe Glu Val
            260                 265                 270

Arg Val Cys Ala Cys Pro Gly Arg Asp Arg Arg Thr Glu Glu Glu Asn
        275                 280                 285

Leu Arg Lys Lys Gly Glu Pro His His Glu Leu Pro Pro Gly Ser Thr
    290                 295                 300

Lys Arg Ala Leu Pro Asn Asn Thr Ser Ser Ser Pro Gln Pro Lys Lys
305                 310                 315                 320
```

-continued

```
Lys Pro Leu Asp Gly Glu Tyr Phe Thr Leu Gln Ile Arg Gly Arg Glu
                325                 330                 335

Arg Phe Glu Met Phe Arg Glu Leu Asn Glu Ala Leu Glu Leu Lys Asp
            340                 345                 350

Ala Gln Ala Gly Lys Glu Pro Gly Gly Ser Arg Ala His Ser Ser His
        355                 360                 365

Leu Lys Ser Lys Lys Gly Gln Ser Thr Ser Arg His Lys Lys Leu Met
    370                 375                 380

Phe Lys Thr Glu Gly Pro Asp Ser Asp
385                 390
```